US006749814B1

(12) United States Patent
Bergh et al.

(10) Patent No.: US 6,749,814 B1
(45) Date of Patent: *Jun. 15, 2004

(54) CHEMICAL PROCESSING MICROSYSTEMS COMPRISING PARALLEL FLOW MICROREACTORS AND METHODS FOR USING SAME

(75) Inventors: H. Sam Bergh, San Francisco, CA (US); Shenheng Guan, San Jose, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/518,794

(22) Filed: Mar. 3, 2000

Related U.S. Application Data

(60) Provisional application No. 60/122,704, filed on Mar. 3, 1999.

(51) Int. Cl.[7] ............................ B01J 19/00; G01N 31/00
(52) U.S. Cl. ........................ 422/130; 422/99; 422/100; 422/102; 422/129; 436/37
(58) Field of Search .................... 422/99–104, 129–131

(56) References Cited

U.S. PATENT DOCUMENTS

| 3,431,077 A | | 3/1969 | Danforth ..................... 23/253 |
| 3,797,202 A | * | 3/1974 | Neulander et al. ................ 96/5 |
| 3,966,420 A | | 6/1976 | Pegels et al. ............. 23/288 R |
| 4,099,923 A | | 7/1978 | Milberger ..................... 23/254 |

(List continued on next page.)

FOREIGN PATENT DOCUMENTS

| DE | 27 14 939 B2 | 10/1978 | |
| DE | 234 941 A1 | 2/1985 | |
| DE | 196 32 779 A1 | 2/1998 | .......... G01N/35/00 |
| DE | 198 05 719 A1 | 8/1999 | .......... B01J/35/04 |

(List continued on next page.)

OTHER PUBLICATIONS

G.M. Greenway, S.J. Haswell, D.O. Morgan, et al., "The Use of a Novel Microreactor for High Throughput Continuous Flow Organic Synthesis," Sensors and Actuators B–Chemical, 2000, 63, p. 153.

Burns et al., "Development of a Microreactor for Chemical Production," AIChE 2nd International Conference on Microreaction Technology, pp. 39–44 (1998).

(List continued on next page.)

Primary Examiner—Jill Warden
Assistant Examiner—Elizabeth Quan

(57) ABSTRACT

A chemical processing microsystem useful for identifying and optimizing materials (e.g., catalysts) that enhance chemical processes or for characterizing and/or optimizing chemical processes is disclosed. The chemical processing microsystem comprises a plurality of microreactors 600 and, in a preferred embodiment, a plurality of microseparators 900 integral with the chemical processing microsystem 10. The microreactors 600 are preferably diffusion-mixed microreactors formed in a plurality of laminae that include a modular, interchangeable candidate-material array 100. The material array 100 comprises a plurality of different candidate materials (e.g., catalysts), preferably arranged at separate, individually addressable portions of a substrate (e.g., wafer). The microseparators 900 are similarly formed in a plurality of laminae that include a modular, interchangeable adsorbent array 700. The adsorbent array 700 comprises one or more adsorbents, preferably arranged at separate, individually, addressable portions of a substrate to spatially correspond to the plurality of different candidate materials. Modular microfluidic distribution systems are also disclosed. The chemical processing microsystem can be integrated into a material evaluation system that enables a comprehensive combinatorial material science research program.

142 Claims, 46 Drawing Sheets

U.S. PATENT DOCUMENTS

| | | | |
|---|---|---|---|
| 4,386,505 A | 6/1983 | Little | 62/514 R |
| 4,392,362 A | 7/1983 | Little | 62/514 R |
| 4,516,632 A | 5/1985 | Swift et al. | 165/167 |
| 4,537,217 A | 8/1985 | Allen, Jr. | 137/561 |
| 4,636,315 A | 1/1987 | Allen, Jr. | 210/656 |
| 4,832,914 A | 5/1989 | Tam et al. | 422/130 |
| 4,921,919 A | 5/1990 | Lin et al. | 526/88 |
| 5,016,707 A | 5/1991 | Nguyen | 165/167 |
| 5,079,205 A | 1/1992 | Canich | 502/117 |
| 5,089,232 A | 2/1992 | May | 422/83 |
| 5,145,579 A | 9/1992 | Eguchi et al. | 210/198.2 |
| 5,209,906 A * | 5/1993 | Watkins et al. | 422/200 |
| 5,230,866 A | 7/1993 | Shartle et al. | 422/103 |
| 5,288,644 A | 2/1994 | Beavis et al. | 436/94 |
| 5,296,375 A | 3/1994 | Kricka et al. | 435/291 |
| 5,296,775 A | 3/1994 | Cronin et al. | 310/309 |
| 5,304,354 A * | 4/1994 | Finley et al. | 422/196 |
| 5,354,460 A | 10/1994 | Kearney et al. | 210/198.2 |
| 5,356,756 A | 10/1994 | Cavicchi et al. | 430/315 |
| 5,385,712 A | 1/1995 | Sprunk | 422/190 |
| 5,388,635 A | 2/1995 | Gruber et al. | 165/80.4 |
| 5,498,545 A | 3/1996 | Vestal | 436/47 |
| 5,534,328 A * | 7/1996 | Ashmead et al. | 428/166 |
| 5,580,523 A * | 12/1996 | Bard | 422/50 |
| 5,587,128 A | 12/1996 | Wilding et al. | 422/50 |
| 5,593,642 A | 1/1997 | DeWitt et al. | 422/131 |
| 5,603,351 A | 2/1997 | Cherukuri et al. | 137/597 |
| 5,611,214 A | 3/1997 | Wegeng et al. | 62/498 |
| 5,639,423 A | 6/1997 | Northrup et al. | 122/50 |
| 5,658,413 A | 8/1997 | Kaltenbach et al. | 156/272.8 |
| 5,658,537 A * | 8/1997 | Dugan | 422/191 |
| 5,690,763 A | 11/1997 | Ashmead et al. | 156/60 |
| 5,699,157 A | 12/1997 | Parce | 356/344 |
| 5,770,860 A | 6/1998 | Franzen | 250/288 |
| 5,776,359 A | 7/1998 | Schultz et al. | 252/62.51 |
| 5,811,062 A | 9/1998 | Wegeng et al. | 422/129 |
| 5,842,787 A | 12/1998 | Kopf-Sill et al. | 366/340 |
| 5,843,385 A | 12/1998 | Dugan | 422/191 |
| 5,846,396 A | 12/1998 | Zanzucchi et al. | 204/601 |
| 5,852,495 A | 12/1998 | Parce | 356/344 |
| 5,858,195 A | 1/1999 | Ramsey | 204/601 |
| 5,869,004 A | 2/1999 | Parce et al. | 422/100 |
| 5,872,010 A | 2/1999 | Karger et al. | 436/173 |
| 5,908,552 A | 6/1999 | Dittmann et al. | 210/198.2 |
| 5,935,277 A | 8/1999 | Autenrieth et al. | 48/127.9 |
| 5,938,333 A | 8/1999 | Kearney | 366/336 |
| 5,942,443 A | 8/1999 | Parce et al. | 436/514 |
| 5,948,227 A | 9/1999 | Dubrow | 204/455 |
| 5,955,028 A | 9/1999 | Chow | 422/63 |
| 5,957,579 A | 9/1999 | Kopf-Sill et al. | 366/340 |
| 5,959,297 A | 9/1999 | Weinberg et al. | 250/288 |
| 5,965,001 A | 10/1999 | Chow et al. | 204/600 |
| 5,965,410 A | 10/1999 | Chow et al. | 435/91.2 |
| 5,976,336 A | 11/1999 | Dubrow et al. | 204/453 |
| 5,989,402 A | 11/1999 | Chow et al. | 204/601 |
| 6,001,229 A | 12/1999 | Ramsey | 204/451 |
| 6,004,515 A | 12/1999 | Parce et al. | 422/100 |
| 6,010,607 A | 1/2000 | Ramsey | 204/435 |
| 6,010,608 A | 1/2000 | Ramsey | 204/453 |
| 6,042,709 A | 3/2000 | Parce et al. | 204/453 |
| 6,042,710 A | 3/2000 | Dubrow | 204/454 |
| 6,046,056 A | 4/2000 | Parce et al. | 436/514 |
| 6,068,684 A | 5/2000 | Overton | 96/101 |
| 6,068,752 A | 5/2000 | Dubrow et al. | 204/604 |
| 6,071,478 A | 6/2000 | Chow | 422/81 |
| 6,074,725 A | 6/2000 | Kennedy | 428/188 |
| 6,086,740 A | 7/2000 | Kennedy | 204/601 |
| 6,087,180 A | 7/2000 | Gleaves | 436/37 |
| 6,087,181 A | 7/2000 | Cong | 436/37 |
| 6,100,541 A | 8/2000 | Nagle et al. | 250/573 |
| 6,103,199 A | 8/2000 | Bjornson et al. | 422/100 |
| 6,123,798 A | 9/2000 | Gandhi et al. | 156/292 |
| 6,132,685 A | 10/2000 | Kercso et al. | 422/104 |
| 6,149,882 A | 11/2000 | Guan et al. | 422/211 |
| 6,287,872 B1 | 9/2001 | Schürenberg et al. | 436/181 |
| 6,319,719 B1 | 11/2001 | Bhullar et al. | 436/70 |
| 6,333,019 B1 | 12/2001 | Coppens | 423/659 |
| 6,350,617 B1 | 2/2002 | Hindsgaul et al. | 436/173 |
| 6,409,072 B1 * | 6/2002 | Breuer et al. | 228/111.5 |
| 6,426,226 B1 * | 7/2002 | Senkan | 436/37 |
| 6,485,692 B1 | 11/2002 | Frietag et al. | 422/130 |
| 2002/0042140 A1 | 4/2002 | Hagemeyer et al. | 436/34 |

FOREIGN PATENT DOCUMENTS

| | | | |
|---|---|---|---|
| DE | 198 06 848 A1 | 8/1999 | B01J/35/02 |
| DE | 198 09 477 A1 | 9/1999 | G01N/31/10 |
| DE | 198 55 894 A1 | 6/2000 | B01J/35/04 |
| EP | 0 870 541 A | 10/1998 | B01J/19/00 |
| EP | 971 225 | 1/2000 | G01N/21/17 |
| GB | 2 327 754 | 2/1999 | G01N/31/10 |
| WO | WO 96/15576 * | 5/1996 | |
| WO | WO 96/35810 | 11/1996 | C12Q/1/68 |
| WO | WO 97/32208 | 9/1997 | G01N/31/10 |
| WO | WO 98/07206 | 2/1998 | G01N/31/10 |
| WO | WO 98/14268 | 4/1998 | B01F/5/06 |
| WO | WO 98/16949 | 4/1998 | H01J/49/40 |
| WO | WO 98/56956 | 12/1998 | C12Q/1/70 |
| WO | WO 99/10221 | 1/1999 | B01L/3/00 |
| WO | WO 99/19724 * | 4/1999 | |
| WO | WO 99/30817 | 6/1999 | B01J/19/00 |
| WO | WO 99/34205 | 7/1999 | G01N/30/86 |
| WO | WO 99/41005 | 8/1999 | B01J/19/00 |
| WO | WO 99/43432 | 9/1999 | B01L/3/00 |
| WO | WO 99/48599 | 9/1999 | B01F/5/06 |
| WO | WO 99/59716 | 11/1999 | B01J/19/00 |
| WO | WO 99/64160 | 12/1999 | B01L/3/02 |
| WO | WO 99/64836 | 12/1999 | G01N/1/10 |
| WO | WO 00/07026 | 2/2000 | G01N/35/00 |
| WO | WO 00/14529 | 3/2000 | G01N/31/02 |
| WO | WO 00/21666 | 4/2000 | B01L/3/02 |
| WO | WO 00/22424 | 4/2000 | G01N/27/26 |
| WO | WO 00/32308 | 6/2000 | B01J/19/00 |
| WO | WO 00/32512 | 6/2000 | C01B/3/50 |
| WO | WO 0042212 | 7/2000 | C12Q/1/00 |
| WO | WO 00/43766 | 7/2000 | G01N/27/26 |
| WO | WO 00/45172 | 8/2000 | G01N/33/558 |
| WO | WO 00/46594 | 8/2000 | G01N/27/26 |
| WO | WO 00/50172 | 8/2000 | B01L/3/100 |
| WO | WO 01/12327 | 2/2001 | B01L/3/00 |

OTHER PUBLICATIONS

Cooke, "Decreasing Gas Chromatography Analysis Times Using a Multicapillary Column," Abs. 403P, Book of Abstracts, PittCon' '96 (1996).

Ehrfeld et al., "Potentials and Realizations of Microreactors," DECHEMA Monographs vol. 132, pp. 1–28 (1995).

Hanak et al., "Optimization Studies of Materials in Hydrogenated Amorphous Silicon Solar Cells," Photovoltaic Solar Energy Conference, Berlin (1979).

Honicke et al., "Heterogeneously Catalyzed Reactions in a Microreactor," DECHEMA Monographs vol. 132, pp. 93–107 (1995).

Johansson et al., "Nanofabrication of Model Catalysts and Simulations of their Reaction Kinetics," J. Vac. Sci. Technol., 17:1 (Jan./Feb. 1999).

Löwe et al., "Microreactor Concepts for Heterogeneous Gas Phase Reactions," AIChE $2^{nd}$ International Conference on Microreaction Technology, pp. 63–73 (1998).

Matlosz et al., "Microsectioned Electrochemical Reactors for Selective Partial Oxidation," AIChE $2^{nd}$ International Conference on Microreaction Technology, pp. 54–59 (1998).

S.M. Sze, "Semiconductor Sensors," Chap. 2, pp. 17–96, John Wiley & Sons, Inc. (1994).

Srinivasan et al., "Micromachined Reactors for Catalytic Partial Oxidation Reactions," AIChE Journal, vol. 43, No. 11, pp. 3059–3069 (1997).

Tonkovich et al., "The Catalytic Partial Oxidation of Methane in a Microchemical Reactor," AIChE $2^{nd}$ International Conference on Microreaction Technology, pp. 45–53 (1998).

van Dover et al., "Discovery of a Useful Thin–Film Dielectric Using a Composition–Spread Approach," Nature, vol. 392, No. 12, pp. 162–164 (1998).

Bunshah, "Handbook of Deposition Technologies for Films and Coatings," $2^{nd}$ Ed., Noyes Publications (1994).

Jackel, K.P., "Microtechnology: Application Opportunities in the Chemical Industry" DECHEMA Monographs, vol. 132, VCH Verlagsgesellschaft 1996, pp. 29–50.

Ackelid, Ulf, et al. "Kinetic Studies of Diffusion Limited Gas–Surface Reactions By Spatially Resolved Gas Sampling: Reaction Rates and Sticking Coefficients in the $H_2+O_2$ Reaction on Pt" Linköping Studies In Science and Technology, Dissertations No. 392, 1995, pp. 122–133.

Zech et al., "Simultaneous Screening of Catalysts in Microchannels: Methodology and Experimental Setup" 00–00–1998, pp. 260–266 (XP–001006374).

Randhava, Ravi et al. "Advanced Configurations For Catalyst Research" Chemical Engineering Progress, vol. 70, No. 11 Nov. 1983, pp. 52–58.

Sie, S.T. "Reducing the Scale in Catalytic Process Research: Cost Savings" I 2 Procestechnologie v. 7(3) 1991 Iprtez (Translation).

Rodemerck, Uwe, et al. "Parallel Synthesis and Testing Systems of Heterogeneous Catalysts".

Mirth, Gabriele et al. "Design and Application of a New Reactor for in Situ Infrared Spectroscopic Investigations of Heterogeneously Catalyzed Reactions" 1369 Applied Spectroscopy, 48(1994) Feb., No. 2, pp. 194–197.

Van den Berg et al., "Modular Concept for Miniature Chemical Systems," DECHEMA Monographs vol. 132 (1995), pp. 109–123.

* cited by examiner $n = 3, 4^n \equiv 64$

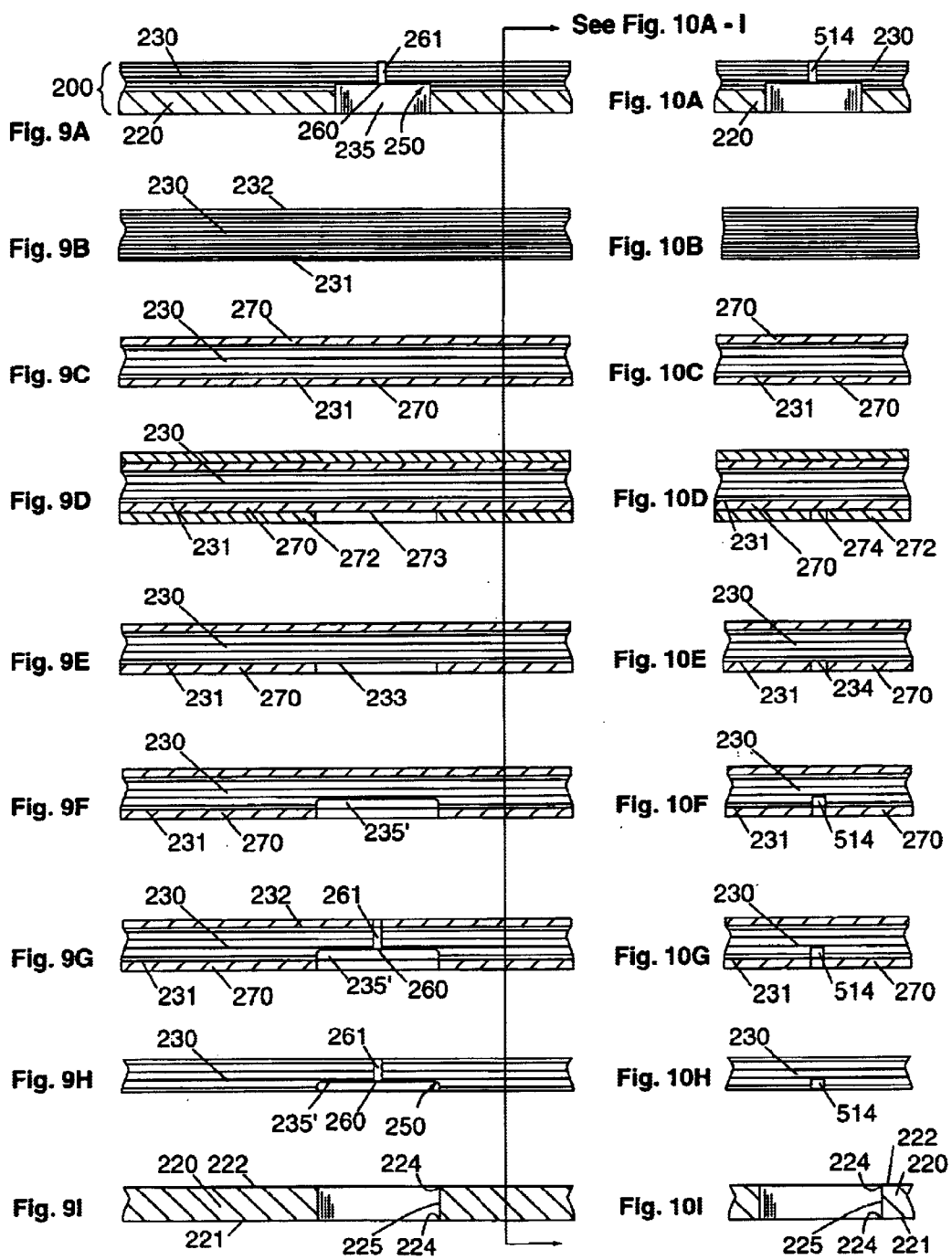

CHEMICAL PROCESSING MICROSYSTEMS COMPRISING PARALLEL FLOW MICROREACTORS AND METHODS FOR USING SAME

This application claims priority to commonly owned, co-pending U.S. patent application Ser. No. 60/122,704 filed Mar. 3, 1999 entitled "Chemical Processing Microsystems, Diffusion-Mixed Microreactors and Methods for Preparing and Using same", which is hereby incorporated by reference for all purposes.

BACKGROUND OF THE INVENTION

The present invention relates generally to the field of combinatorial chemistry and, in preferred applications, to the field of combinatorial materials science. In particular, the invention relates to systems and methods employing microfluidic devices in chemical processes, for characterizing and optimizing such chemical processes and for identifying materials that enhance such chemical processes. Preferred embodiments of the invention relate to microchemical processing systems, to diffusion-mixed microreactors, and to methods for identifying or optimizing heterogeneous catalysts.

Combinatorial chemistry refers generally to methods for synthesizing a collection of chemically diverse materials and to methods for rapidly testing or screening this collection of materials for desirable performance characteristics and properties. Combinatorial chemistry approaches have greatly improved the efficiency of discovery of useful materials. For example, material scientists have developed and applied combinatorial chemistry approaches to discover a variety of novel materials, including for example, high temperature superconductors, magnetoresistors, phosphors and catalysts. See, for example, U.S. Pat. No. 5,776,359 to Schultz et al. In comparison to traditional materials science research, combinatorial materials research can effectively evaluate much larger numbers of diverse compounds in a much shorter period of time. Although such high-throughput synthesis and screening methodologies are conceptually promising, substantial technical challenges exist for application thereof to specific research and commercial goals.

Microfluidics refers generally to the field of miniaturized fluidic systems. Microfluidic systems have been designed to perform similar tasks as larger scale commercial fluid systems, and have included a number of different micro-components such as fluid-distribution channels, valves, pumps, motors, mixers, heat-exchangers, condensers, evaporators, chemical reactors, chemical separators, sensors and actuators, among others. When microfluidic systems are integrated with microelectronics, the integrated systems are typically referred to as microelectromechanical systems (MEMS). When microfluidic systems include a chemical reactor and/or a chemical separator, the systems can be referred to as chemical processing Microsystems. Microfluidic systems have typically been fabricated using technology known in connection with integrated circuit fabrication.

A number of chemical processing microsystems have been developed to effect chemical and/or biochemical conversions, alone or in combination with other unit operations such as separation and analysis. See, for example, Ehrfeld et al., *Potentials and Realizations of Microreactors*, DECHEMA Monographs Vol. 132, pp. 1–28 (1995) and references cited therein. A microreactor is a common component of such chemical processing Microsystems, and a number of different microreactor designs have been developed to date. One type of microreactor design includes microchannels in which a reaction occurs as a fluid moves through one or more relatively long channels of relatively small hydraulic diameter. Microchannels offer a large surface area to volume ratio and, when coupled with microscale heat exchangers, offer exceptional temperature control for exothermic or endothermic reactions. Exemplary channel-type microreactors are disclosed in U.S. Pat. No. 5,811,062 to Wegeng et al., U.S. Pat. No. 5,534,328 to Ashmead et al., U.S. Pat. No. 5,690,763 to Ashmead et al., Tonkovich et al., The *Catalytic Partial Oxidation of Methane in a Microchemical Reactor*, AIChE $2^{nd}$ International Conference on Microreaction Technology, pp. 45–53 (1998), Honicke et al., *Heterogeneously Catalyzed Reactions in a Microreactor*, DECHEMA Monographs Vol. 132, pp. 93–107 (1995), and van den Berg et al., *Modular Concept for Miniature Chemical Systems*, DECHEMA Monographs Vol. 132, pp. 109–123 (1995). Cell-type microreactors, in which a reaction occurs while a fluid resides in a cell, have likewise been employed. Exemplary cell-type microreactors are disclosed in U.S. Pat. No. 5,843,385 to Dugan, U.S. Pat. No. 6,603,351 to Cherukuri et al., PCT Application WO 98/07206 of Windhab et al., and van den Berg et al., *Modular Concept for Miniature Chemical Systems*, supra. Microreactors that provide passive mixing and reaction of reactants in "Y"-shaped or "T"-shaped microchannels are disclosed in Burns et al., *Development of a Microreactor for Chemical Production*, AIChE $2^{nd}$ International Conference on Microreaction Technology, pp. 39–44 (1998), and in Srinivasan et al., *Micromachined Reactors for Catalytic Partial Oxidation Reactions*, AIChE Journal, Vol. 43, No. 11, pp.3059–3069 (1997). Microreactors for heterogenous phase reactions, such as gas-liquid or gas-solid reactions, are reported in Lowe et al., *Microreactor Concepts for Heterogeneous Gas Phase Reactions*, AIChE $2^{nd}$ International Conference on Microreaction Technology, pp. 63–73 (1998). Reactors specifically designed for certain classes of reactions, such as electrochemical reactions or photo-induced reactions have likewise been contemplated. See, for example, Matlosz et al., *Microsectioned Electrochemical Reactors for Selective Partial Oxidation*, AIChE $2^{nd}$ International Conference on Microreaction Technology, pp. 54–59 (1998).

Contemplated applications for such chemical processing microsystems include end-use production of hazardous chemicals, process characterization and optimization, and combinatorial chemistry. While combinatorial chemistry applications have been contemplated, the various chemical microreactor designs reported to date, however, have not been incorporated into systems suitable for large-scale, or even moderate-scale, combinatorial chemistry research, and particularly, for combinatorial material science research directed to heterogeneous catalyst screening for identification and/or optimization. For example, although parallel-type reactors and microreactors have been reported (see, e.g., U.S. Pat. No. 3,431,077 to Danforth, U.S. Pat. No. 4,099,923 to Milberger, U.S. Pat. No. 5,603,351 to Cherukuri et al. and PCT Application WO 98/07206 of Windhab et al.), none of these reactors are satisfactory for combinatorial materials science applications. These and other microreactor designs known in the art do not address important concerns such as the loading, and/or unloading of larger numbers of candidate materials (e.g., catalysts) for screening, the supplying of reactants to a plurality of microreactors, the controlling of the reaction conditions in a plurality of microreactors, and/or the evaluating of candidate materials for specific properties of interest (e.g., catalytic activity). Known microreactors also have common limitations, for example, with respect to a low throughput (e.g., the number of catalysts that can be screened over a given period of time), a narrow distribution of heterogeneous catalyst contact times, a large amount of each (often expensive) candidate catalyst required to effect the chemical conversion, the potential inherent negative influence of microreactor materials on a reaction of interest, a high degree of complexity, a lack of flexibility for analyzing the results of the chemical conversion, and, in some cases, a lack of scalability of research results to production-scale systems.

The present invention, as described in detail below, overcomes many, if not all of such shortcomings.

SUMMARY OF THE INVENTION

It is therefore an object of the present invention to provide cost-effective approaches for high-throughput combinatorial chemistry research and development, including particularly, research directed to the identification and optimization of new materials that enhance a chemical process and research directed to chemical process characterization and optimization.

It is also an object of the invention to provide chemical processing Microsystems that are relatively inexpensive to manufacture and use, that are flexible as to applications and variations, and that provide results which are scaleable to commercially significant systems.

Briefly, therefore, the present invention is directed to a chemical processing microsystem. The chemical processing microsystem generally comprises four or more microreactors and a fluid distribution system. Each of the microreactors comprise a surface defining a reaction cavity for carrying out a chemical reaction, an inlet port in fluid communication with the reaction cavity, and an outlet port in fluid communication with the reaction cavity. The reaction cavity has a volume of not more than about 10 ml, and in some applications, not more than about 3 ml, 1 ml, 100 $\mu$l, 10 $\mu$l or 1 $\mu$l. The fluid distribution system can supply one or more reactants from one or more external reactant sources to the inlet port of each reaction cavity and can discharge a reactor effluent from the outlet port of each reaction cavity to one or more external effluent sinks.

In one embodiment, the four or more microreactors of the chemical processing microsystem are arranged in a substantially planar array with a planar density of not less than about 1 microreactors/cm$^2$ and preferably not less than about 5 microreactors/cm$^2$.

In another embodiment, the chemical processing microsystem comprises two-hundred-fifty or more microreactors.

In a further embodiment, the chemical processing microsystem comprises ten or more microreactors and the distribution system includes a manifold comprising one or more common ports adaptable for fluid communication with one or more external reactant sources or one or more external reactor effluent sinks, ten or more terminal ports adaptable for fluid delivery to or fluid recovery from the ten or more microreactors, and a distribution channel providing fluid communication between the one or more common ports and each of the ten or more terminal ports. The ratio of the number of terminal ports to the number of common ports is at least about 10:1, and for some applications, at least about 100:1.

In an additional embodiment, the fluid distribution system of the chemical processing microsystem includes a manifold that comprises a common port adaptable for fluid communication with one or more external reactant sources or one or more external effluent sinks, $2^n$ terminal ports adaptable for fluid delivery to or fluid recovery from $2^n$ microreactors, and a distribution channel providing fluid communication between the common port and each of the $2^n$ terminal ports, where n is an integer of not less than 2, preferably of not less than 3, and more preferably of not less than 6. The distribution channel comprises $2^n-1$ channel sections, preferably linear channel sections, connected with each other through $2^n-1$ binary junctions. Each of the $2^n-1$ channel sections has at least three access ports serving as the common port, as a connection port for a binary junction, or as a terminal port. The microreactors are preferably arranged in a substantially planar array with a planar density of at least 1 microreactor/cm$^2$, and preferably of at least 5 microreactors/cm$^2$.

In a still further embodiment, the reaction cavity of each of the at least four microreactors has a geometry defined by ratios of distances X, Y, and Z measured within the reaction cavity along three mutually orthogonal lines having a common point of intersection at a midpoint of the longest line, Z, and oriented with the longest line, Z, normal to at least one surface that it intersects, and preferably normal to at least two surfaces that it intersects. The ratios of X:Z and Y:Z each range from about 1:2 to about 1:1.

In an alternative embodiment, the chemical processing microsystem further comprises four or more microseparators. Each of the microseparators comprises a surface defining a separation cavity for separating at least one component of a reactor effluent, an inlet port in fluid communication with the outlet port of one of the microreactors for receiving the reactor effluent therefrom, and an outlet port in fluid communication with the separation cavity for discharging the separated effluent therefrom. A fluid discharge system can discharge the separated reactor effluent from the outlet port of each separation cavity to one or more external effluent sinks. The microseparators can, in one exemplary embodiment, further comprise an adsorbent material for separating, preferably selectively, one or more components of a reactor effluent stream. The adsorbent material can be accessible for loading and unloading thereof into and out of the microseparators. For example, the microseparators can be formed in a plurality of adjacent laminae with at least one of the laminae being an adsorbent-containing laminate comprising a substrate and one or more adsorbent materials for adsorbing at least one component of the reactor effluent. A releasable seal can be situated between the adsorbent-containing laminate and one or more adjacent laminae in which the microseparators are formed.

In yet another embodiment, the chemical processing microsystem further comprises at least four different candidate materials being investigated for properties that enhance a chemical process of interest. Potential catalysts are exemplary candidate materials. The candidate materials are individually resident in the reaction cavity of separate microreactors. Each of the candidate materials comprises, or consists essentially of, an element, compound or composition selected from the group consisting of inorganic materials, metal-ligands and non-biological organic materials. The amount of the candidate material in each of the candidate-material containing microreactors is not more than about 10 mg, and for some applications, not more than about 5 mg, or not more than about 1 mg. The number of microreactors preferably ranges from about 7 to about 100, and in some applications from about 100 to about 250, from about 250 to about 400, from about 400 to about 1000. The number of microreactors can also be greater than about 1000. Not all of the microreactors have to contain a candidate material; rather some microreactors can be left as blanks or can contain control materials. Typically, different candidate materials are individually resident in the separate reaction cavities of at least 2%–100% of the microreactors, preferably of at least about 5% to about 99% of the microreactors. An analytical detection system can be in fluid communication with the outlet port of one or more of the microreactors. The microreactors of this embodiment can be further characterized by the various features or combinations of features summarized in the aforementioned paragraphs.

Each of the candidate-material-containing microreactors in the aforementioned chemical processing microsystem is, in one embodiment, accessible for unloading the candidate materials after the chemical reaction, and optionally, for reloading a second set of candidate materials. For example, the microreactors can be formed in a plurality of adjacent laminae, with at least one of the laminae being a candidate material-containing laminate comprising a substrate and the at least four candidate materials at separate portions of the substrate. For access, a releasable seal is situated between the material-containing laminate and one or more adjacent laminae in which the microreactors are formed.

In another embodiment, each of the candidate-material-containing microreactors in the aforementioned chemical processing microsystem is formed in a plurality of adjacent laminae. At least one of the laminae can be a candidate material-containing laminate that comprises a substrate and the at least four candidate materials at separate portions of the substrate, but that has an essential absence of fluid distribution microcomponents (or generally, components), and preferably also of temperature-control microcomponents (or generally, components) or other microcomponents (or generally, components). The material-containing laminate can be anodically bonded with adjacent laminate or can be releasably sealed therewith. Graphite gaskets are preferred in connection with the releasably sealed embodiment.

The present invention is also directed to methods for preparing a chemical processing microsystem for identifying and characterizing materials that enhance a chemical reaction. According to such methods, at least four different candidate materials are loaded into four or more microreactors such that the candidate materials are individually resident in a reaction cavity of a separate microreactor. Each of the candidate materials are an inorganic material, a metal-ligand, a non-biological organic material or a composition comprising various combinations thereof. Each of the microreactors comprise a surface defining a reaction cavity having a volume of not more than about 10 $\mu$l, an inlet port, and an outlet port as described above. The candidate materials can be loaded simultaneously, or alternatively, sequentially, into the four or more microreactors. The four or more microreactors can be formed in a plurality of laminae as described above, with the at least four candidate materials loaded into the four or more microreactors as a material-containing laminate as described above.

The present invention is further directed to methods for identifying or optimizing catalysts for a chemical reaction of interest. According to these methods, at least four different candidate materials are loaded into four or more microreactors of a chemical processing microsystem such that the at least four different candidate materials are individually resident in separate microreactors. Each of the microreactors comprise a surface defining a reaction cavity having a volume of not more than about 1 ml, preferably less than about 100 $\mu$l, or even less than about 10 $\mu$l. Each of the candidate materials are elements, compounds or compositions comprising one or more inorganic materials, one or more metal-ligands or one or more non-biological organic materials, separately or in various possible combinations.

For such methods, the candidate materials can be loaded simultaneously, or alternatively sequentially, into the four or more microreactors. In preferred approaches, the candidate materials are loaded without affecting the structural integrity of a fluid distribution system through which the one or more reactants are supplied to the microreactors or through which one or more reactor effluents are discharged from the microreactors.

In such methods, one or more reactants are simultaneously supplied to each of the at least four candidate material-containing microreactors, and simultaneously contacted with each of the at least four candidate materials. The reaction conditions are controlled to be conducive to, or intended to be conducive to, effecting the chemical reaction of interest. In some approaches, the reaction conditions are controlled to be substantially the same in each of the four or more microreactors, or at least in some subset of at least four or more microreactors. For many applications, the temperature is controlled to be not less than about 100° C. and to be substantially the same in each of the four or more microreactors or in a subset thereof. For many applications, the residence time can be controlled to range from about 1 $\mu$sec about 1 hour and to be substantially the same in each of the four or more microreactors or in a subset thereof. In some applications, the reaction conditions can be controlled such that the reactant residence time, $\tau_{res}$, is longer than the diffusion period, $\tau_{diff}$, for the reaction cavity. A reactor effluent is simultaneously discharged from each of the at least four candidate material-containing microreactors.

The at least four candidate materials can, according to such methods, be evaluated for catalytic activity (e.g., yield, conversion) or selectivity for the chemical reaction of interest. The candidate materials can, for example, be evaluated for catalytic activity by in situ analytical measurement, or analytical measurement of the reactor effluent. The candidate materials can be evaluated for catalytic activity by serial, parallel or serial-parallel (subgroup hybrid) analytical measurement. Detection approaches can include, with or without pre-separation of analyte component, gas chromatography, mass spectroscopy and optical spectroscopy, among other approaches. In a preferred approach, separation of one or more reactor effluent components is effected by adsorbing the component analyte onto an adsorbent material. Evaluation can then be accomplished by desorbing the adsorbed analyte component, and determining the desorbed analyte component, or alternatively, by reacting the adsorbed material with a detection agent (e.g. indicating agent) to form a detectable species, and then detecting the presence, absence or relative or absolute quantity of the detectable species.

Such methods can be further characterized with respect to the candidate-material evaluation throughput. For example, the candidate materials can be evaluated for catalytic activity (e.g. yield) at a throughput of not less than about 1 candidate material/hour. In preferred applications, the throughput can be not less than about 1 candidate material/second.

In some applications, these methods of the invention can further comprise unloading the reactant-contacted candidate materials from the microreactors in which they reside, and then loading a second set of at least four different candidate materials into the four or more microreactors of the chemical processing microsystem such that the second set of at least four different candidate materials are individually resident in separate microreactors. Such reiterative loading and unloading of candidate materials can be advantageously effected using many of the chemical processing microsystems as characterized above, with such features being employed alone or in any of the various possible combinations.

The present invention is likewise directed to methods for evaluating or optimizing process conditions for a chemical reaction of interest. Such methods generally comprise simultaneously supplying one or more reactants to each of four or more microreactors (where such microreactors can be characterized as summarized above), controlling a first set of reaction conditions to be substantially identical in each of the microreactors, controlling a second set of reaction conditions to be varied between two or more of the microreactors, simultaneously discharging a reactor effluent from each of the four or more microreactors, and evaluating the effect of varying the second set of reaction conditions.

The invention is directed, moreover, to a distribution manifold for distributing fluids in microfluidic systems. The manifold comprises a common port adaptable for fluid communication with one or more fluid sources or sinks, $2^n$ terminal ports adaptable for fluid delivery to or fluid recovery from $2^n$ microcomponents, n being an integer not less than 2 and preferably not less than 6, and a distribution channel providing fluid communication between the common port and each of the $2^n$ terminal ports. The distribution channel comprises $2^n-1$ channel sections, preferably linear channel sections, connected with each other through $2^n-1$ binary junctions. Each of the $2^n-1$ channel sections has at least three access ports serving as the common port, as a connection port for a binary junction, or as a terminal port. The $2^n$ microcomponents are preferably arranged in a substantially planar array with a planar density of not less than about 1 microcomponent/cm$^2$.

The invention is, in another case, directed to methods for providing fluids to or removing fluids from a plurality of microcomponents. These methods comprise simultaneously supplying a fluid to, or discharging a fluid from, each of $2^n$ microcomponents, where n is an integer of not less than 2, and preferably not less than 6. The fluid is supplied or discharged through a distribution manifold having features as summarized in the immediately preceding paragraph.

The present invention is still further directed to a microreactor for microscale chemical reactions. The microreactor comprises a surface defining a reaction cavity for carrying out a chemical reaction, an inlet port in fluid communication with the reaction cavity for supplying one or more reactants thereto, and an outlet port in fluid communication with the reaction cavity for discharging one or more reaction products therefrom. The reaction cavity has a volume of not more than about 10 µl and a geometry defined by ratios of distances X, Y, and Z measured within the reaction cavity along three mutually orthogonal lines having a common point of intersection at a midpoint of the longest line, Z, with the longest line, Z, being normal to at least one surface with which it intersects and, where allowed by the geometry, with at least two surfaces with which it intersects. The reaction cavity geometry is characterized by ratios of X:Z and Y:Z each ranging from about 1:2 to about 1:1.

The present invention is directed, as well, to methods for effecting a microscale chemical reaction. One or more reactants for a chemical reaction of interest are supplied to a microreactor comprising a surface defining a reaction cavity having a volume of not more than about 10 µl for carrying out a chemical reaction, an inlet port in fluid communication with the reaction cavity for supplying one or more reactants thereto, and an outlet port in fluid communication with the reaction cavity for discharging one or more reaction products therefrom. The reactants reside in the reaction cavity under process conditions effective for the chemical reaction of interest for a residence time, $\tau_{res}$ that is longer than the diffusion period, $\tau_{diff}$, for the reaction cavity under such process conditions, and the reactants are thereby converted to one or more reaction products in the reaction cavity.

As such, the devices, systems, and methods of the present invention offer distinct advantages over the prior-art. The chemical processing Microsystems of the present invention provide efficient means for loading and unloading candidate materials being evaluated, for supplying reactants to a plurality of microreactors, for controlling of the reaction conditions in a plurality of microreactors, and for evaluating the candidate materials for specific properties of interest (e.g., catalytic activity). Additionally, the instant chemical processing Microsystems can be employed for screening candidate materials such as catalysts with very high-throughput and with a large degree of analytical flexibility. Moreover, the chemical processing Microsystems of the invention require only a small amount of candidate materials relative to known systems, yet offer catalyst contact times that are generally representative of those employed in production-scale reactors. Advantageously, the contact-time distribution is, for one embodiment of microreactors, broader than the distribution associated with known microreactor designs, and is, therefore, better suited to a combinatorial primary screen than known designs. Additionally, the chemical processing microsystems of the present invention can be relatively inexpensively manufactured using commercially available technologies.

The devices, systems and methods of the invention have a primary application in the field of combinatorial materials science research for identifying and optimizing new materials that enhance chemical processes. Nonetheless, many of such devices, systems and methods will also find applications in other areas, such as combinatorial chemistry generally (including pharmaceutical and biotechnological applications), process characterization and optimization and small-quantity, end-use manufacturing (for example, of hazardous chemicals among others).

Other objects, features and advantages of the present invention will be in part apparent to those skilled in the art and in part pointed out hereinafter. All references cited herein, whether as part of the background or as part of the detailed description, are incorporated herein by reference for all purposes. Moreover, as the patent and non-patent literature relating to the subject matter disclosed and/or claimed herein is substantial, many relevant references are available to a skilled artisan that will provide further instruction with respect to such subject matter.

BRIEF DESCRIPTION OF THE DRAWINGS

FIG. 7A is a top-plan view of a typical fluid distribution manifold. FIG. 7B is a top-plan view of preferred binary-tree fluid distribution manifolds serving an array of 256 microreactors. FIGS. 7C and 7D are perspective views of ternary and quaternary fluid distribution manifolds, respectively, serving 27 and 64 microcomponents, respectively. FIG. 7E is a top-plan view showing one flow-path of the binary-tree distribution manifold of FIG. 7B (rotated about 90° clockwise from its orientation in FIG. 7B). FIG. 7F is a top-plan view of a microreactor having inlet and outlet ports in fluid communication with the distribution manifolds. FIG. 7G and FIG. 7H are top plan views of other fluid distribution systems serving chemical processing microsystems having microreactors and microseparators integrated onto a single, substantially planar wafer substrate. More specifically, FIG. 7G shows a partial-binary supply manifold serving 32 microreactors, interconnecting manifolds to 32 dedicated microseparators and a partial-binary separator effluent manifold. FIG. 7H shows a binary-tree supply manifold serving 128 microreactors, interconnecting manifolds to 128 dedicated microseparators and a binary-tree separator effluent manifold. FIG. 7I is a top-plan view of another preferred binary-tree fluid distribution manifold serving an array of 256 microreactors and having a single common inlet port 510 situated near the periphery thereof.

FIG. 9A through FIG. 9I are partial cross-sectional side views of various laminae showing intermediate composite structures during the fabrication of a microreactor shown in FIG. 8.

FIG. 10A through FIG. 10I are partial cross-sectional side views of various laminae taken at line I—I of FIGS. 9A through 10A, respectively.

FIGS. 16A and 16B show, respectively, a top plan view of a substantially planar wafer substrate for an array of 256 adsorbent materials (FIG. 16A), and a partial-cross-sectional side view of an individual well formed in one surface of the wafer substrate (FIG. 16B) into which the adsorbent materials can be deposited. FIG. 16C is a top plan view of an array of substantially parallel thin-layer chromatography (TLC) channels comprising adsorbent material and being adapted for fluid communication with distribution systems for a mobile-phase eluant. FIG. 16D shows a top plan view of a substantially planar wafer substrate for an array of 128 microreactors with an effluent distribution manifold that allows for adsorption of effluent components onto adsorbent material provided in microseparators (900) arranged in a row near the periphery of the wafer. FIG. 16E shows a top plan view of a substantially planar wafer having an array of microseparators arranged in a row to correspond with an row of aperatures (519 of FIG. 16D), and in fluid communication therewith.

FIG. 18A and FIG. 18B are, respectively, a partial cross-sectional side view of a modular chemical processing microsystem (FIG. 18A) having a plurality of microreactors and a plurality of microseparators formed in a plurality of laminae, and a perspective view of a partially-assembled housing (FIG. 18B) adaptable for assembly and operation of the modular chemical processing microsystem of FIG. 18A. FIGS. 18C and 18D show, respectively, an additional perspective view (FIG. 18C) and a corresponding side sectional view (taken at A—A) (FIG. 18D) of a partially-assembled housing and microsystem. Various subcomponents of the chemical processing microsystem of FIGS. 18C and 18D are shown in FIGS. 18E through 18I, including: a bottom plan view of a first microreactor support block (FIG. 18E), a perspective view of an external fluid distribution subassembly (FIG. 18F), a perspective view (FIG. 18G) and a corresponding cross-sectional view (taken at B—B) (FIG. 18H) of a fluid distribution subassembly and a schematic diagram (FIG. 18I) for the extneral fluid distribution subassembly. FIG. 18J is a schematic diagram for a modular chemical processing microsystem that includes a plurality of "flow-through" microreactors.

FIG. 20A is a graph showing a calibration plot of integrated intensity of fluorescence measured using a CCD camera against various amounts of a known analyte. FIG. 20B is a graph showing detector output (integrated fluorescence intensity measured using a CCD camera versus catalyst loading (mass fraction of total catalyst) in the reaction cavities of various microreactors. FIG. 20C is an output image showing detector output (fluorescence intensity) measured using a CCD camera for operation of the integrated parallel microreactor/microseparator system with catalysts loaded only in certain microreactors (demonstrating a lack of substantial cross-talk between adjacent microreactors). FIGS. 20D through 20F each show output images (fluorescence intensity) measured using a CCD camera for experiments directed toward identifying and optimizing catalysts for a particular reaction of interest, where compositional variations were explored using ternary libraries of noble metals (NM) and transition metals (TM) (FIG. 20D), ternary libraries of noble metals (NM) and dopants (D) (FIG. 20E), and ternary libraries of promising catalysts identified from these experiments with various catalyst support materials (FIG. 20F).

Figure 1A:
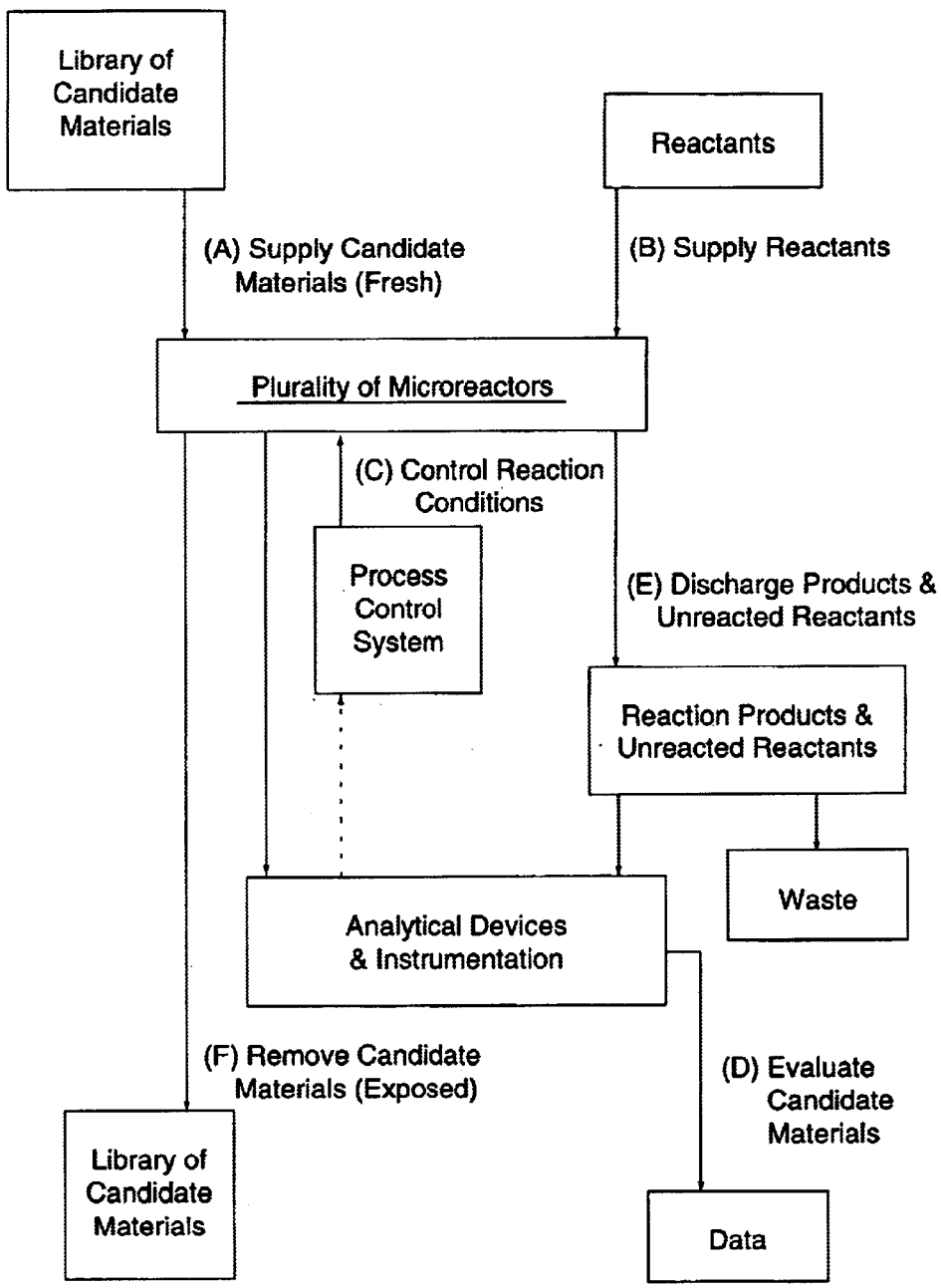
FIG. 1A through FIG. 1C are schematic diagrams showing the general steps for identifying and/or optimizing materials that enhance a chemical process (FIG. 1A), as well as more specific, preferred approaches (FIG. 1B) and embodiments (FIG. 1C) for the same.

The invention is described in detail below with reference to the figures, in which like items are numbered the same in each of the several figures.

DETAILED DESCRIPTION OF THE INVENTION

In the present invention, a chemical processing microsystem having features that enable an effective combinatorial materials science research program is provided. Such a research program may be directed, for example, to identifying or optimizing materials that enhance a chemical process, or to other research goals, such as process characterization or optimization. The systems, devices and methods disclosed herein can also be adapted to the production of small quantities of chemicals.

Among the several significant aspects of the present invention, approaches and devices are presented for efficiently loading, unloading and/or reloading a plurality of different materials into and out of a plurality of microreactors—for screening of the materials as candidates for a capability to enhance a chemical process. In one embodiment, the chemical processing microsystem can include a plurality of microreactors for carrying out a chemical process of interest, and integral therewith, an array of two or more materials known to enhance or being screened for a capability to enhance the chemical process. At least a portion of a material-containing region of the array is within each (or most) of the microreactors (exceptions being, for example, for control microreactors that may not have such a material included therein). Significantly, the array of materials can be readily and conveniently added to or removed from the other structural elements that define the chemical processing microsystem, such that different arrays can be interchanged with each other, with minimal effort, and without substantially affecting the structural integrity of the other structural elements of the chemical processing microsystem. The interchangeability of different arrays of materials into a chemical processing microsystem allows for the simultaneous loading of the various candidate materials to the plurality of microreactors, and, after the chemical reaction has been effected, simultaneous unloading therefrom. Significantly, therefore, the interchangeable arrays, particularly arrays that include over 250 different candidate materials, enable a researcher to screen a very large number of candidate materials in a relatively short period of time, in a cost-effective manner. Such interchangeable arrays are also advantageous for screening more moderate numbers of candidate materials.

In another aspect of the chemical processing microsystem of the invention, approaches and devices are disclosed for efficiently supplying reactants to each of a plurality of microreactors and for establishing reaction conditions in each of the plurality of microreactors that are substantially identical or, in alternative embodiments, that are controllably varied between microreactors. In a preferred embodiment, the fluid distribution manifold for fluid communication between each of a plurality of parallel microreactors and a common external fluid source or sink is designed such that the pressure is the same at each microreactor inlet and the volumetric flow rate is the same through each microreactor. Distribution manifolds having such equi-flow and equi-pressure characteristics can be achieved by providing flow paths having equal conductance—for example, flow paths of equal length and equivalent geometry—from the common port to each of the microreactors. Such design objectives, while perhaps straightforward for chemical processing Microsystems having relatively few microreactors and/or for chemical processing Microsystems that are unconstrained with respect to space considerations, present substantial engineering challenges for chemical processing microsystems having greater than ten microreactors and/or having a planar microreactor concentration of greater than about 5 microreactors/cm$^2$.

In a further aspect the invention, the chemical processing microsystem can include a diffusion-mixed microreactor. The diffusion-mixed microreactor is designed such that when operating as a continuous flow reactor—where one or more reactants for a chemical reaction of interest is continuously supplied to the microreactor, the reaction occurs therein under process conditions effective for the chemical reaction of interest, and a reaction effluent stream is continuously discharged therefrom—the reactants reside in the reaction cavity for a residence time, $\tau_{res}$, that is longer than the diffusion period, $\tau_{diff}$, for the reaction cavity under such process conditions. As such, mixing of reactants is achieved on a microscopic level without an active mixing microcomponent. Significantly, the continuous diffusion-mixed microreactor is representative of and can be used to model, on a microscopic scale, a continuous stirred-tank reactor (CSTR). Such diffusion-mixed microreactors are advantageous over channel-type microreactors (including microreactors having tortuous channels to effect passive mixing), because complete mixing can occur within a much smaller volume. This advantage has substantial implications for combinatorial research (e.g., directed to heterogeneously catalyzed reactions) because a much smaller amount of each of the plurality of materials (e.g., catalysts) is required to effect the experiment. Moreover, the diffusion-mixed microreactors offer a broader distribution of residence times than channel-type microreactors designed to model plug-flow reactors. As discussed in detail below, such a broader distribution of residence times can be advantageous in combinatorial material research applications—particularly for use as a primary screen.

As an additional aspect of the invention, the chemical processing microsystem can be configured with flexibility to employ a wide variety of instrumentation for determining the extent to which the chemical reaction of interest occurs in each of the microreactors. Such analytical determinations are important for evaluating a candidate material or for characterizing or optimizing the chemical reaction of interest. The analytical determinations can be carried out by in situ sampling in the microreactor, or alternatively, by discharging a reaction effluent stream comprising one or more reaction products formed by the reaction of interest, if any, and unreacted gaseous reactants, if any, from each of the microreactors to the analytical instrumentation. In the latter case, the reaction effluent can be discharged simultaneously (in parallel) or sequentially (in rapid serial) from each microreactor. The analytical instrumentation could be completely integral with the chemical processing microsystem, partially integral therewith, or completely independent therefrom. In a preferred, partially integrated embodiment, the reaction effluent is discharged from each of the microreactors to dedicated separation chambers, each separation chamber having, integral therewith, an adsorbent material for adsorbing at least one of the reaction products and/or unreacted gaseous reactants. The adsorbent materials are preferably on a common substrate that can be readily and conveniently added to or removed from the other structural elements that define the chemical processing microsystem, such that different adsorbent-containing substrates can be interchanged with each other, with minimal effort, and without substantially affecting the structural integrity of the other structural elements of the chemical processing microsystem. The interchangeability of the adsorbent-containing substrates into a single chemical processing microsystem allows for simultaneous, parallel separation of one or more of the various reaction products and/or excess reactants. Such interchangeability also allows for simultaneously fixing or recording the results of the screening in a physical form, such that the analytical determination can be completed at a different location and at a later time in parallel or serial fashion, thereby freeing the chemical processing microsystem for screening the next array of candidate materials, and improving overall throughput.

These and other aspects of the invention are discussed in greater detail below. The several aspects of the chemical processing microsystem disclosed and claimed herein can be advantageously employed separately, or in combination to identify and optimize materials that enhance chemical processes, to characterize and optimize chemical processes, and if desired, to prepare microamounts of chemicals. In preferred embodiments, these features are employed in combination to form a chemical processing microsystem that can operate as a primary screen or secondary screen in a materials science research program directed to identifying and optimizing new materials such as heterogeneous catalysts.

Identifying/optimizing Materials that Enhance a Chemical Process

A large number of chemical processes are enhanced by materials. The catalysis of chemical reactions is exemplary, and of substantial commercial significance. Additionally, however, other processes—such as separations and other unit operations that affect the chemical or physical state of a material of interest—can likewise be enhanced by materials. For example, adsorbents that are selective for a particular species can enhance the separation of that species from a mixture including the species. As another example, stabilizers used in chemical compositions can impact the rate of decomposition of such compositions, ultimately affecting the shelf-life thereof. Likewise, blocking moieties or scavengers can enhance the yield of a chemical reaction of interest by retarding an undesirable side reaction. Hence, while details of the present invention are primarily described herein in connection with the catalysis of chemical reactions and, particularly, in connection with heterogeneous catalysis, such applications should be considered exemplary and non-limiting with respect to other potential applications of the invention. Moreover, while much of the discussion presented herein is directed toward identifying materials (e.g., catalysts) that enhance a certain specific reaction of interest, the devices, systems and approaches disclosed herein can likewise be directed toward identifying which reactions are enhanced (e.g., catalyzed) by a certain specific material (e.g., catalyst) of interest.

According to one approach for identifying such useful materials, a large compositional space of potential candidate materials may be rapidly explored through the preparation and evaluation of candidate material libraries. Such candidate material libraries can comprise, for example, compositional gradients of two or more components, such as binary compositional gradients of components A and B, ternary compositional gradients of components A, B, and C, or higher-order compositional gradients. Candidate material libraries could alternatively comprise compounds having a number of structural variations relative to a base compound, such that the compounds in the library share a common structural scaffold.

In an initial, primary screening, candidate materials can be rapidly evaluated over a large compositional space according to the systems, devices and methods of the present invention to provide valuable preliminary data and, optimally, to identify several "hits"—particular candidate materials having characteristics that meet or exceed certain predetermined metrics (e.g., performance characteristics, properties, etc.). Such metrics may be defined, for example, by the characteristics of the then best known material for the chemical process of interest. The first candidate material libraries run through a primary screening can comprise, for example, full-range compositional gradients having compositional ratios ranging from 0% to 100% for each component. Because local performance maxima may be located at compositions between those particular compositions evaluated in the primary screening of the first libraries, it may be advantageous to screen more focused libraries (e.g., libraries focused on a smaller range of compositional gradients, or libraries comprising compounds having incrementally smaller structural variations relative to those of the identified hits). Hence, the primary screen can be used reiteratively to explore localized and/or optimized compositional space in greater detail. The preparation and evaluation of more focused libraries can continue as long as the high-throughput primary screen can meaningfully distinguish between neighboring library compositions or compounds.

Once one or more hits have been satisfactorily identified based on the primary screening, libraries having candidate materials focused around the primary-screen hits can be evaluated with a secondary screen—a screen designed to provide (and typically verified, based on known materials, to provide) chemical process conditions that may be scaled up with a greater degree of confidence than those applied in the primary screen. Particular candidate materials having characteristics that surpass the predetermined metrics for the secondary screen may then be considered to be a "lead" material. If desired, additional libraries comprising candidate materials focused about such lead materials can be screened with additional secondary screens. Identified lead materials may be subsequently developed for commercial applications through traditional bench-scale and/or pilot scale experiments.

While the concept of primary screens and secondary screens as outlined above provides a valuable combinatorial research model for many materials of interest and for many chemical processes, a secondary screen may not be necessary for certain chemical processes where primary screens provide an adequate level of confidence as to scalability and/or where market conditions warrant a direct development approach. Similarly, where optimization of materials having known properties of interest is desired, it may be appropriate to start with a secondary screen. In general, the systems, devices and methods of the present invention may be applied as either a primary or a secondary screen for one or more libraries of candidate materials, to identify candidate materials that enhance the chemical process of interest.

According to the present invention, methods, systems and devices are disclosed that improve the efficiency and/or effectiveness of the steps necessary to screen multiple libraries of candidate materials. With reference to FIG. 1A, screening a library of candidate materials for a capability to enhance a chemical reaction of interest requires (A) supplying different candidate materials to different microreactors, (B) providing reactants to the microreactors, (C) controlling reaction conditions in each microreactor to effect the chemical reaction of interest in the presence of the candidate material, and (D) evaluating each of the candidate materials with respect to their capability for enhancing the chemical reaction. If the microreactors are to operate as a continuous reactor, rather than as a batch reactor, then screening will also require (E) discharging reaction products, if any, and excess reactants, if any, from the microreactors. Except where the microreactors used for such screening are considered to be "single-load", disposable systems, or where the same library of candidate materials will be rescreened (e.g., under different reaction conditions), reuse of the same microreactors for screening a second library of candidate materials will also require (F) removing the candidate materials that had been exposed to the reaction conditions from each of the microreactors. Once the exposed candidate materials are removed from each of the microreactors, steps (A) through (D), optionally step (E), and preferably step (F) can be repeated, as necessary.

Figure 1B:
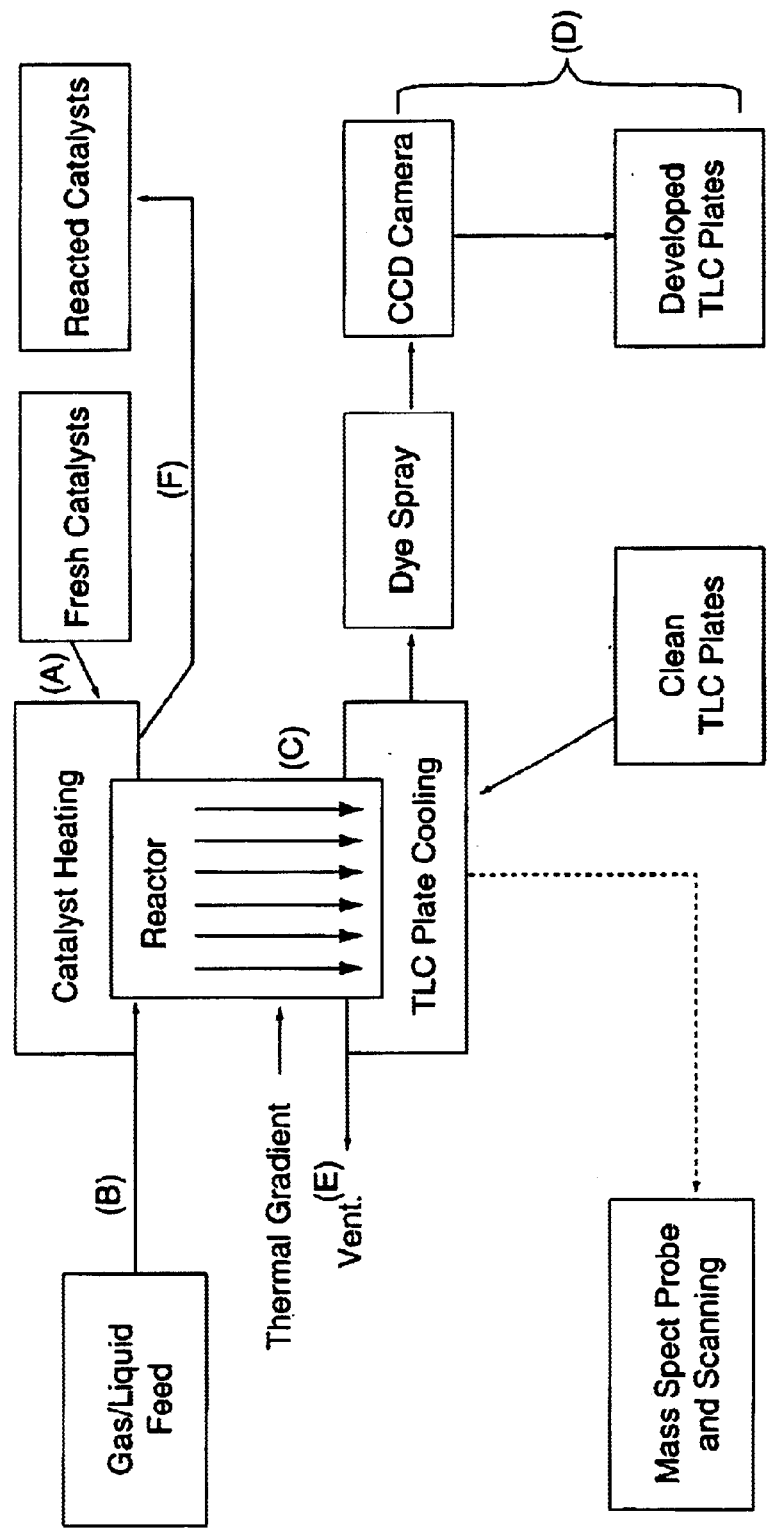

Each of the steps, (A) through (F), depicted in FIG. 1A can be optimized, individually or in combination, to effect a high-throughput research program for identifying reaction-enhancing materials such as catalysts. As a general approach, each of the steps (A) through (F) can be done in parallel for the plurality of candidate materials and respective microreactors. Moreover, each of the individual steps (A) through (F) can, where possible, be performed concurrently with others of such steps during the same cycle of steps, or where possible, performed after a first cycle of steps is complete, and concurrently with a second cycle of steps (A) through (F). For example, with reference to FIGS. 1A and 1B, in a preferred approach for screening multiple libraries of candidate materials (e.g., catalysts) using the same set of microreactors, the fresh candidate materials are supplied simultaneously to each of the respective microreactors (step A), reactants (e.g., gas or liquid) are supplied simultaneously to each of the microreactors (either concurrently with or temporally separate from the supply of candidate materials) (step B), reactions are effected in parallel (step C), reaction products and unreacted reactants are discharged simultaneously from each of the microreactors (step E), each of the candidate materials are evaluated simultaneously (e.g., by adsorbent trapping of a reaction product and dye-based imaging, by gas chromatography and/or by mass spectroscopy among other approaches) (step D), and/or the exposed candidate materials (e.g., catalysts) are removed simultaneously from each of the microreactors (step F). Notable, simultaneous delivery and removal of each of the candidate materials to their respective microreactors is advantageous in that different libraries of candidate materials can be quickly interchanged with the microreactors, thereby improving overall throughput. It may also be advantageous, with respect to overall throughput, to perform the evaluation step (D) concurrently with the reaction of interest using in situ measurement and analytical systems, and/or after the reaction of interest, but in parallel with or after the removal step (F). For example, with the proper analytical system, the evaluation step (D) for a first library of candidate materials can be performed while a second library of candidate materials is going through steps (A) through (C), and optionally steps (E) and (F).

Figure 1C:
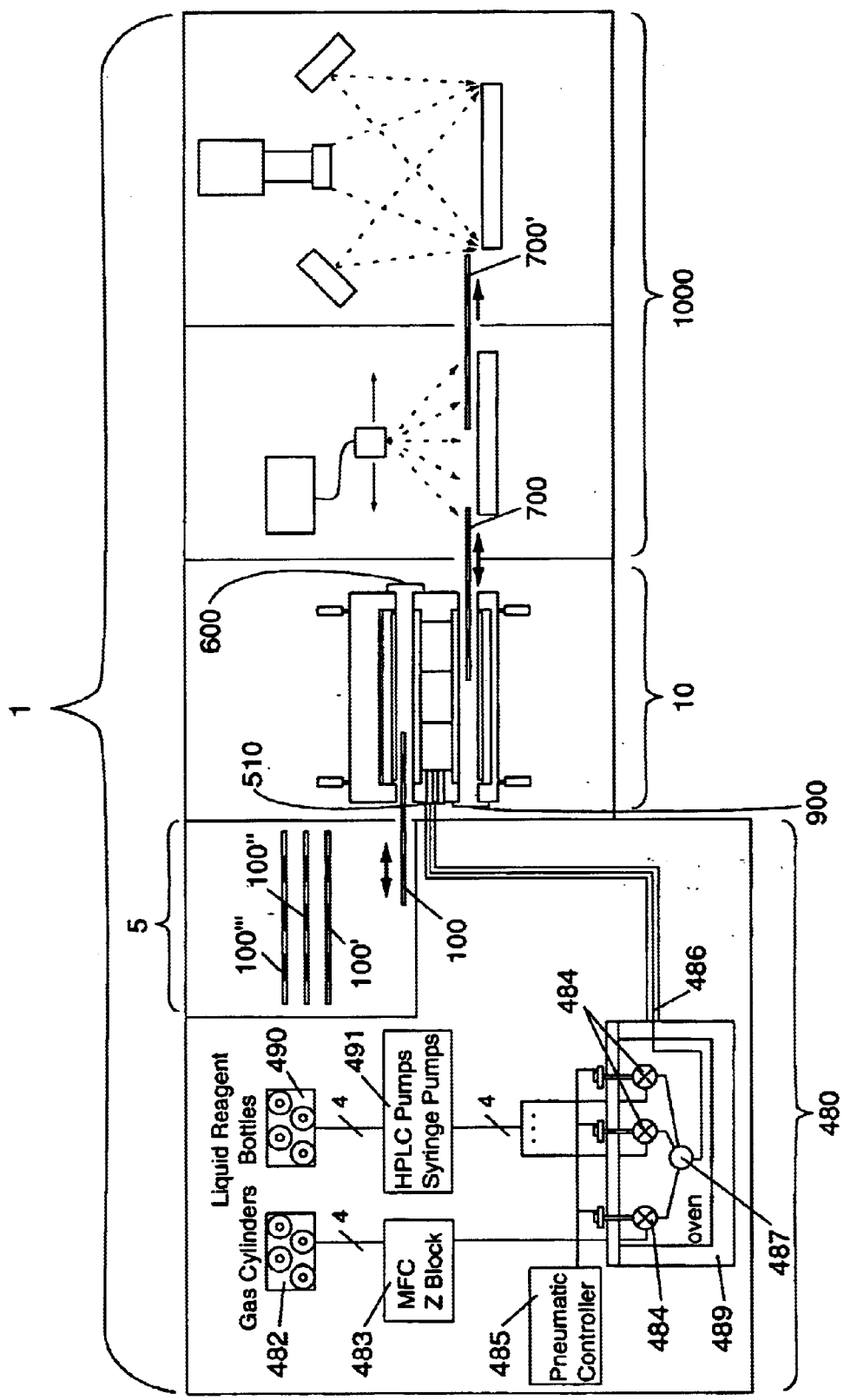

In a preferred embodiment represented schematically in FIG. 1C, the chemical processing microsystem of the present invention is integrated into a material evaluation system for effectively and efficiently evaluating new materials such as catalysts. Briefly, a material evaluation system 1 can comprise a chemical processing microsystem 10 for simultaneously effecting a chemical process (e.g., reaction) of interest in the presence of a plurality of candidate materials (e.g., catalysts) being evaluated, and, in preferred embodiments, for simultaneously separating a characteristic component (e.g., reaction product) resulting from such process, a detection system 1000 for characterizing (e.g., quantitatively determining) such a characteristic component, a material library handling system 5 for supplying and removing entire libraries of candidate materials to and from the chemical processing microsystem 10 for screening therein, and a fluid distribution system 480 for supplying fluids (e.g., reactants) to the chemical processing microsystem and, except for batch processes, for discharging fluids (e.g., reactor effluent stream) from the chemical processing microsystem. The chemical processing microsystem 10 comprises a plurality of microreactors 600 and, in a preferred embodiment, a plurality of microseparators 900 integral with the plurality of microreactors. The microprocessors 600 are formed in a plurality of laminae that include an interchangeable candidate-material array 100. The material array 100 comprises a plurality of different candidate materials (e.g., catalysts), preferably arranged at separate, individually addressable portions of a substrate (e.g., wafer). The microseparators 900 are similarly formed in a plurality of laminae that include an interchangeable adsorbent array 700. The adsorbent array 700 comprises one or more adsorbents, preferably arranged at separate, individually addressable portions of a substrate to spatially correspond to the plurality of different candidate materials.

In operation, for example, in connection with research directed to identifying new catalysts for a chemical reaction, a first material array 100 comprising a catalyst library is supplied to the plurality of microreactors 600. Likewise, a first adsorbent array 700 comprising a plurality of adsorbent-containing regions is supplied to the plurality of microseparators 900. The material array 100, and the adsorbent array 700 are then each releasably engaged with and incorporated into the plurality of microreactors 600 and the plurality of microseparators 900, respectively. One or more reactants for the reaction of interest are simultaneously supplied from the fluid distribution system 480 to the plurality of microreactors 600, and allowed to contact each of the different candidate catalysts under reaction conditions effective (or intended to be effective) for the chemical reaction of interest. A resulting reactor effluent stream is discharged simultaneously from each of the plurality of microreactors, cooled if necessary, and then supplied to the plurality of microseparators 900. One or more components (e.g., reaction products) of each of the reactor effluent streams are selectively adsorbed simultaneously onto the addressable regions of the adsorbent array 700, and the separated reactor effluent streams are subsequently simultaneously discharged from the plurality of microseparators. Following reaction and separation: (1) the first adsorbent array 700 is disengaged from and removed from the microseparators 900, and then transported, preferably automatically, to the detection system 1000; and (if desired to change catalyst libraries) simultaneous therewith, (2) the first catalyst-containing material array 100 is disengaged from and removed from the microreactors 600. A second catalyst library on a second material array 100' and a second adsorbent array 700' can then be supplied to the chemical processing microsystem 10 and the afore described steps can be repeated with these arrays 100', 700'. The first adsorbate-containing adsorbent array 700 can be characterized in the detection system 1000 while the second library of catalyst material 100' is being screened, or, if desired, at a later time and/or at a remote location.

Further aspects of the material evaluation system 1, as well as subsystems thereof and operational aspects thereof, are described below.

Candidate Materials

Each of the candidate materials being screened for a capability to enhance a chemical process of interest can be an element, a compound or a composition comprising a plurality of elements and/or compounds. The candidate material can be in a gaseous, liquid or solid phase. Solid-phase candidate materials are preferred for some applications. The particular elements, compounds or compositions to be included in a library of candidate materials will depend upon the particulars of the chemical process being investigated. As noted above, however, the particular chemical process being investigated is not critical, and can include chemical reactions and chemical separations among others.

The chemical process is preferably a chemical reaction, which for purposes hereof, means a process in which at least one covalent bond of a molecule or compound is formed or broken. As such, immunoreactions in which immunoaffinity is based solely on hydrogen bonding or other forces—while chemical processes—are not considered to be chemical reactions. In general, the candidate materials of this invention catalyze reactions that include activation of, breaking and/or formation of H—Si, H—H, H—N, H—O, H—P, H—S, C—H, C—C, C=C, C≡C, C-halogen, C—N, C—O, C—S, C—P, C—B and C—Si bonds among others. Exemplary chemical reactions for which reaction-enhancing materials may be identified according to the present invention include, without limitation, oxidation, reduction, hydrogenation, dehydrogenation (including transfer hydrogenation), hydration, dehydration, hydrosilylation, hydrocyanation, hydroformylation (including reductive hydroformylation), carbonylation, hydrocarbonylation, amidocarbonylation, hydrocarboxylation, hydroesterification, hydroamination, hetero-cross-coupling reaction, isomerization (including carbon-carbon double bond isomerization), dimerization, trimerization, polymerization, co-oligomerization (e.g. CO/alkene, CO/alkyne), co-polymerization (e.g. CO/alkene, CO/alkyne), insertion reaction, aziridation, metathesis (including olefin metathesis), carbon-hydrogen activation, cross coupling, Friedel-Crafts acylation and alkylation, Diels-Alder reactions, C—C coupling, Heck reactions, arylations, Fries rearrangement, vinylation, acetoxylation, aldol-type condensations, aminations, reductive aminations, epoxidations, hydrodechlorinations, hydrodesulfurations and Fischer-Tropsch reactions, asymmetric versions of any of the aforementioned reactions, and combinations of any of the aforementioned reactions in a complex reaction sequence of consecutive reactions. For chemical reactions, the candidate materials can be generally classified as those materials which are chemically altered or consumed during the course of the reaction (e.g., co-reactant materials, cataloreactants) and those materials which are not chemically altered or consumed during the course of the reaction (e.g., catalysts, selective blocking moieties). In preferred applications, the candidate materials are catalysts. As used herein, the term catalyst is intended to include a material that enhances the reaction rate of a chemical reaction of interest or that allows a chemical reaction of interest to proceed where such reaction would not substantially proceed in the absence of the catalyst.

The candidate materials preferably comprise elements or compounds selected from the group consisting of inorganic materials, metal-ligands and non-biological organic materials. In some applications, the candidate materials will consist essentially of inorganic materials, consist essentially of metal-ligand materials, or consist essentially of non-biological organic materials. Moreover, in some applications, the candidate materials will be compositions comprising mixtures of inorganic materials, metal-ligand materials, and/or non-biological organic materials in the various possible combinations.

Inorganic materials include elements (including carbon in its atomic or molecular forms), compounds that do not include covalent carbon-carbon bonds (but which could include carbon covalently bonded to other elements, e.g., $CO_2$), and compositions including elements and/or such compounds. Inorganic candidate materials that could be investigated according to the approaches described herein include, for example: noble metals such as Au, Ag, Pt, Ru, Rh, Pd, Ag, Os and Ir; transition metals such as Ti, V, Cr, Mn, Fe, Co, Ni, Cu, Zn, Y, Zr, Nb, Mo, Ta, W and Re; rare-earth metals such as La, Ce, Pr, Nd, Sm, Eu, Tb, Th and U; alloys of noble metals, transition metals and/or rare-earth metals; metal oxides such as CuO, NiO and $Co_3O_4$; noble-metal-doped metal oxides such as noble-metal-doped CuO, NiO and $Co_3O_4$; multi-metal oxides such as binary oxides of Cu—Cr, Cu—Mn, Cr—Mn, Ni—Cr, Ni—Mn, Ni—Cu, Ni—Mo, Cu—Mo, Ni—Co, Co—Mo, Ni—Fe—Fe—Mo, Cu—Fe, Mn—Ag, Mn—Sn, Ag—Sn, Cu—Ag, Cu—V, Ag—V, Cu—V, Ni—V, Bi—Mo, Bi—V, Mo—V, V—Zr, V—Ti, Zr—Ti, V—Nb, Nb—Mo, V—P, P—Mo, Ni—P, P—Cu, Co—P, Co—Fe, P—Fe, Mg—V, Mg—Sn, V—Sn, K—Ti, K—Bi, Ti—Bi, Cr—Sb, Cr—V, Sb—V, Bi—Mo, Bi—Nb, K—Cr, K—Al, Al—Cr, Zn—Cu, Zn—Al, Cu—Al, La—Cr, La—Zr, Cr—Zr, La—Mo, Mo—Zr, La—W, W—Zr, Mo—W, W—V, Cu—W, Bi—W, Fe—Sb, Fe—V and Ni—Ta, Ni—Nb and Ta—Nb, and such as ternary oxides of Cu—Cr—Mn, Ni—Cr—Mn, Ni—Cu—Mo, Ni—Co—Mo, Ni—Fe—Mo, Cu—Fe—Mo, Mn—Ag—Sn, Cu—Ag—V, Cu—Ni—V, Bi—Mo—V, V—Zr—Ti, V—Nb—Mo, V—P—Mo, Ni—P—Cu, Co—P—Fe, Mg—V—Sn, K—Ti—Bi, Cr—Sb—V, Bi—Mo—Nb, K—Cr—Al, Zn—Cu—Al, La—Cr—Zr, La—Mo—Zr, La—W—Zr, Mo—W—V, Cu—Mo—W, Bi—Mo—W, Bi—V—W, Fe—Sb—V and Ni—Ta—Nb; metal carbides such as PdC; metal sulfates, metal sulfides, metal chlorides, metal acetates, polyoxometallates (POM); metal phosphates such as vanadylpyrophosphates (VPO); Bronstead acids such as HF; Lewis Acids such as $AlCl_3$; and mixtures of any of the aforementioned inorganic materials, among others. Exemplary inorganic material libraries could include, for example, a triangular-shaped array of ternary metal oxides (e.g. such as oxides of the ternary metal partners described above) with single metal oxide compounds at each corners, binary metal oxide compositions along each of the sides with varying ratios of constituents, and ternary metal oxide compositions in the interior regions of the triangular array with varying ratios of constituents. Libraries of inorganic candidate materials can be prepared, for example, according to the methods disclosed in U.S. Pat. No. 5,776,359 to Schultz et al.

Metal-ligands comprise a central metal atom or ion surrounded by, associated with and/or bonded to other atoms, ions, molecules or compounds—collectively referred to as "ligands"—typically through a carbon (to form, e.g., an organometallic), nitrogen, phosphorous, sulfur or oxygen atom and/or one or more linker moieties. The one or more ligands typically bind to one or more metal center and/or remain associated therewith, and by such association, modify the shape, electronic and/or chemical properties of the active metal center(s) of the metal-ligand complex. The ligands can be organic (e.g., $\eta^1$-aryl, alkenyl, alkynyl, cyclopentadienyl, CO, alkylidene, carbene) or inorganic (e.g., $Br^-$, $Cl^-$, $OH^-$, $NO^{2-}$, etc.), and can be charged or neutral. The ligand can be an ancilliary ligand, which remains associated with the metal center(s) as an integral constituent of the catalyst or compound, or can be a leaving group ligand, which may be replaced with an ancillary ligand or an activator component. Exemplary metals/metal ions include ions derived from, for example, simple salts (e.g., $AlCl_3$, $NiCl_2$, etc.), complex or mixed salts comprising both organic and inorganic ligands (e.g., [($\eta5$-$C_5Me_5$)$IrCl_2]_2$, etc.) and metal complexes (e.g., $Gd(NTA)_2$, CuEDTA, etc.), and can generally include, for example, main group metal ions, transition metal ions, lanthanide ions, etc.

Libraries of metal-ligand candidate materials can be prepared, for example, according to the methods disclosed in PCT Patent Application WO 98/03521 of Weinberg et al. Briefly, a desired ligand can be combined with a metal atom, ion, compound or other metal precursor compound. In many applications, the ligands will be combined with such a metal compound or precursor and the product of such combination is not determined, if a product forms. For example, the ligand may be added to a reaction vessel at the same time as the metal or metal precursor compound along with the reactants. The metal precursor compounds may be characterized by the general formula $M(L)_n$ (also referred to as $ML_n$ or M—$L_n$) where M is a metal and can include metals selected from the group consisting of Groups 5, 6, 7, 8, 9 and 10 of the Periodic Table of Elements. In some embodiments, M can be selected from the group consisting of Ni, Pd, Fe, Pt, Ru, Rh, Co and Ir. L is a ligand and can be selected from the group consisting of halide, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, hydroxy, boryl, silyl, hydrido, thio, seleno, phosphino, amino, and combinations thereof, among others. When L is a charged ligand, L can be selected from the group consisting of hydrogen, halogens, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof. When L is a neutral ligand, L can be selected from the group consisting of carbon monoxide, isocyanide, nitrous oxide, $PA_3$,$NA_3$, $OA_2$, $SA_2$, $SeA_2$, and combinations thereof, wherein each A is independently selected from a group consisting of alkyl, substituted alkyl, heteroalkyl, cycloalkyl, substituted cycloalkyl, heterocycloalkyl, substituted heterocycloalkyl, aryl, substituted aryl, heteroaryl, substituted heteroaryl, alkoxy, aryloxy, silyl, and amino. Specific examples of suitable metal precursor compounds include $Pd(dba)_2$ (dba=dibenzylydieneacteone), $Pd_2(dba)_3$, $Pd(OAc)_2$(Ac=acetate), $PdCl_2$, $Pd(TFA)_2$, (TFA=trifluoroacetate), $(CH_3CN)_2PdCl_2$, and the like. In this context, the ligand to metal precursor compound ratio is in the range of about 0.01:1 to about 100:1, more preferably in the range of about 0.5:1 to about 20:1. The metal atom, ion or metal precursor may be supported or not. Supports may be organic or inorganic. Similar to the ligands, the support may be an L. In other embodiments, the support will not form part of the metal precursor and suitable supports include silicas, aluminas, zeolites, polyethyleneglycols, polystyrenes, polyesters, polyamides, peptides and the like. Specific examples of Pd supported metals include Pd/C, $Pd/SiO_2$, $Pd/CaCO_3$, $Pd/BaCO_3$, Pd/aluminate, Pd/aluminum oxide, Pd/polystyrene, although any of the metals listed above could replace Pd in this list, e.g., Ni/C, etc. In other applications, the ligand will be mixed with a suitable metal precursor compound prior to or simultaneous with allowing the mixture to be contacted to the reactants. When the ligand is mixed with the metal precursor compound, a metal-ligand complex may be formed, which may be employed as a candidate material.

Non-biological organic materials include organic materials other than biological materials. Organic materials are considered to include compounds having covalent carbon-carbon bonds. Biological materials are considered to include nucleic acid polymers (e.g., DNA, RNA) amino acid polymers (e.g., enzymes) and small organic compounds (e.g., steroids, hormones) where the small organic compounds have biological activity, especially biological activity for humans or commercially significant animals such as pets and livestock, and where the small organic compounds are used primarily for therapeutic or diagnostic purposes. While biological materials are of immense commercial interest with respect to pharmaceutical and biotechnological applications, a large number of commercially significant applications involve chemical processes that are enhanced by other than biological materials. Moreover, while fundamental screening approaches for many pharmaceutical and biological activities are known or readily adapted from known approaches, screening approaches for non-biological materials have not heretofore been widely investigated and reported. Although the candidate materials being screened are preferably not, themselves, biological organic materials, the candidate materials of the invention (e.g., inorganic materials) can be employed to enhance reactions directed to producing a biological organic material as the product of a chemical reaction (e.g., materials that enhance chemical-based, non-enyzmatic DNA synthesis, or materials that enhance a synthetic, non-enyzmatic route to a particular hormone or steroid).

In preferred applications, the candidate materials are catalysts being screened for catalytic activity and/or for catalytic selectivity for a chemical reaction of interest. The candidate catalysts can be homogeneous catalysts or heterogeneous catalysts. For homogeneous catalysis, the candidate materials are preferably solids or liquids which are soluble or miscible in the reaction medium under the reaction conditions, but can also include gasses. For heterogeneous catalysis, the candidate materials are preferably solids. In general, homogeneous candidate catalyst materials and heterogeneous candidate catalyst materials can include organic, inorganic and metal-ligand catalysts such as are described above. Exemplary reactions for which a homogeneous catalyst may be investigated pursuant to the present invention, as well as known homogeneous catalysts for such reactions are shown in Table 1A. Exemplary reactions for which a heterogeneous catalyst may be investigated pursuant to the present invention, as well as known heterogeneous catalysts for such reactions are shown in Table 1B. The library of candidate catalysts being screened can be variations in the structure or composition of known catalysts or can be structurally unrelated thereto.

TABLE 1A

Exemplary Homogeneous Catalytic Reactions

| Reaction Class | Known Catalyst |
|---|---|
| assymetric C—C double bond isomerization | Ru—, Rh— ligand (e.g., phosphine) |
| Suzuki biaryl cross-coupling | Pd— ligand (e.g., phosphine) |
| hydroformylation | Co—, Rh— ligand (e.g., phosphine, phosphite) |
| hydrocarboxylation | Mo—, Pd—, Rh—, Co—, ligand (e.g., phosphine) |
| Heck reaction | Pd— ligand (e.g., phosphine) |
| hydrocyanation | Ni— ligand (e.g., phosphite) |
| assymetric hydrogenation | Ru—, Rh— ligand (e.g., phosphine) |
| Friedel-Crafts reaction | HF, AlCl$_3$ |
| olefin polymerization | Zr—, Ti—, Hf— ligand (e.g. cyclopentadiene) Ni—, Pd— ligand (e.g., bis-imine) |
| olefin metathesis | Ru—, Mo— ligand (e.g., N—, P— based) |
| methanol carbonylation | Ir, Rh with halides (e.g., MeI, HI) |
| epoxide ring opening | Cu— ligand (e.g., alkoxide, amide, amine) |

TABLE IB

Exemplary Heterogeneous Catalytic Reactions

| Reactant(s) | Product | Known Catalyst |
|---|---|---|
| ethylene + acetic acid | vinyl acetate | Pd—Au |
| ethylene glycol | glyoxal | Cu |
| ethylene | ethyleneoxide | Ag |
| methanol | formaldehyde | Ag |
| butene dimerization | octene | Ni |
| HCl | Cl2 | Cu—Fe—Cl, Cu—Cr—O |
| propylene | acrolein | Bi—Mo—O |
| acrolein | acrylic acid | Mo—V—O(+Cu—Mo—O + W—O) |
| methacrolein | methacrylic acid | POM |
| o-xylene | Phthalic anhydride | V/TiO2 |
| butane | maleic anhydride | VPO |
| toluene | benzonitrile | V—Sb—O, Fe—Sb—O |
| ethylbenzene | styrene(non-ODH) | K—Fe—O |
| ethylbenzene | styrene(ODH) | K—Bi—O/TiO2 |
| propane | propylene | K—Cr—O/Al2O3 |
| vinyl cyclohexene | styrene | Cu/zeolite |
| cyclohexanol | cyclohexanone | Cu/SiO2 |
| cyclohexene | benzene | NM/support |
| cyclohexylamine | aniline | NM/support |
| side chain aromatics | aromatic acids | Co—Mn—Zr-acetates |
| ethylene | acetaldehyde | Pd—Cu, Pd—Au |
| acetaldehyde | acetic acid | Mn-acetate |
| propylene | propylene oxide | Ti/silicalite |

TABLE IB-continued

Exemplary Heterogeneous Catalytic Reactions

| Reactant(s) | Product | Known Catalyst |
|---|---|---|
| butadiene | vinyl oxirane | Ag |
| nitrobenzene | aniline | Cu/SiO2 |
| beta-picoline | nicotinic acid | V—Mo/Ti—Zr—O |
| maleic anhydride | gamma-butyrolactone, tetrahydrofurane | Cu—Zn—O, Cu—Cr—O |
| propane | acrylic acid | V—Mo—Nb—O |
| propane | acryl nitrile | |
| benzene | phenol | Fe—Ga/zeolite |
| syngas | methanol | Cu—Zn/Al2O3 |
| syngas | methane | Ni |
| syngas | fuel hydrocarbons | Fe, Co |
| H2 + N2 | ammonia | Fe |
| CH4 + H2O | H2 + CO | Ni |
| DeNOx | | V/TiO2 |

Supply of Candidate Materials to Microreactors

Two or more, and preferably four or more different candidate materials being screened for their capability to enhance a chemical process are supplied, preferably simultaneously, to a plurality of microreactors, such that each of the candidate materials is individually resident in a separate microreactor. Specifically, a first candidate material is supplied to a first microreactor and, preferably simultaneously therewith, a second candidate material is supplied to a second microreactor. If additional candidate materials are to be screened in additional microreactors, then each additional candidate material is preferably supplied simultaneously to respective individual microreactors, to form an array of microreactors, each of which comprises a candidate material to be screened. While the simultaneous, parallel loading of different candidate materials into the microreactors is preferred, serial loading, including automated serial loading, of the candidate materials may be appropriate for chemical processing microsystems having a moderate number of microreactors (e.g., not more than about 100). In any case, particular candidate materials are considered to be different from other candidate materials if they comprise different elements or compounds or compositions. Candidate materials having the same composition can also be considered different from each other if they have measurably different physical properties (e.g., thickness, crystalline structure, active surface area) or otherwise differ in form, and these differences impart different process-enhancing activity (e.g., catalytic activity) to the two candidate materials.

As noted, different candidate materials are loaded into separate, dedicated microreactors. Typically, however, not all of the microreactors are supplied with a candidate material. As discussed below in connection with the microreactors, some of the microreactors can, instead, comprise a control material. For example, one or more of the microreactors can be supplied with a positive control (e.g., a known catalyst), left blank (without any additional candidate material supplied) or supplied with a negative control material.

Solid-phase candidate materials are preferably supplied to a plurality of microreactors as an array of candidate materials. An array of candidate materials generally comprises a substrate and two or more different candidate materials, and preferably four or more different candidate materials at separate portions of the substrate. The candidate materials are spatially separated, preferably at an exposed surface of the substrate, such that the array of materials can be integrated with the plurality of microreactors to include different candidate materials within different microreactors. Moreover, the different candidate materials are also preferably separately addressable, for example, for analytical characterization thereof. The two or more different candidate materials are therefore preferably located at discrete, non-contiguous, individually addressable regions of the substrate, with the regions being spaced to accommodate inclusion into a plurality of microreactors. The different candidate materials may, nonetheless, also be contiguous with each other (e.g. as in a continuous gradient of different material compositions).

The substrate is any material having a rigid or semi-rigid surface on which the candidate material can be formed or deposited or to which the candidate material can be linked. The substrate can be of any suitable material, and preferably consists essentially of materials that are inert with respect to the chemical process of interest, and except where desired otherwise, with respect to the candidate materials being screened. Certain materials will, therefore, be less desirably employed as a substrate material for certain reaction process conditions (e.g., high temperatures—especially temperatures greater than about 100° C.—or high pressures) and/or for certain reaction mechanisms. The substrate material is also preferably selected for suitability in connection with microfabrication techniques, such as selective etching (e.g., chemical etching in a liquid or gaseous phase, plasma-assisted etching, and other etching techniques) photolithography, and other techniques known or later-developed in the art. Silicon, including polycrystalline silicon, single-crystal silicon, sputtered silicon, and silica ($SiO_2$) in any of its forms (quartz, glass, etc.) are preferred substrate materials. Other known materials (e.g., silicon nitride, silicon carbide, metal oxides (e.g., alumina), mixed metal oxides, metal halides (e.g., magnesium chloride), minerals, zeolites, and ceramics) may also be suitable for a substrate material. Organic and inorganic polymers may also be suitably employed in some applications of the invention.

As to form, the substrate can, but does not necessarily, have at least one substantially flat, substantially planar surface, and is preferably, but not necessarily, a substantially planar substrate such as a wafer. The surface of the substrate can be divided into physically separate regions and can have, for example, dimples, wells, raised regions, etched trenches, or the like formed in the surface. In still other embodiments, small beads or pellets may be the substrate, and such beads or pellets may be included in an array, for example, for example, placing the beads within dimples, wells or within or upon other regions of the substrate's surface. Frits can be used to hold such beads or pellets in place. In yet another embodiment, the substrate can be a porous material. The substrate can, and is preferably, passive—having an essential absence of any active microcomponents such as valves, pumps, active heating elements, active mixing elements. The substrate also preferably has an essential absence of passive microcomponents such as microfluidic channels or apertures used for fluid distribution, heat-transfer elements, mass-transfer elements (e.g., membranes), etc., or combinations thereof. In some embodiments, however, the substrate can include such active microcomponents or such passive microcomponents. In a preferred embodiment, the substrate has a substantially flat upper surface with a plurality of substantially coplanar indentations or wells of sufficient depth to allow a quantity of candidate material to be deposited, formed or contained therein. The overall size and/or shape of the substrate is not limiting to the invention. The size can be chosen, however, to be compatible with commercial availability, existing fabrication techniques (e.g., silicon wafer availability and/or fabrication), and/or analytical measurement techniques. Generally, the substrate will be sized to be portable by humans and/or to be manipulated by automated substrate-handling devices. Hence, two inch and three inch wafers are suitably employed. The choice of an appropriate substrate material and/or form for certain applications will be apparent to those of skill in the art based on the guidance provided herein.

The candidate material is preferably, in most cases, immobilized with respect to the substrate, and once loaded into a microreactor, the candidate material and/or the substrate are preferably immobilized with respect to the microreactor. The immobilized material offers a controlled geometry, such that fluid flow past, over, around or through the candidate material and/or the substrate will not vary the process-enhancing effect thereof during any particular experiment. The configuration of the candidate material with respect to the substrate and/or the microreactor can be of any design which allows for one or more reactants to contact the candidate material during the chemical reaction or other chemical process. Hence, it can be appreciated that the exact configuration of the candidate materials and the substrate are not limiting to the invention. Typical configurations, such as those discussed below, generally allow for flow past and around a candidate material formed on a surface of a reaction cavity, for unidirectional flow of reactants through a porous substrate or through a bed of beads, or for flow of reactants into and out of a well comprising a porous or non-porous substrate.

Figure 2:
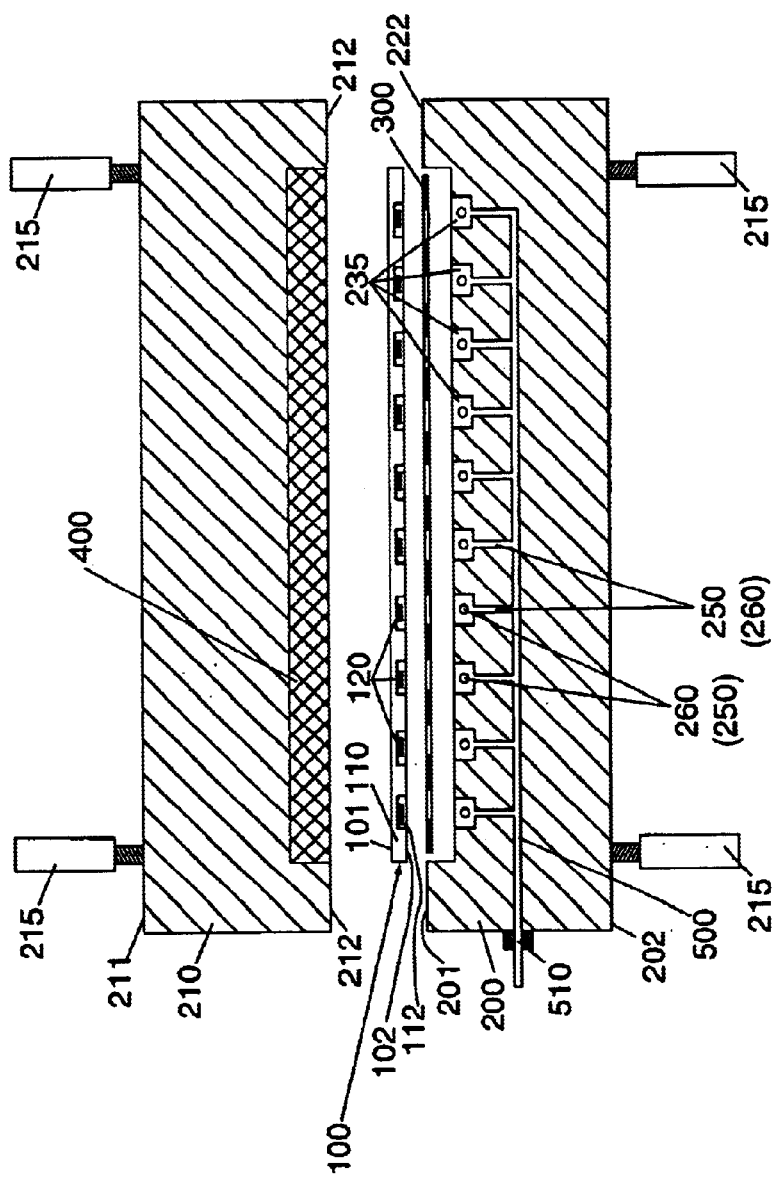
FIG. 2 is a cross-sectional side view of an exemplary embodiment of a chemical processing microsystem comprising an array of solid-phase candidate materials.

An exemplary embodiment of a chemical processing microsystem adapted for use with an array of solid-phase candidate materials is shown schematically in FIG. 2. The array 100 comprises a substrate 110 having one or more exposed surfaces 112 and having a plurality of candidate materials 120 on the exposed surfaces 112 of the substrate 110, or on various portions thereof. The array can be integrally, and releasably positioned between housing block 210 and reactor block 200, by bringing opposing surfaces 212 and 201 of the housing block 210 and reactor block 200, respectively, into contact with each other, such that the array 100, the exposed surface 112, and candidate material 120, taken together with the plurality of wells 235 formed in the reactor block 200, define a plurality of microreactors. Each microreactor comprises a surface defining a reaction cavity and at least a portion of a material-containing region of the substrate 110 within the reaction cavity. Reactants can be supplied to the microreactors through inlet ports 250 (260), and the reactor effluent can be discharged from the microreactors through outlet ports 260 (250). A seal such as a gasket 300 having a plurality of apertures arranged to correspond with the arrangement of the plurality of wells 235 and of the arrangement of candidate materials 120 may be situated between the array 100 and the reactor block 200 to independently seal each microreactor once the housing block 210 and reactor block 200 are brought together. The housing block 210 and reactor block 200 may be brought into contact with each other (to engage the array 100) through parallel threaded-connectors 215 (e.g., bolts), through hydraulic means, through spring-pressure or through other suitable compressive-force fastener. Engaging and/or releasing the array of materials 100 from the microreactors 600, and specifically, from the housing block 210 and reactor block 200, may be effected as a manual or an automated operation.

The array of materials preferably comprises one or more films at an exposed surface of the substrate. The film can have an average thickness ranging from about 0.01 $\mu$m to about 100 μm, and more preferably ranging from about 0.05 μm to about 10 μm, and most preferably from about 0.1 μm to about 1 μm. With reference to FIG. 3, a film can be formed on the exposed surface of the substrate—with different materials at different discrete regions thereof (e.g., FIG. 3A), or with different materials contiguous to each other (e.g., FIG. 3B). In alternative configurations, the exposed surface of a given film can be (1) in a plane that is substantially parallel to, and external to (that is, elevated relative to) the exposed substrate surface 112 (e.g., FIG. 3A, FIG. 3B), (2) substantially coplanar with the exposed substrate surface 112 (e.g., FIG. 3C) or (3) in a plane that is substantially parallel to, and internal to (that is, depressed relative to) the exposed substrate surface 112 (e.g., FIG. 3D). For correlation purposes (with FIG. 2, for example), the exposed substrate surface 112 on which the film resides may or may not be the same surface as the upper-most surface 102 of the material-containing array 100.

A film of a material can be formed, for example, by depositing the material or material precursors (e.g., individual components of a composition) onto an exposed surface of the substrate, and where appropriate, treating to react the deposited material precursors with each other. Such post-deposition treatment can be completed before or after loading the candidate materials into the microreactors. Suitable methods for depositing a film of materials include physical vapor deposition (e.g., evaporation, sputtering, ion plating), chemical vapor deposition, plasma-assisted chemical vapor deposition, electrodeposition, electrochemical deposition, coating techniques (e.g., spray drying, spray coating, pyrolysis), and solution-based techniques (e.g., sol-gel, impregnation, precipitation), among others. The film can also be formed by in situ growth at a substrate surface, by diffusion of the material into a substrate surface, or by conversion of the substrate material (e.g., thermal oxidation ). Such approaches and others are discussed in detail in Bunshah, *Handbook of Deposition Technologies for Films and Coatings*, $2^{nd}$ Ed., Noyes Publications (1994), and references cited therein. The candidate materials may be applied in discrete, individually addressable regions using mechanical or chemical masking approaches. For example, mechanical masks or shutters can be used in connection with many of the aforementioned deposition techniques to create an array of films in a desired arrangement. Distinct regions of candidate materials may also be formed using film-formation approaches that are or can be controlled to be region-selective—without masking. Spray drying and electrochemical deposition approaches are exemplary region-selective approaches. Different candidate materials may alternatively be applied contiguous to each other. The array can comprise, for example, a contiguous composition gradient of two or more components. Contiguous natural composition gradients can be formed, for example, by multiple-target vapor deposition approaches. See, e.g., Hanak et al., *Optimization Studies of Materials in Hydrogenated Amorphous Silicon Solar Cells*, Photovoltaic Solar Energy Conference, Berlin (1979), and van Dover et al., *Discovery of a Useful Thin-Film Dielectric Using a Composition-Spread Approach*, Nature, Vol. 392, No. 12, pp. 162–164 (1998). Contiguous controlled gradients can be formed, for example, by orchestrated (e.g., programmed) masking or shuttering approaches with multi-target deposition, such as those disclosed in copending U.S. patent application Ser. No. 09/237,502 filed Jan. 26, 1999 by Wang et al.

Preferred approaches for forming an array of candidate materials include vapor deposition techniques disclosed in U.S. Pat. No. 5,776,359 to Schultz et al., sol-gel solution-based techniques disclosed in commonly-owned co-pending U.S. patent application Ser. No. 09/156,827, filed Jan. 18, 1998 by Giaquinta et al., electrochemical deposition techniques disclosed in commonly-owned co-pending U.S. patent application Ser. No. 09/119,187, filed Jul. 20, 1998 by Warren et al., and in situ impregnation techniques for creating arrays of supported catalysts as disclosed in commonly-owned co-pending U.S. patent application Ser. No. 09/516,669, filed Mar. 1, 2000 by Lugmair et al., each of which is incorporated by reference for all purposes. The combinatorial library embodied in the array of candidate materials is preferably designed with the assistance of library design software such as LIBRARY STUDIO™ software (Symyx Technologies, Inc., Santa Clara, Calif.). Preparation of the arrays can be advantageously effected using automated liquid handling robots (e.g., CAVRO Scientific Instruments, Inc.), under control of software such as IMPRESSIONIS™ software (Symyx Technologies, Inc.).

The amount of an individual candidate material deposited as a film (or otherwise included) on a particular portion of the array is not limiting to the invention. The required amount will vary depending upon the required surface area of the film and the required thickness of the film, each of which will, in turn, vary depending upon the chemical process of interest, the geometry of the microreactor, and the required residence time or contact time of reactants in the microreactor, among other factors. In general, the amount of an individual candidate material is typically not more than about 25 mg, preferably not more than about 10 mg, and can be not more than about 7 mg, not more than about 5 mg, not more than about 3 mg and not more than about 1 mg. In preferred embodiments, the amount of an individual candidate material can range from about 0.1 μg to about 100 mg, preferably from about 1 μg to about 10 mg, more preferably from about 10 μg to about 10 mg and most preferably from about 100 μg to about 1 mg.

Figure 3A:
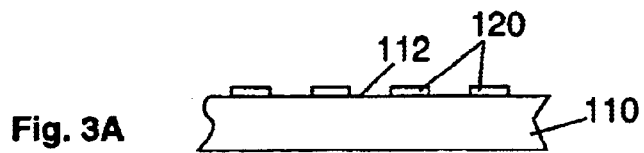
FIG. 3A through FIG. 3H are partial cross-sectional side views showing exemplary configurations of arrays of candidate materials. As shown, the candidate materials are formed as one or more films on various exposed surfaces of a substrate (FIG. 3A through FIG. 3D), are included within an array linked to a porous substrate (FIG. 3E, FIG. 3F) or linked to microparticles (FIG. 3G, FIG. 3H), or are included in the array as bulk candidate materials (FIG. 3G, FIG. 3H).
Figure 3B:
Figure 3C:
Figure 3D:
Figure 3E:
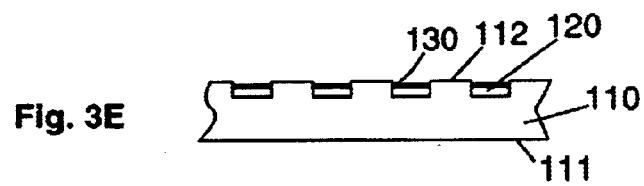
Figure 3F:
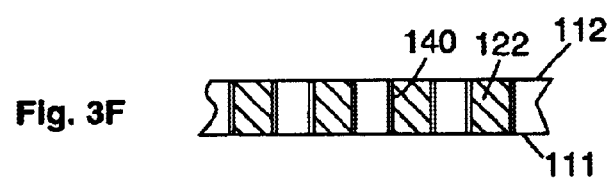
Figure 3G:
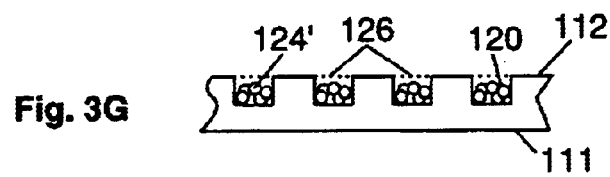
Figure 3H:
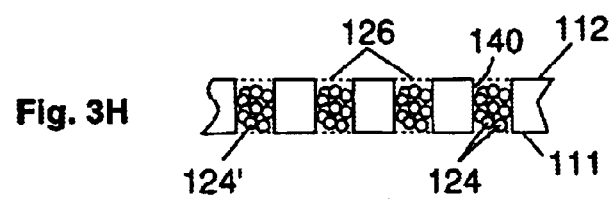

While an array of one or more films is advantageously employed in connection with the present invention, other array configurations can also be employed to supply the two or more solid-phase candidate materials to a plurality of microreactors. The array can comprise, for example, the candidate materials loaded into the microreactors in bulk form, or as bonded to or linked to porous materials or to microparticles. With reference again to FIG. 3, the array can comprise, for example, a substrate 110 having a plurality of wells 130 formed in an exposed surface 112 of the substrate (e.g., FIG. 3E, FIG. 3G) or having a plurality of apertures 140 extending between first and second substantially parallel surfaces 111, 112 of the substrate 110 (e.g., FIG. 3F, FIG. 3H). Such a well 130 or an aperture 140 can comprise a porous material 122 (e.g., FIG. 3E, FIG. 3F) to which a particular candidate material is bonded, preferably covalently bonded. Exemplary porous materials include quartz, glass or alumina, etched microchannels or glass plates, diatomaceous earth, etc. As another alternative, a well 130 or an aperture 140 can comprise microparticles 124, typically referred to in the art as "latex particles" or "beads", to which a particular candidate material is bonded, and preferably covalently bonded (FIG. 3G, FIG. 3H) or, alternatively, bulk candidate materials 124' (FIG. 3G, FIG. 3H). The beads can be held within the well 130 or aperture 140 by frits 126. Exemplary microparticles include polystyrene particles, controlled pore glass (CPG), etc.

Liquid and/or gaseous phase candidate materials may also be supplied to the plurality of microreactors in an array format. For liquids, an array of wells with different liquid candidate materials in each well can be employed. For gasses, an array of different time-release materials that release the candidate gas of interest over time can be employed. Alternatively, either liquids (e.g., soluble candidate materials) or gasses can be adsorbed onto inorganic or organic substrates to form a "solid-phase" form thereof (e.g., as a useful heterogeneous catalyst). It may be preferable, however, to supply different candidate liquid and/or gaseous phase candidate materials to the plurality of microreactors using a fluid distribution manifold, as described below in connection with the supply of reactants to the plurality of microreactors.

The number of candidate materials to be screened in any cycle of screening is not narrowly critical, and can range, for example, from two to about a million, and even more, ultimately depending on the number of microreactors available for the screening. More specifically, the number of different candidate materials to be supplied to different microreactors is at least 2, preferably at least 5, more preferably at least 10, still more preferably at least 25, even more preferably at least 50, yet more preferably at least 100, and most preferably at least 250. Present microscale and nanoscale fabrication techniques can be used, however, to prepare arrays having an even greater number of different candidate materials. For higher throughput operations, for example, the number of different candidate materials can be at least about 1000, more preferably at least about 10,000, even more preferably at least about 100,000, and most preferably at least about 1,000,000 or more. The fabrication of arrays comprising very large numbers of different candidate materials is enabled by fabrication techniques known in the integrated circuit arts. See, for example, S. M. Sze, *Semiconductor Sensors*, Chap. 2, pp. 17–96, John Wiley & Sons, Inc. (1994). Such approaches have been adapted in other aspects of catalyst research. See, for example, Johansson et al., *Nanofabrication of Model Catalysts and Simulations of their Reaction Kinetics*, J. Vac. Sci. Technol., 17:1 (January/February 1999).

If the two or more candidate materials are to be deposited on distinct, individually addressable regions of the substrate, the separation between adjacent regions can range from about to about 50 $\mu$m to about 1 cm, more preferably from about 100 $\mu$m to about 7 mm, and most preferably from about 1 mm to about 5 mm. The inter-region spacings can be not more than about 1 cm, not more than about 7 mm, not more than about 5 mm, not more than about 4 mm, not more than about 2 mm, not more 1 mm, not more than about 100 $\mu$m, and not more than about 50 $\mu$m. Exemplary inter-regions spacings (center-to-center) based on preferred embodiments of the invention are 4 mm for having 256 addressable regions on a three-inch wafer substrate, and 2 mm for having 1024 addressable regions on a three-inch wafer substrate. As such, the surface density of discrete candidate material regions can range from about 1 region/cm$^2$ to about 200 regions/cm$^2$, more preferably from about 5 regions/cm$^2$ to about 100 regions/cm$^2$, and most preferably from about 10 regions/cm$^2$ to about 50 regions/cm$^2$. The planar density can be at least 1 region/cm$^2$, at least 5 regions/cm$^2$, at least 10 regions/cm$^2$, at least 25 regions/cm$^2$, at 50 regions/cm$^2$, at least 100 regions/cm$^2$, and at least 200 regions/cm$^2$. For some reactions, lower or mid-range densities may be preferred. For other reactions, higher densities may be suitable. Additionally, even higher densities may be achieved as fabrication technology develops to nano-scale applications. As discussed below, the arrangement of the plurality of candidate materials (including separation and relative spatial address) and the plurality of regions should be correlated with the arrangement of microreactors for integration therewith.

In a preferred embodiment, the array of candidate material consists of, or alternatively, consists essentially of, the substrate and two or more different materials at separate portions of the substrate. As used in this context, the phrase "consists essentially of" is intended to exclude other microcomponents such as valves, active mixers, fluid distribution manifolds, etc, without excluding structure whose function is merely to hold a candidate material in a particular position or to confine a candidate material to a particular space. For example, embodiments that include microparticles and frits, if they do not contain other microcomponents such as distribution channels, valves, etc., are still considered to "consist essentially of" the candidate material of interest and the substrate, since the frits and microparticles serve only to confine the candidate material between the frits. The separate portions can be contiguous to each other, or separated by substrate material or other (e.g., insulating) material. Separated regions may be preferred if substantial interdiffusion between contiguous candidate materials is likely and may present erroneous data. The separate portions can be at or above a surface of the substrate or within a well or aperture provided in the substrate.

With reference again to FIG. 1C, a distinct advantage of supplying the plurality of candidate materials as a modular material array 100 is that an entire libraries of candidate materials can be efficiently loaded to the plurality of microreactors, screened therein, and then unloaded therefrom. The microreactors can subsequently be reloaded with other libraries. Hence, in a preferred embodiment, the array of candidate materials is interchangeable with the microreactor mother structure without affecting the structural integrity of other system microcomponents. For example, the array of candidate materials is preferably independent of the structural integrity of each of the following systems (considered independently or collectively): a fluid distribution system, a heat-transfer system, an analytical system, and a mixing system. A plurality of material arrays 100, 100', 100" (FIG. 1C) can be transferred to and/or from the chemical processing microsystem 10 using a material library handling system 5 (FIG. 1C). Such transfer can occur manually (e.g., by hand), semiautomatically (e.g., using a human-controlled robotics) or automatically (e.g., using mechanical, hydraulic, pneumatic, robotic or other automated means). Exemplary systems include wafer-handling equipment known in the integrated-circuit manufacturing arts.

Figure 4A:
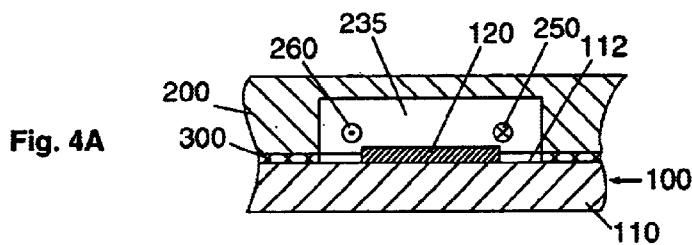
FIG. 4A through FIG. 4E are partial cross-sectional side views showing a number of variations with respect to the geometry with which an array of candidate materials can be integrated with other laminae to form an array of candidate-material loaded microreactors.
Figure 4B:
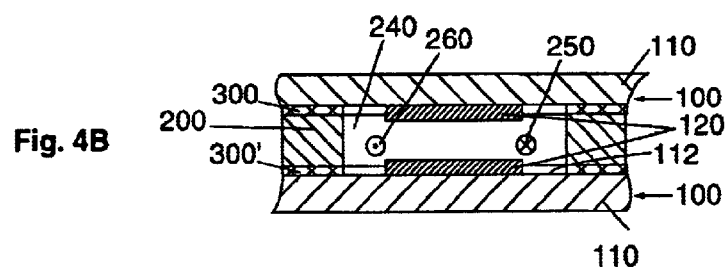
Figure 4C:
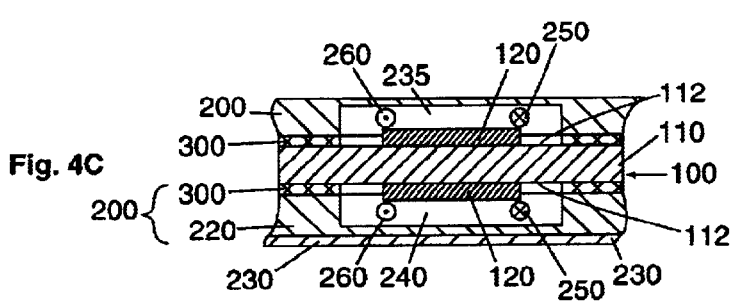
Figure 4D:
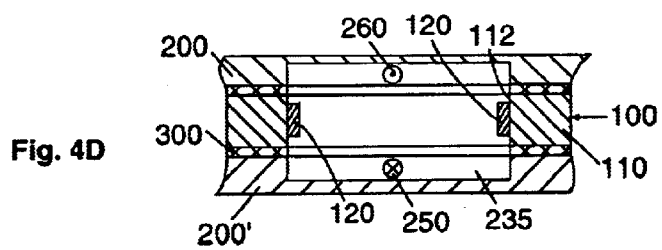
Figure 4E:
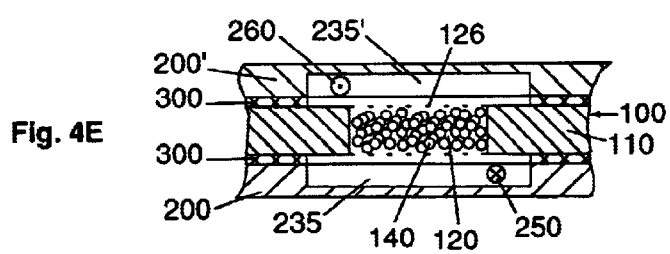
Figure 5:
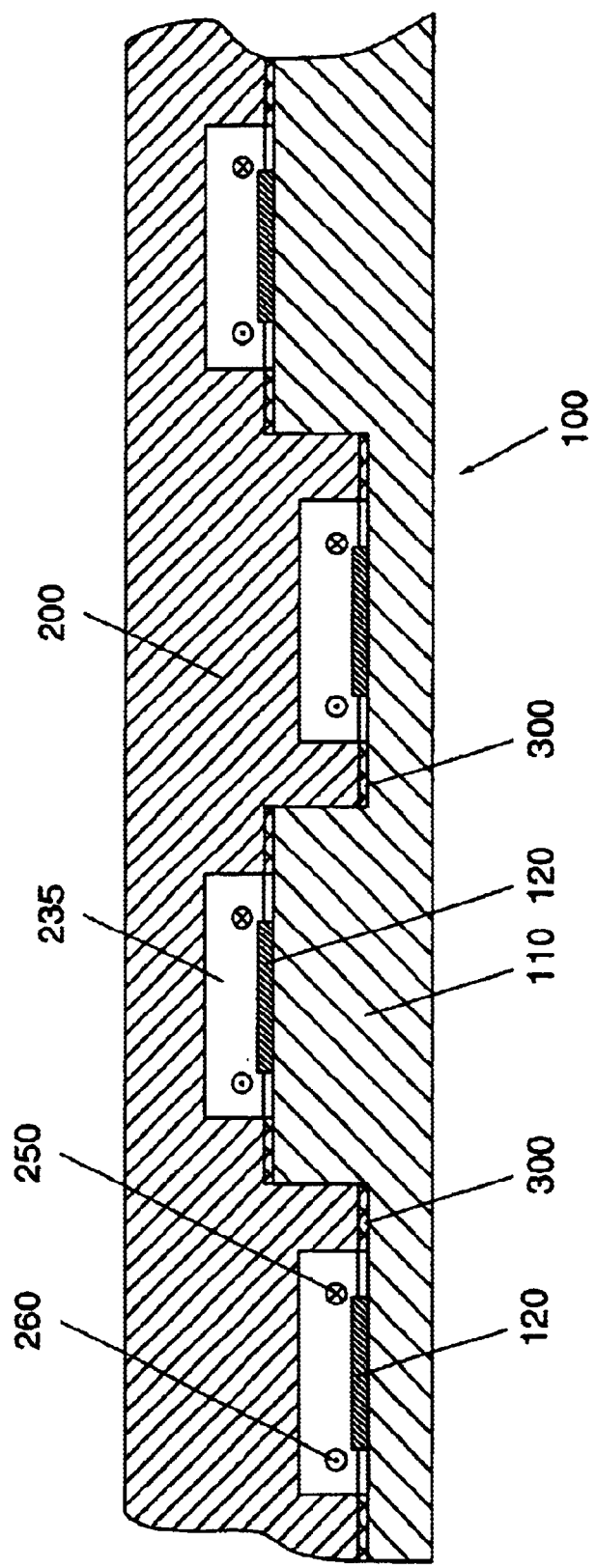
FIG. 5 is a partial cross-sectional side view showing a plurality of non-planar microreactors formed in a plurality of laminae.

A number of variations can be employed with respect to the geometry with which the array of candidate materials is interchangeably integrated with the microreactors. Several exemplary geometries are shown in FIGS. 4 and 5. Each of FIGS. 4A through 4E and FIG. 5 show an individual microreactor as a cut-away view from an array of microreactors. Each of the microreactors of FIGS. 4A through 4E, and FIG. 5 are formed in a plurality of adjacent laminae, with at least one of the laminae being a material-containing array laminate 100, and a reactor block 200 comprising one (e.g., FIG. 4A through 4E, FIG. 5) or more (e.g., FIG. 4C) laminae and having a well 235 (e.g., FIG. 4A, FIG. 4C, FIG. 4D, FIG. 4E, FIG. 5) or an aperture 240 (FIG. 4B). As shown in FIG. 4C, a well-type structure can be formed in a composite reactor block 200 from two adjacent laminae 220, 230 by combining a reactor laminate 220 having an aperture 240 with a capping laminate 230. One or more of the material-containing laminates 100, taken together with the reactor block 200 (or optionally, with laminates 220 and 230), form a microreactor having an interior surface that defines a reaction cavity. Each of the microreactors shown in FIGS. 4A through 4E and FIG. 5 also comprise one or more inlet ports 250 in fluid communication with the reaction cavity for supplying one or more reactants (or co-reactant candidate material) thereto, and preferably, one or more outlet ports 260 in fluid communication with the reaction cavity for discharging one or more reactant products or unreacted (e.g., excess) reactants therefrom.

The material-containing laminate 100 will preferably form a portion of the reaction-cavity-defining surface of the microreactor. For example, with reference to FIGS. 4A through 4D, the material-containing laminate 100 comprises a candidate material 120 at an exposed surface 112 of a substrate 110. FIG. 4A shows a microreactor geometry with a single reaction cavity defined by a well-containing reactor block 200 and a single material-containing laminate 100. FIG. 4B shows a microreactor geometry with a single reaction cavity defined by an aperture-containing reactor block 200 and two material-containing laminates 100. This microreactor geometry provides an increased surface area of the candidate material, or alternatively, allows for supplying two different materials to the same microreactor. FIG. 4C shows a microreactor geometry with two independent reaction cavities, each reaction cavity being defined, in part, by a common material-containing laminate 100. The two independent reaction cavities can be isolated from each other (e.g., by using separate fluid distribution systems for each reaction cavity), or can be in fluid communication with each other (e.g., by cross-connecting the fluid distribution systems, such that the outlet from a first cavity is in fluid communication with an inlet to the second cavity). The geometry of FIG. 4C provides for efficient use of candidate material arrays, and increases the microreactor density of the chemical processing microsystem. FIG. 4D shows a microreactor geometry with a single reaction cavity defined by two well-containing reactor blocks 200, 200' and by an annular surface 112 defining an aperture in the substrate 110, with the film of candidate material 120 being formed on a part of the annular surface 112.

The material-containing laminate 100 can, however, be integral with the microreactor without forming a substantial portion of the reaction-cavity-defining surface thereof. In the microreactor geometry shown in FIG. 4E, for example, the material containing laminate 100 comprises microparticles 124, to which candidate material 120 is bonded, held in place between frits 126. Because a fluid-phase reactant can flow past the candidate materials and through the material-containing laminate, (for example, from well 235 to well 235'), such laminate does not define a substantial portion of the boundary surface of the reaction cavity.

The candidate materials are preferably, but not necessarily, arranged on the substrate in a substantially co-planar relationship with each other. While the plurality of candidate materials on an array, and the plurality of microreactors formed in a plurality of laminae are preferably coplanar with each other, alternative, non-planar geometries can, nonetheless, also be employed. For example, FIG. 5 shows a plurality of non-planar microreactors formed in a plurality of laminae.

Figure 6A:
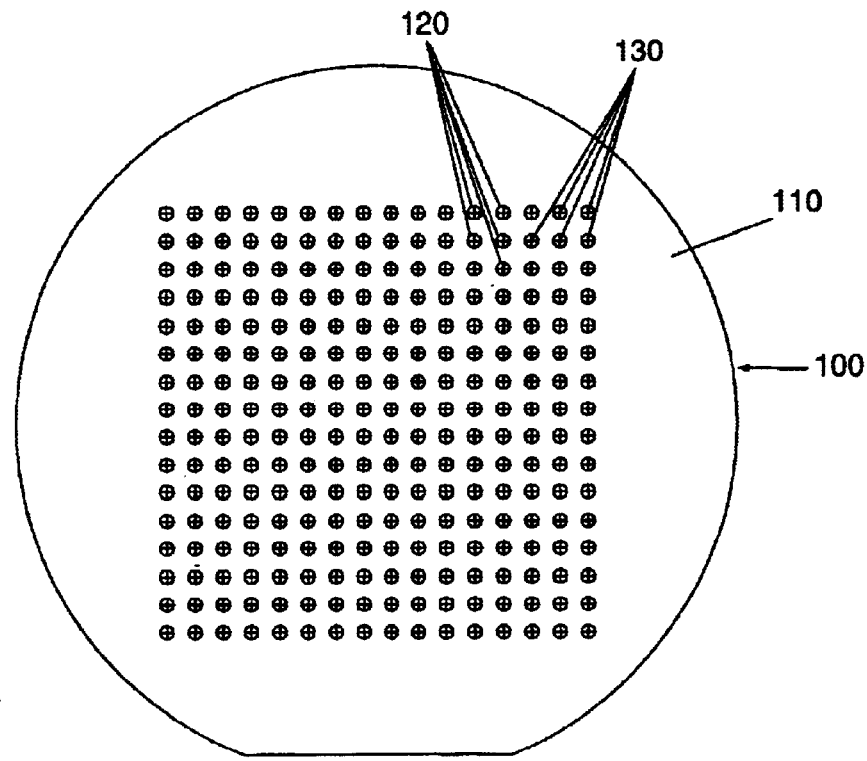
FIG. 6A and FIG. 6B are, respectively, a top plan view of a substantially planar wafer substrate for an array of 256 candidate materials (FIG. 6A), and a partial-cross-sectional side view of an individual well formed in one surface of the wafer substrate (FIG. 6B) into which candidate materials can be deposited.
Figure 6B:
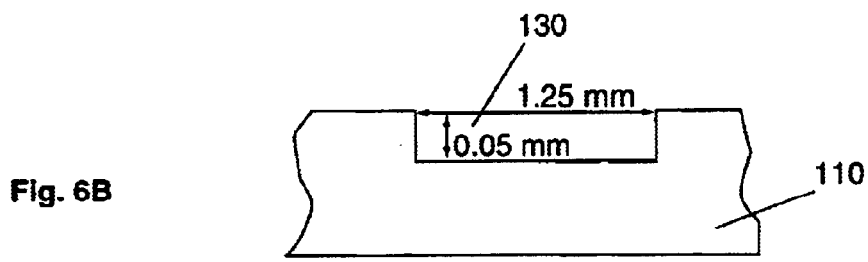

In a preferred embodiment, an array of solid candidate materials, such as prospective heterogeneous catalysts, are deposited by sol-gel techniques or in situ impregnation techniques onto a substantially planar substrate having a plurality of substantially co-planar wells formed at one surface of the substrate. With reference to FIGS. 6A and 6B, a silicon dioxide (quartz or glass) substrate 110 can comprise 256 circular-shaped wells 130 arranged in a sixteen-well by sixteen-well square array, with each well having a diameter of about 1.25 mm and a depth of about 0.05 mm. The distance between wells is about 4 mm. The preferred well-containing substrate 110 can be formed, for example, by masking a glass or quartz wafer with polycrystalline silicon using photolithography techniques, and then etching with a suitable etchant, such as hydrofluoric acid (HF), or alternatively, by mechanical means (e.g., machining, grinding, or bead-blasting). Candidate materials can then be deposited by sol-gel techniques or in situ impregnation techniques, such as those referred to above, to form the material-containing array 100. In an alternatively preferred embodiment, the material array comprises up to 1024 candidate materials on a substrate having 1024 wells arranged in a 32-well by 32-well square array. Such a material array can be prepared, for example, as described above in connection with the 256-well array, except that the distance between wells is reduced to about 2 mm.

As noted, a primary advantage of including the candidate materials on an array of materials is that the plurality of candidate materials can be loaded to (and subsequently unloaded from) the plurality of microreactors in parallel—by incorporating (or withdrawing) the entire array. In an alternative embodiment, the plurality of candidate materials could be serially loaded into an array (or directly into a plurality of microreactors). For such serial-loading approaches, the candidate materials may be encapsulated or otherwise prepared for handling and insertion into the microreactors.

Supplying Reactants to the Microreactors

With reference to FIG. 1C, reactants can be supplied to the plurality of microreactors 600 from an external distribution system 480 comprising one or more reactant sources. The external fluid distribution system 480 can comprise, for example, gaseous reactant sources 482 (e.g., gas cylinders), a gas flow-control device 483 (e.g., a mass-flow controller (MFC)), one or more control valves 484, preferably operated by a controller 485, and a common supply line 486 drawn from a mixing zone 487. The valves 484 and mixing zone(s) 487 can be housed within an oven 489. Liquid reagent sources 490 can likewise be supplied through a liquid-flow-control device 491 (e.g., syringe pumps; HPLC pumps). Liquid reactants can, if desired, be vaporized and provided to the microreactors in a vaporous state using methods and devices known in the art. According to one approach, the vapor in the head space over a temperature-controlled liquid can be provided to a mass flow controller (optionally heated) or other gas flow-control device. Alternatively, gas metered through an MFC can be bubbled through a temperature-controlled liquid. Other methods known or later developed for liquid delivery can also be employed.

A microfluidic distribution system can provide fluid communication between the external fluid distribution system 480 and each of the plurality of microreactors 600 (e.g., through one or more common inlet ports 510 to the chemical processing microsystem 10). With reference to FIG. 2, for example, distribution manifold 500 can provide fluid communication between the microreactors 600 and an external fluid distribution system 480 (through common inlet port 510 and reactor inlet port 250). Fluid communication between each of the microreactors and the external distribution system 480 can also be provided for reactor effluent (e.g., through reactor outlet ports 260), as discussed below.

Figure 7A:
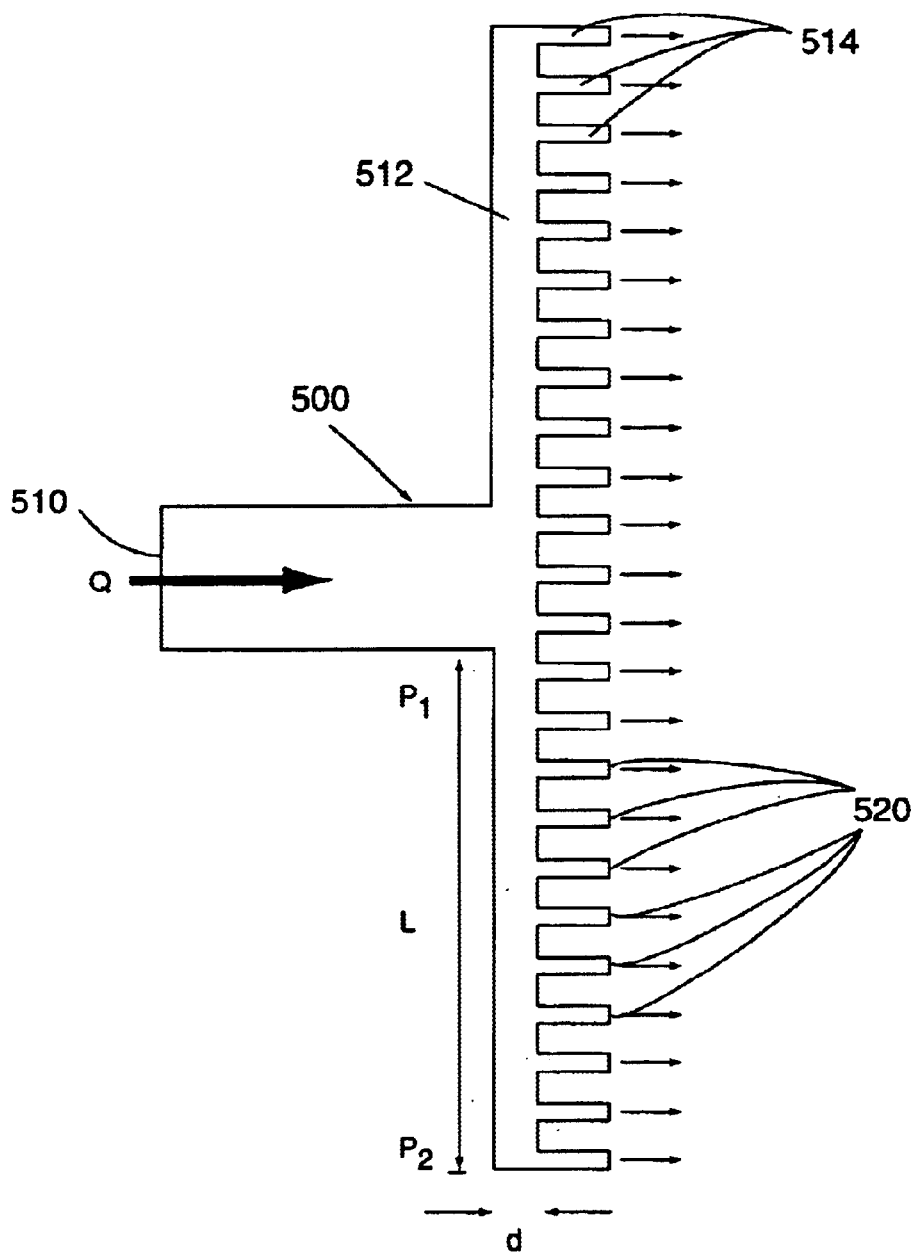
FIG. 7A through FIG. 7I are views of various exemplary embodiments of fluid-distribution systems that can be used for fluid communication between a plurality of microcomponents and an external fluid sources of sinks.

Another exemplary reactant supply (or discharge) manifold is depicted schematically in FIG. 7A. The supply manifold 500 comprises a single common inlet port 510, and a plurality of terminal outlet ports 520. The terminal outlet ports 520 are in fluid communication with the common inlet port via a common header 512 and a plurality of channels 514 oriented approximately normal to the common header 512.

For applications directed toward identifying new materials, the reactants are preferably supplied to the plurality of microreactors such that the inlet pressure of the fluid at each microreactor and the flow-rate (mass/volumetric flow rate) through each microreactor are substantially the same for each of the plurality of microreactors—to allow a basis for comparing different candidate materials. As such, the reactant supply manifold depicted in FIG. 7A, while adequate for some applications (e.g., with less than ten microreactors), is a less preferred embodiment. Because the pressure drop along the common header 512, varies over the distance, "L", the pressure at each terminal outlet port (and therefore, at each microreactor inlet) will vary, and the flow rate through each microreactor will vary. While the difference in pressures could be minimized by increasing the distance, "d", of the common header 512 such that the pressure at any distance, L, is approximately the same, the space constraints imposed by such an approach make such a design less desirable with more than about 10 microreactors.

Figure 7B:
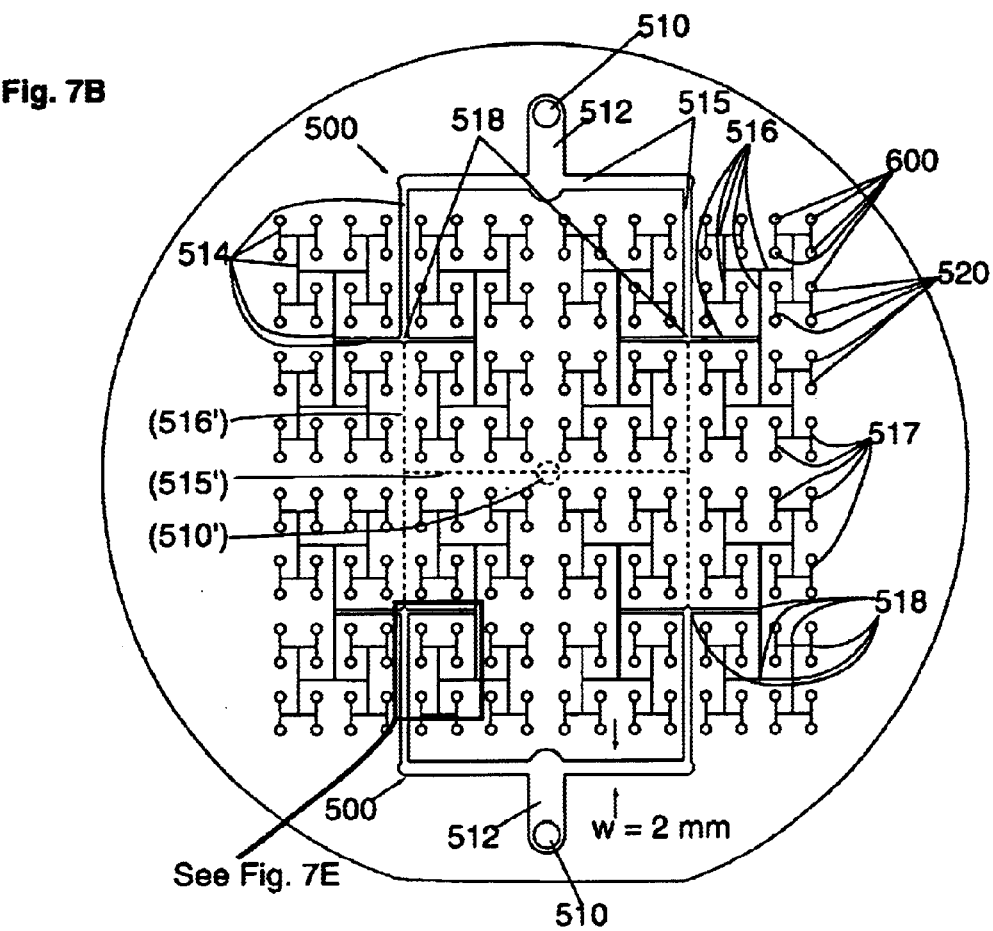

A preferred fluid distribution manifold is, therefore, designed to such that the flow paths to each of the microreactors have equal conductance—for example, flow paths of equal length and equivalent geometry—from the common port to each of the terminal ports. With reference to FIG. 7B, a preferred embodiment for a distribution manifold 500 comprising flow paths to a plurality of microreactors 600 can comprise a common port 510 adaptable for fluid communication with one or more reactant sources through one or more supply or recovery headers of an external fluid distribution system, $2^n$ terminal ports 520 adaptable for fluid delivery to or fluid recovery from $2^n$ microreactors (or, in the general case, other microcomponents), and a distribution channel (generally indicated as 514) providing fluid communication between the common port 510 and each of the $2^n$ terminal ports 520. To provide flow paths of equal length and equivalent geometry, the distribution channel 514 can comprise $2^n-1$ channel sections 515, 516, 517 connected with each other through $2^n-1$ binary junctions 518. Each of the $2^n-1$ channel sections 515, 516, 517 has at least three access ports serving one or more of the following functions: as a common port 510; as a connection port for a binary junction 518; or as a terminal port 520. Specifically, a first channel section 515 has access ports serving as the common port 510 and as connection ports for two binary junctions 518. Additionally, $[2^{n-1}-2]$ intermediate channel sections 516 have access ports serving as connection ports for three binary junctions 518. Moreover, $[2^{n-1}]$ terminal channel sections 517 have access ports serving as a connection port for one binary junction 518 and as two terminal ports 520.

To ensure equal flow-path lengths and substantially equivalent flow geometry, each of the channel sections 515, 516, 517 are preferably linear and the three access ports for a given channel section are preferably symmetrically arranged with one access port at the center of the linear channel section and one access port at each of the two ends of the linear channel section. Moreover, the linear channel sections are preferably configured to be mutually orthogonal to each other (forming right angles with each other at each binary junction). The channel sections may, however, be non-linear, include elbows (e.g., channel section 515), and/or be non-orthogonally oriented as long as the binary symmetry is preserved. The common port 510, channel sections 515, 516, 517, binary junctions 518 and terminal ports 520 are each preferably arranged in a common plane. For more complex designs, however, some of the components could be arranged in a non-planar, three-dimensional configuration.

As shown in FIG. 7B, each of two fluid distribution manifolds 500 provide fluid communication between a common port 510 and 128 microreactors 600, thereby serving a total of 256 microreactors. Hence, for each of the two fluid supply manifolds of FIG. 7B, the number, "n" is 7. In general, however, n, can be an integer not less than 4, and preferably ranges from about 4 to 20. The number, n, is more preferably not less than 6, even more preferably not less than 8, still more preferably not less than 10, and most preferably not less than 12. The number, n, can more preferably range from 6 to 18, even more preferably from 8 to 16, and most preferably from 8 to 12. Table 2 shows the details for a binary-tree fluid distribution manifold where n ranges from 4 to 8. Specifically, Table 2 shows the number of microcomponents to which a fluid can be communicated, the number of binary junctions associated therewith, and the number of channel sections associated therewith.

TABLE 2

Binary-Tree Distribution Manifold

| | | | Number (#) of Channel Sections | | |
|---|---|---|---|---|---|
| n | # of Terminal Ports served ($2^n$) | # of Binary Junctions ($2^n - 1$) | Total # ($2^n - 1$) | 1st Channel Section (w/common port and 2 binary junctions) | Intermediate Sections (w/3 binary junctions) ($2^{n-1} - 2$) | Terminal Sections (w/1 binary junction and 2 terminal ports) ($2^{n-1}$) |
| 4 | 16 | 15 | 15 | 1 | 6 | 8 |
| 5 | 32 | 31 | 31 | 1 | 14 | 16 |
| 6 | 64 | 63 | 63 | 1 | 30 | 32 |
| 7 | 128 | 127 | 127 | 1 | 62 | 64 |
| 8 | 256 | 255 | 255 | 1 | 126 | 128 |

Advantageously, the preferred, binary-tree distribution system allows for very efficient, uniform distribution of microcomponents in two-dimensional space, and thereby enables a higher microcomponent planar density—for example, a planar density of at least 1 microcomponent/cm$^2$, and preferably at least 5 microcomponents/cm$^2$.

Such an approach is particularly advantageous when incorporated into modular, laminae-type systems such as the preferred embodiment disclosed herein, because it allows for modular interchangeability of microcomponent distribution system without affecting the structural integrity of other subsystems.

Figure 7C:
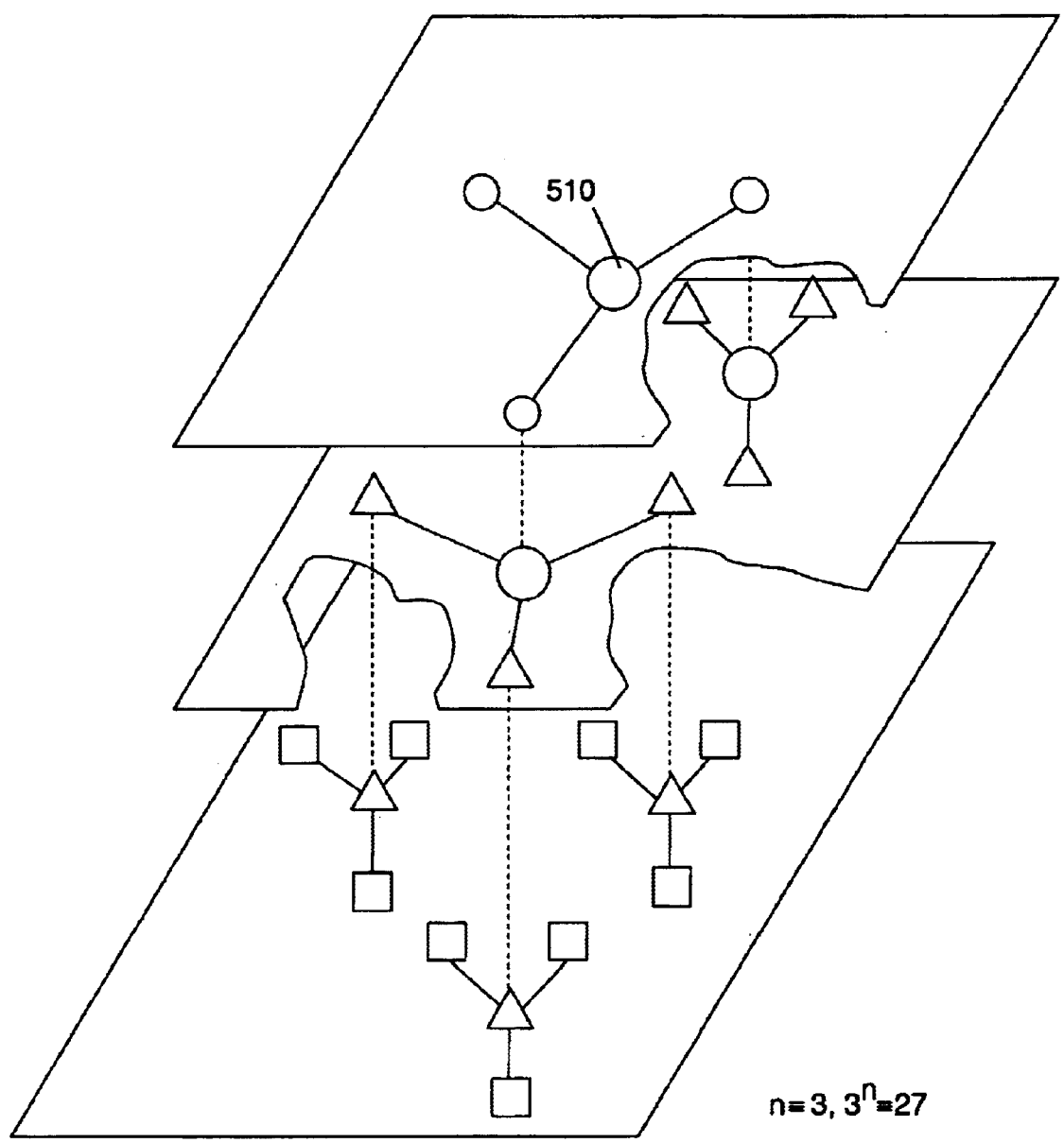
Figure 7D:
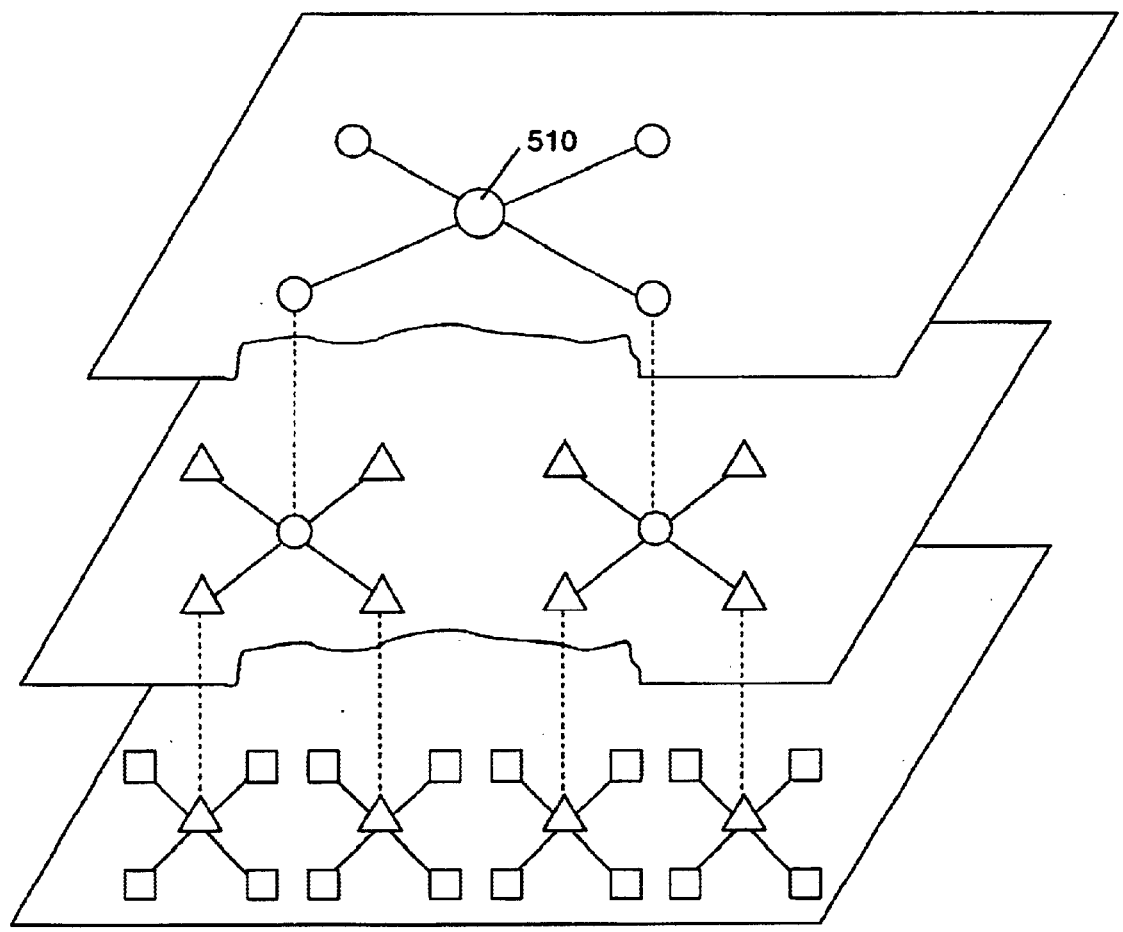

The concept of the binary-tree distribution manifold shown in FIG. 7B can likewise be extended to higher order distribution manifolds. For example, a ternary-tree design can comprise a common port adaptable for fluid communication with one or more supply or recovery headers, $3^n$ terminal ports adaptable for fluid delivery to or fluid recovery from $3^n$ microcomponents, and a distribution channel providing fluid communication between the common port and each of the $3^n$ terminal ports. To provide flow paths of equal length and equivalent geometry for ternary or even higher-order manifolds, however, the distribution channels thereof are preferably arranged in three-dimensions, and preferably on substantially parallel planar surfaces (e.g., wafers) with the ternary (or higher order) junctions at each level of distribution being co-planar with each other. The number of planar surfaces will be equal to the number "n". The concept of such a higher order distribution systems are illustrated in FIGS. 7C and 7D for ternary and quaternary distribution systems, respectively, for the case where n=3. The quaternary-tree distribution system of FIG. 7D is preferred over the ternary system with respect to maximizing device density.

Regardless of the design of the distribution manifold, the shape and/or dimensions the distribution channel are not limiting, except as specifically recited in the claims. The cross-sectional shape of a channel can be, for example, approximately square, rectangular, circular, oval, etc., or even irregular in shape, and may be determined primarily by the fabrication techniques employed. Approximately square or rectangular channels are typical, and the aspect ratio (width/depth) can be greater than 1, equal to 1 or less than 1. See, for example, U.S. Pat. No. 5,842,787 to Kopf-Sill et al. Because, however, the shape and/or dimensions of the distribution channel will affect the flow rate of reactants through each microreactor, these factors should be considered in connection with the overall chemical processing microsystem design, as discussed below in connection with the microreactor design. In general, the distribution channel can have dimensions, for an approximately square cross-section, of not more than about 1 cm×1 cm, preferably of not more than about 5 mm×5 mm, more preferably not more than about 2 mm×2 mm, even more preferably of not more than about 1 mm×1 mm, and still more preferably of not more than about 100 $\mu$m×100 $\mu$m. Smaller dimensions can also be suitably employed in some applications, including dimensions of not more than about 10 $\mu$m×10 $\mu$m, not more than about 1 $\mu$m×1 $\mu$m, and not more than about 0.5 $\mu$m×0.5 $\mu$m. The channel can have a rectangular cross-section with an aspect ratio of greater or less than one, and dimensions adjusted to as to provide the same general ranges of cross-sectional flow area as described for a square cross-sectional channel. For an approximately circular cross-section, the diameter can be not more than about 1 cm, preferably not more than about 5 mm, more preferably not more than about 2 mm, even more preferably not more than about 1 mm, and still more preferably not more than about 100 $\mu$m. Smaller dimensions can also be suitably employed in some applications, including a diameter of not more than about 10 $\mu$m, not more than about 1 $\mu$m, and not more than about 0.5 $\mu$m. Described in terms of hydraulic radius, the distribution channel can have a hydraulic radius of not more than about 2.5 mm, more preferably not more than about 1.25 mm, even more preferably of not more than about 0.5 mm, yet more preferably of not more than about 0.25 mm, and most preferably not more than about 25 $\mu$m. Smaller hydraulic radii can also be suitably employed in some applications, including a hydraulic radius of not more than about 2.5 $\mu$m, not more than about 0.25 $\mu$m, and not more than about 0.125 $\mu$m. Hence, the hydraulic radius of the distribution channel preferably ranges from about 2.5 mm to about 0.125 $\mu$m, more preferably from about 1.25 mm to about 0.25 $\mu$m, and most preferably from about 2 mm to about 2.5 $\mu$m.

The shape and dimensions of the cross-section of the distribution channel can be constant along the entire length of a distribution path or, if desired, can be varied along such length. If shape and/or dimensions of the channel are varied along the fluid-distribution path, however, the binary (or ternary, quaternary, etc.) symmetry is, in some applications, preferably maintained to provide for equal conductance along each fluid-distribution path. In other applications, the conductance of each flow path can be purposefully varied to provide for a tailored flow distribution to the plurality of microreactors (and corresponding tailored residence times, etc).

The distribution manifold can preferably provide, in addition to its fluid-distribution function, a pressure reducing function. The pressure reducing function can be in the supply manifold or, if desired, in the discharge manifold. In general, the biggest pressure drop in the system is designed to be outside of the microreactor, to minimize the effect of minor variations in microreactor fabrication or catalyst loading on reactor pressure. Moreover, the biggest pressure drop is preferably designed to occur in the supply manifold, immediately before each microreactor. Such a design minimizes the cross-microreactor effect in the event that flow through one of the microreactors becomes inoperative (e.g., blocked or clogged). Pressure reduction can be achieved through active microcomponents (e.g., microvalves) or passive microcomponents (e.g., microscale flow restrictors). Pressure reduction can also be, and is preferably, achieved by reducing the cross-sectional flow area (and therefore, the hydraulic radius) of the distribution channel along the length thereof. For the preferred binary-tree embodiment, for example, the cross-sectional flow area of each channel section can be reduced at each binary junction relative to the immediately preceding (upstream) channel section. Most preferably, the cross-sectional flow area is reduced by ½ at each binary junction, thereby resulting in a substantially linear pressure drop along the flow-path from the common port to the terminal port.

The length of the distribution path between the common port and each terminal port is not generally limiting. In preferred embodiments, however, the length of each of the flow paths is designed such that the conductance is substantially the same for each of the flow paths. In a substantially planar binary-tree design, such as that shown in FIG. 7B, the overall length of each flow path, L, will generally depend on the arrangement of the microcomponents 600 and on the inter-component space.

Figure 7E:
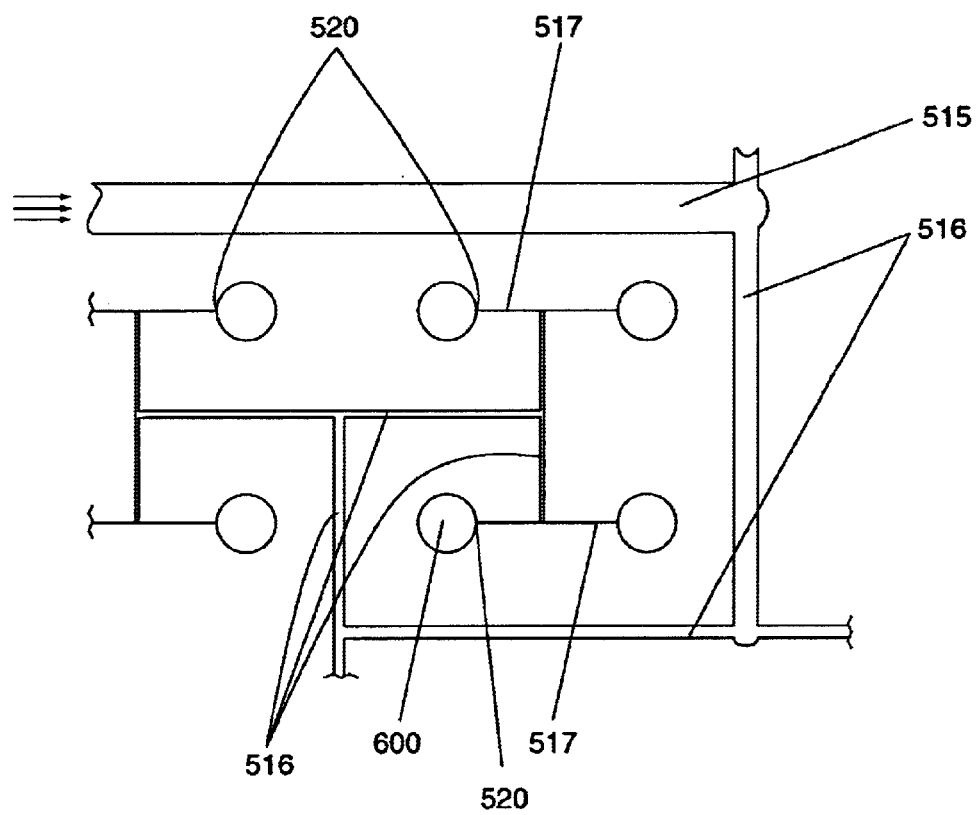
Figure 7F:
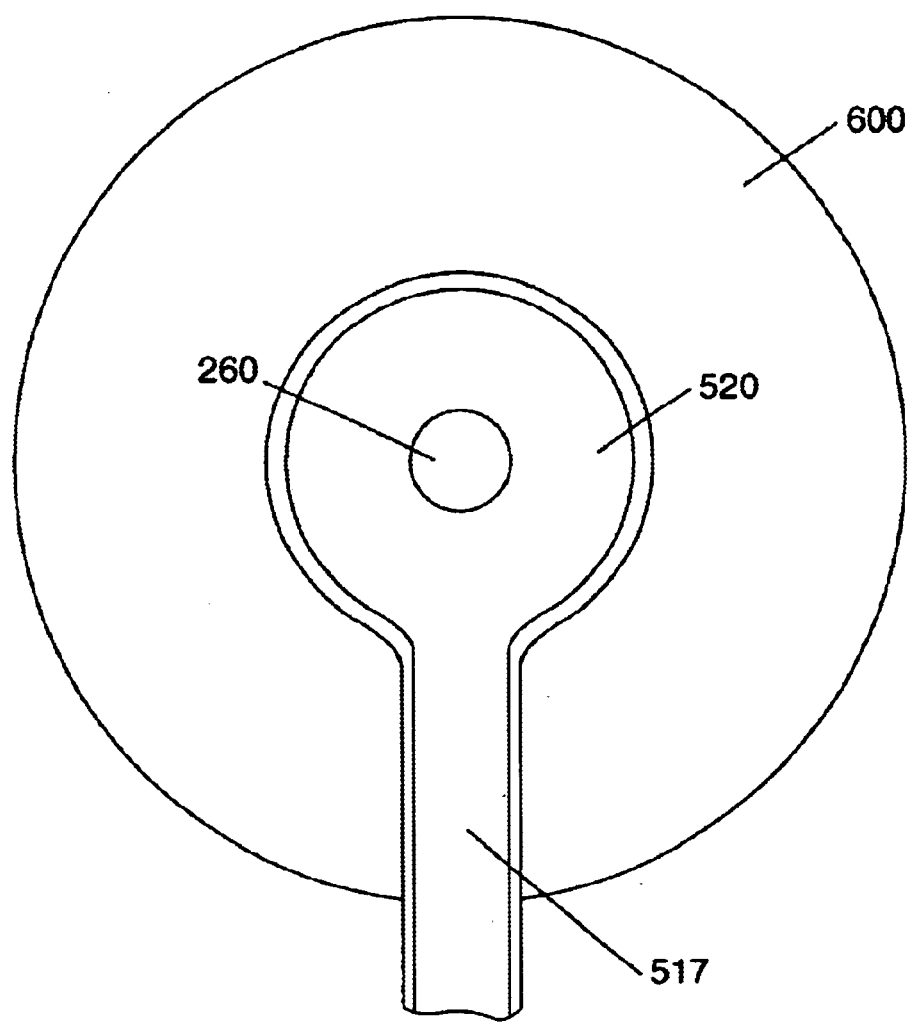
Figure 7G:
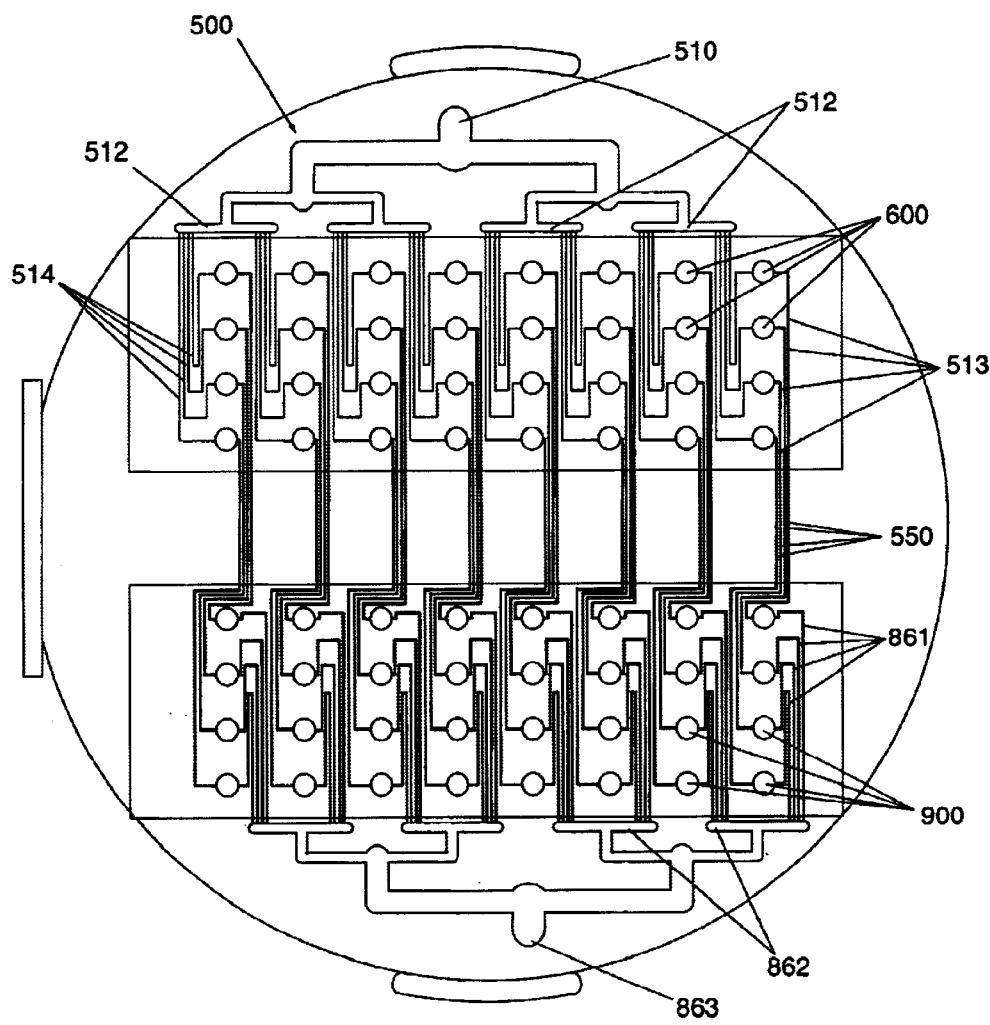
Figure 7H:
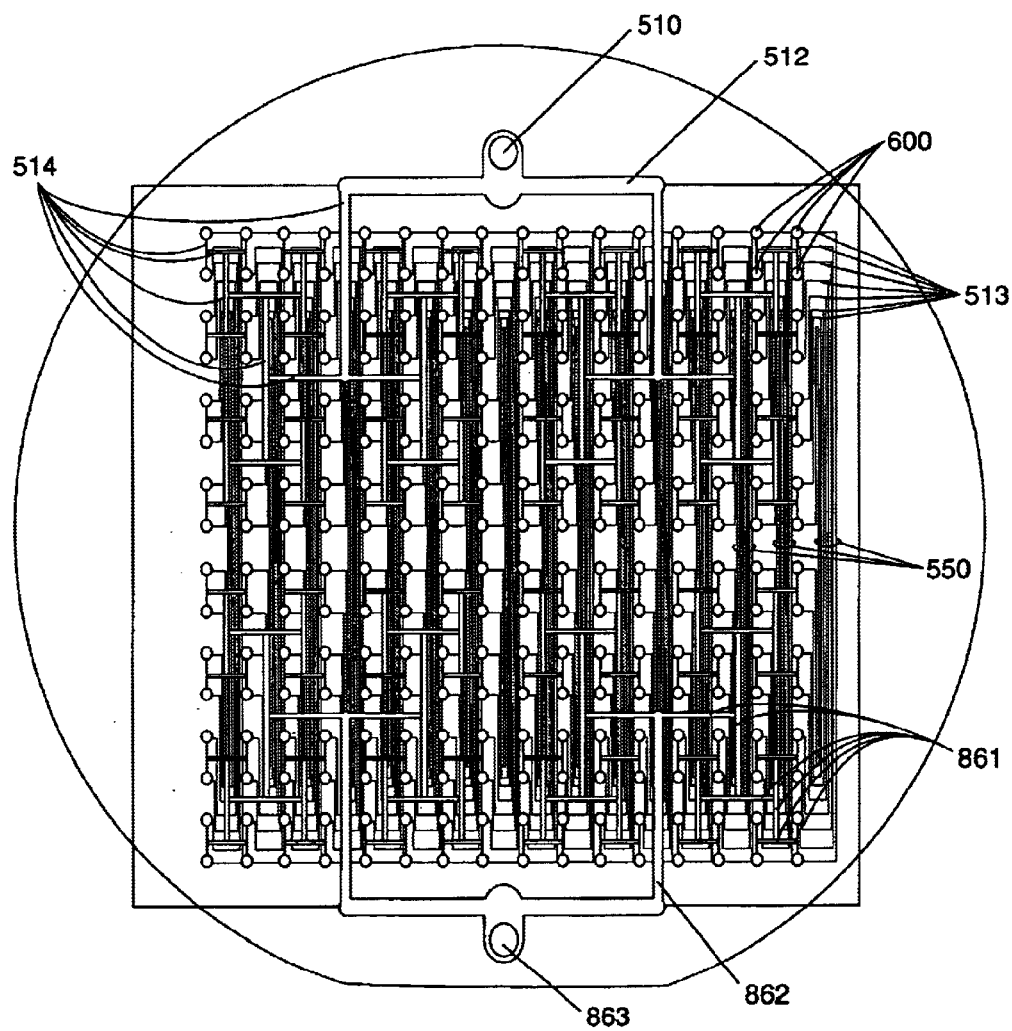
Figure 7I:
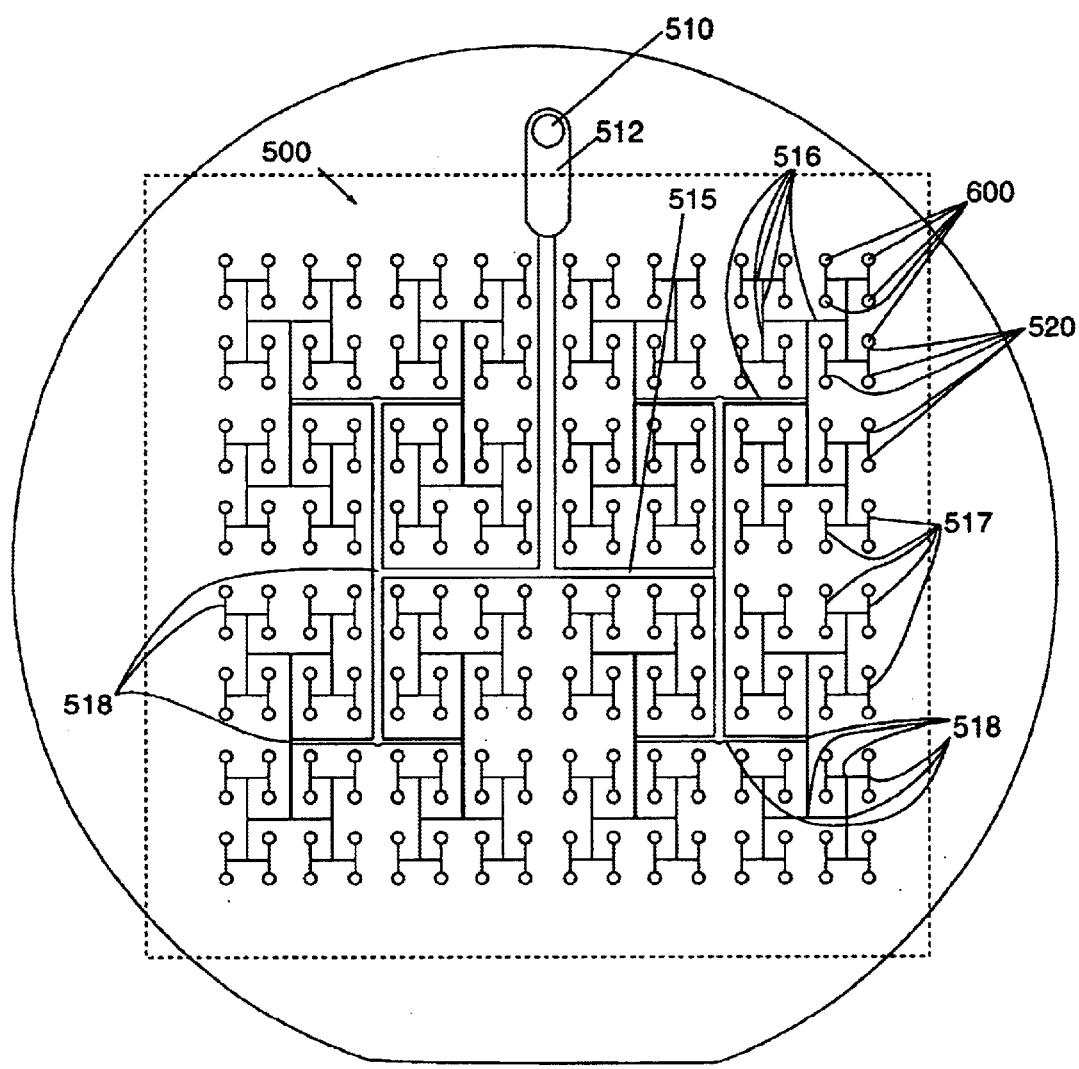
Figure 8:
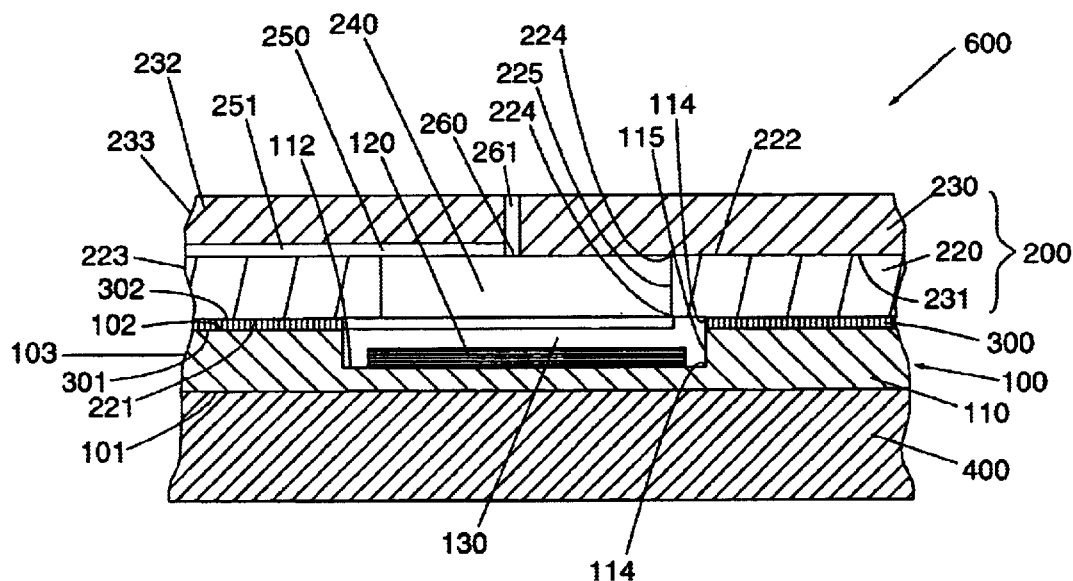
FIG. 8 is a partial cross-sectional side view of a plurality of laminae having a candidate-material containing microreactor formed therein.

The distribution manifolds of FIGS. 7B and 7I are preferred fluid-supply manifolds suitable for use in connection with the preferred array of candidate materials depicted in FIG. 6A and discussed in connection therewith. Referring to FIG. 7B, the common port 510 has a circular cross-sectional shape and an inside diameter of about 2 mm feeding into an associated short common header 512 having an approximately rectangular cross-section with a width of 2 mm and a depth of about 20 $\mu$m. Two L-shaped first channel sections 515 (that feed the first two channel sections having three binary junctions) have a generally rectangular cross-sectional with a first leg of the L-shaped first channel section 515 having a width of about 2 mm, and the second leg of the L-shaped first channel section 515 having a width of about 1 mm, and in each case, a depth of about 20 $\mu$m. The width of each successive intermediate channel sections 516 (having three binary junctions) is then reduced by ½ relative to the preceding intermediate channel section, with the depth thereof remaining at about 20 µm. FIG. 7E is a schematic of a one flow path of the distribution manifold of FIG. 7B, and shows a portion of the first channel section 515, several intermediate channel sections 516 and terminal channel sections 517 in fluid communication with several microreactors 600. As shown therein, the width of each successive intermediate channel section 516 is reduced by a factor of about ½, and the terminal channel section has a width of about 10 µm and a depth of about 10 µm. The overall length of the flow path from the common port 510 to each of the 128 terminal ports 520 is about 60 mm. FIG. 7F shows an enlarged top plan view of a microreactor 600 in fluid communication with a terminal channel section 517 through terminal port 520 of the distribution channel (which also serves as inlet port 250 of the microreactor 600). A microreactor outlet port 260 is also shown—located at the top of the microreactor 600 (as shown in FIG. 8 and discussed in connection therewith).

The preferred distribution manifold of FIG. 7B can be interfaced with an external fluid distribution system 480 (FIG. 1C) by a number of different approaches. In a preferred approach, with reference to FIG. 7B, vertical conduits (not shown in FIG. 7B) can extend normal to the plane of the binary-tree distribution system and connect to common inlet ports 510. (See FIGS. 18G and 18H and discussions in connection therewith). While shown in FIG. 7B as two common inlet ports 510 located near the edges of the wafer, a single, centrally-located common inlet port (shown with dashed circle as 510') could likewise be employed, and connected the binary tree of FIG. 7B through an alternative first channel section (shown with dashed lines as 515') and through an intermediate channel section (shown with dashed lines as 516'). As shown in FIG. 7I, a single common inlet port 510 can alternatively be located near the peripheral edge of the wafer.

In the general case, a binary-tree, regular square array of M×M microcomponents (such as microreactors) can be designed according to the following approach. Preferably, the following design parameters are determined in advance—based on system requirements for which the fluid distribution manifold will be designed: the number of microcomponents (e.g., expressed as a binary exponential, $2^n = M^2$); an inter-component spacing, $\Delta l$; the volumetric flow rate, $V_{terminal}$ (or mass flow rate, m); the outlet pressure, $P_{terminal}$, required at each terminal port; the inlet pressure, $P_{common}$, required at the common port; and a channel cross-sectional geometry. The overall length, L, for each of the flow paths can be calculated from the number of microcomponents and the inter-component spacing by the following Equation 1:

$$L = \Delta l (2^{n/2} - 1) \qquad \text{Equation 1}$$

Then, the channel dimensions for the give channel geometry can be determined, based on conductance, to provide the desired pressure drop for the desired flowrate. For example, the necessary channel height for a channel of length L having an approximately rectangular cross-sectional dimensions of h×w can be calculated by Equation 2:

$$h = [24(\mu L Q)(1/w)(p_{common}^2 - p_{terminal}^2)^{-1}]^{1/3} \qquad \text{Equation 2}$$

where $\mu$ is the fluid viscosity and Q is the pressure-volume per unit time.

The aforedescribed binary-tree, ternary-tree or quaternary-tree distribution manifolds can be employed as a microfluidic supply manifold or as a microfluidic discharge manifold for any application requiring the supply of fluids from a common port to a plurality of microcomponents. In preferred applications, the distribution manifold can supply reactants, non-reacting fluids (e.g., carriers), and/or candidate materials to the plurality of microreactors. In other applications, for example, the distribution manifold could also be employed for high-precision parallel dispensing of a fluid to a plurality of microcontainers (for example, for dilution, scavenging, purging, etc.).

An alternative fluid distribution system design is shown in FIG. 7G. With reference thereto, distribution manifold 500 comprises fluid-supply flow paths to an array of thirty-two microreactors 600. Fluid communication between common port 510 and microreactors 600 is provided through common headers 512 and supply channels 514. As depicted, each of the supply channels 514 have substantially the same flow-path length and equivalent geometry, thereby having equal conductance, and providing substantially the same pressure and flow rate at each of the microreactors 600.

The distribution manifold (for both supply and/or effluent) is, in any case, preferably a modular component, such as a wafer, and preferably in releasable and/or sealed contact with other components of the microreactor structure, such that different distribution manifolds can be readily interchanged with each other. Such a design provides a means for changing the reaction conditions (e.g., flow rate, residence time) for a plurality of microreactors by a simple exchange of the modular distribution wafer.

While the aforedescribed fluid distribution manifold is a preferred embodiment of the invention, other parallel-fluid distribution schemes may also be employed. In general, for parallel fluid distribution systems, the ratio of distribution manifold terminal outlet ports (i.e., corresponding to microcomponent inlet ports) to distribution manifold common inlet ports is preferably at least 10:1, more preferably at least 20:1, and can, for higher number of microcomponents, be at least 30:1, at least 50:1, at least 75:1, at least 100:1, at least 150:1, at least 200:1 and at least 250:1 or higher. Instead of simultaneous, parallel delivery, however, rapid-serial delivery of fluids to each of the microreactors may also be employed. Serial-parallel hybrid delivery systems, involving rapid successive parallel delivery of fluids to a subset of the total number reactors may likewise be effective with the present invention. Such a rapid-serial-parallel approach is described, for example, in copending U.S. patent application Ser. No. 09/093,870, filed Jun. 9, 1998 by Guan et al.

Microreactors

The particular design of the microreactors employed in connection with the present invention is not limiting, except as specifically recited in the claims. The microreactor design can vary, for example, depending on the type of chemical process being investigated, and with respect to chemical reactions, depending on the particular reaction being effected. Generally, for chemical reactions, each of the plurality of microreactors in a chemical processing microsystem comprises a surface defining a reaction cavity for carrying out a chemical reaction, an inlet port in fluid communication with the reaction cavity for supplying one or more reactants thereto, and—for continuous reactor operations—an outlet port in fluid communication with the reaction cavity for discharging a reactor effluent (including one or more reaction products and one or more unreacted reactants) therefrom. Hence, in general, many, if not all, of the single microreactor designs reported in the literature can be employed in connection with the present invention, including, for example, microchannel-type microreactors, cell-type microreactors, combined microflow (e.g., "Y"-shaped or "T"-shaped) reactors, electrochemical reactors, photochemical reactors, etc. The microreactors can have integrated microscale heat-control components, active microcomponents such as mixers, valves, etc., and/or passive microcomponents such as passive mixers. Such components can be dedicated to service individual microreactors, or can be generic to several or to all of the microreactors of the chemical processing microsystem. The micoreactors can be designed to model (or be indicative or representative of) conventional, commercial-scale reactors such as continuous-stirred-tank reactors (CSTR's) and plug-flow reactors (PFR's), among others. With respect to heterogeneous catalyst screening applications, microreactors modeling CSTR's may, as discussed below, be advantageously applied for primary screening tasks, and PFR's may be better suited for secondary screening tasks.

The number of microreactors included within the chemical processing microsystem is at least 2, preferably at least 4, more preferably at least 7, still more preferably at least 10, more preferably still at least 15 and even more preferably at least 20 for moderate throughput embodiments. In higher throughput embodiments, the number of microreactors in the chemical processing microsystems is at least 25, more preferably at least 30, even more preferably at least 50, still more preferably at least 75, yet more preferably at least 100, and most preferably at least 250. Present microscale and nanoscale fabrication techniques can be used, however, to prepare microsystems having an even greater number of microreactors. For even higher throughput operations, for example, the number of microreactors can be at least about 400, preferably at least about 1000, more preferably at least about 10,000, even more preferably at least about 100,000, and most preferably at least about 1,000,000 or more.

The number of microreactors may, however, be the same as or different from the number of candidate materials being investigated, since some of the microreactors may be supplied with the same candidate material, left as blank controls, or with supplied with positive or negative control materials having known properties. For applications directed to identifying new materials having a useful property of interest, at least two or more, preferably at least four or more, in many cases most, and allowably each of the plurality of microreactors comprise at least a portion of one or more different candidate materials within the reaction cavity thereof. Specifically, a different candidate material can be included within at least about 50%, preferably at least 75%, preferably at least 80%, even more preferably at least 90%, still more preferably at least 95%, yet more preferably at least 98% and most preferably at least 99% of the plurality of microreactors. For example, "X" different candidate materials being investigated can be individually resident in separate, dedicated microreactors included in a microsystem having "Y" total microreactors as follows: 4 of 7, 8 of 15, 15 of 30, 25 of 50, 75 of 100, 90 of 100, 225 of 250, and 950 of 1000. For some applications, however, it may be desirable to include different candidate materials in a smaller percentage of the total number of microreactors. For example, four or more different candidate materials can be evaluated as separate, parallel-groups of materials, with each group of materials being subjected to different process conditions. More specifically for example, four or more different candidate materials (e.g. A, B, C, D) can be evaluated in eighty microreactors as twenty groups of the four different materials with each of the twenty groups being subjected to various process conditions. In such a case, different candidate materials occupy only 5% of the total number of microreactors. In the general case, a different candidate material can be included within not less than about 5%, preferably not less than about 10%, more preferably not more than about 20%, even more preferably not more than about 30%, and still more preferably not more than about 40% of the plurality of microreactors. Particular examples, in which "X" different candidate materials are investigated in groups in a microsystem of "Y" total microreactors, are as follows: 4 of 8, 4 of 12, 4 of 16, 4 of 40, 10 of 20, 10 of 40, 10 of 50, 10 of 100, and 10 of 200. Other combinations, including both general schemes and specific arrangements are also possible and within the experimental design selection of a person of skill in the art.

In preferred embodiments, the microreactors are arranged as an array of microreactors that spatially corresponds to the array of candidate materials. The microreactors are preferably arranged in a substantially planar array (e.g., as shown in FIG. 2), but could also be arranged in non-planar array (e.g., as shown in FIG. 5). Hence, in preferred embodiments, the separation between adjacent microreactors (center of reaction cavity to center of reaction cavity) can range from about to about 50 $\mu$m to about 1 cm, more preferably from about 100 $\mu$m to about 7 mm, and most preferably from about 1 mm to about 5 mm. The inter-microreactor spacings can be not more than about 1 cm, not more than about 7 mm, not more than about 5 mm, not more than about 4 mm, not more than about 2 mm, not more 1 mm, not more than about 100 $\mu$m, and not more than about 50 $\mu$m. Exemplary inter-microreactor spacings (center-to-center) based on preferred embodiments of the invention are 4 mm for having 256 addressable regions on a three-inch wafer substrate, and 2 mm for having 1024 addressable regions on a three-inch wafer substrate. As such, the planar surface density of microreactors can range from about 1 microreactor/cm$^2$ to about 200 microreactors/cm$^2$, more preferably from about 5 microreactors/cm$^2$ to about 100 microreactors/cm$^2$ and most preferably from about 10 microreactors/cm$^2$ to about 50 microreactors/cm$^2$. The planar density can be at least 1 microreactor/cm$^2$, at least 5 microreactors/cm$^2$, at least 10 microreactors/cm$^2$, at least 25 microreactors/cm$^2$, at 50 microreactors/cm$^2$, at least 100 microreactors/cm$^2$, and at least 200 microreactors/cm$^2$. For moderate throughput systems, lower or mid-range densities may be preferred. For other, higher throughput systems, higher microreactor densities are generally preferred. Additionally, even higher densities may be achieved as fabrication technology develops to nano-scale applications.

Regardless of the specific microreactor geometry or arrangement, each of the plurality of microreactors can be designed to be permanently integrated with the array of candidate materials (e.g., by anodically bonding the candidate-material-containing wafer to the microreactor-well containing wafer), or can be releasably and preferably sealably integrated with the array of candidate materials being investigated (e.g., as described above), to facilitate efficient interchanging (that is, loading, unloading and reloading) of candidate material libraries (e.g., arrays) with a reusable chemical processing microsystems.

The microreactors included in the chemical processing microsystem are preferably formed in a plurality of laminae. The laminae in which the microreactors are formed can be integrated with, and in some embodiments are preferably releasably integrated with, at least one material-containing laminate comprising the candidate materials being investigated. In a preferred embodiment shown schematically in FIG. 8, a microreactor 600 is formed in a plurality of laminae comprising a (material-containing) first laminate 100, and a composite reactor block 200 comprising a (reactor) second laminate 220 adjacent to the material-containing first laminate 100 and a (capping) third laminate 230 adjacent the reactor second laminate 220. A releasable seal 300 is preferably situated between the material-containing first laminate 100 and the reactor second laminate 220. The releasable seal can preferably withstand the reaction conditions for the chemical reaction of interest. In general, the releasable seal can preferably withstand temperatures greater than 100° C., and preferably greater than about 200° C. The releasable seal can preferably withstand pressures greater than about 20 bar, preferably greater than about 50 bar, and more preferably greater than about 100 bar. As an alternative to the releasable seal 300, however, the material-containing first laminate 100 and reactor second laminate 200 could be bonded to each other (e.g., anodically, or for some applications, with an inert epoxy or other suitable adhesive). Preferably, such a bond can withstand the required reaction conditions for the chemical reaction of interest. In the general case, the bond can preferably withstand temperatures of not less than about 100° C., preferably of not less than about 200° C. and/or a pressure of not less than about 100 bar, preferably of not less than about 200 bar.

More specifically, with reference to FIG. 8, the material-containing first laminate 100 has a first surface 101, a second surface 102 in spaced, substantially parallel relationship to the first surface 101, and a circumferential edge 103. The reactor second laminate 220 has a first surface 221 in releasable contact with the second surface 102 of the first laminate 100, a second surface 222 in spaced, substantially parallel relationship to the first surface 221, and a circumferential edge 223. The capping third laminate 230 has a first surface 231 bonded to the second surface 222 of the reactor second laminate 220, a second surface 232 in spaced, substantially parallel relationship to the first surface 231, and a circumferential edge 233. The reactor laminate and capping laminate can be of any material suitable for the reaction conditions. The capping laminate may, for example, be photo-transmitting for use in connection with photo-chemical reactions. The reactor second laminate 220 further comprises interior edges 224 and an interior surface 225 defining an aperture (with corresponding void space) in the second laminate 220, such that, taken together, the second and third laminates 220, 230 form a composite substructure, reactor block 200, comprising a well defined by the interior edge 224 and interior surface 225 of the second laminate 220 and those portions of the first surface 231 of the third laminate circumscribed by such interior edge 224. As noted, the material-containing laminate 100 can be bonded or releasably engaged with at least one of the adjacent laminates, and preferably, with at least the reactor block 200. A bonded contact between these surfaces may be preferred for higher pressure applications and/or for single-loading systems (e.g., disposable systems, or for catalyst that do not readily foul or which can be regenerated in situ). For multiple-loading systems, the releasable contact between the reactor second laminate 220 and the material-containing first laminate 100 can be provided by a releasable seal 300 such as a solid gasket, gasket dressing, and/or other suitable material. The material-containing laminate 100 is also preferably in releasable contact with (and releasably engaged with) a surface of any other adjacent laminate, such as the temperature-control block 400. Each of the laminae materials should be compatible with the chemical process of interest, including with respect to resistance to chemical degradation, temperature and pressure considerations, heat transfer considerations, fabrication (including bonding and/or sealability), etc.

The material-containing laminate 100 further comprises a candidate material 120 (a) known to have catalytic activity for a gaseous chemical reaction, (b) being screened for catalytic activity for a gaseous chemical reaction, or (c) operating as a control material therefor (including the substrate material serving as a blank control). The candidate material 120 can be on formed on an exposed surface of the first laminate 100 as shown in FIG. 8, on a surface 112 of a well 130 formed in the material-containing first laminate 100. The well in the material-containing laminate is defined by material-containing surface 112, interior edges 114 and interior surface 115. Taken together, the first, second and third laminates 100, 220, 230 form a microreactor defined by the interior edges 224 and interior surface 225 of the second laminate, by the interior edges 114, interior surface 115, material-containing surface 112 and the candidate material 120 of the first laminate 100, and by those portions of the third laminate 230 circumscribed by the interior edges 224 of the second laminate.

With respect to fluid distribution, the microreactor 600 further comprises a reactor inlet 250 formed as a microfluidic channel 251 between the second and third laminates 220, 230, and a reactor outlet 260 formed as an interior surface 261 defining an aperture in the third laminate 230. The inlet 250 is preferably in fluid communication with a microfluidic distribution system, such as that described in connection with FIG. 7B (with the microfluidic channel 251 of FIG. 8 corresponding to a terminal channel section 517 of FIG. 7B). The outlet 260 is preferably in fluid communication with analytical devices and/or instrumentation, as discussed in further detail below.

The microreactor, such as that shown in FIG. 8, may further comprise one or more ports (not shown in FIG. 8) for analytical microinstruments (e.g., temperature and/or pressure monitoring) and/or for process control elements (e.g., pressure-relief valves). The microreactor may also comprise a temperature-control block 400. The temperature-control block 400 can be a heating block (useful, for example for maintaining reaction temperature in a reactor during an endothermic reaction), a cooling block (useful, for example, for maintaining reaction temperature in a reactor during an exothermic reaction), or an insulator block (useful, for example, for providing adiabatic or quasi-adiabatic conditions during a reaction). As discussed below, the temperature of the temperature-control block can be controlled to maintain the same temperature for the plurality of microreactors, or alternatively, to provide a different temperature for a plurality of microreactors, or to provide a different temperature for e ach of the microreactors. As shown in FIG. 18E and discussed in connection therewith, fine tuning of the temperature profile can be achieved using additional heating elements integral with the material-containing laminate or integral with a microreactor support laminate (block) adapted to receive the material-containing laminate.

A plurality of microreactors, such as the preferred embodiment shown in FIG. 8, can be fabricated in a plurality of laminae using microscale and nanoscale fabrication techniques known in the art. With reference now to FIGS. 9A and 10A through FIGS. 9I through 10I, respectively, for example, a plurality of composite reactor blocks 200 having an integral fluid distribution system, such as the supply distribution system 500 shown on FIG. 7B, can be fabricated in a reactor first laminate 220 and a capping second laminate 230. The fluid distribution system, as shown in FIGS. 9A and 10A, includes a supply distribution channel 514 in fluid communication with a reactor inlet port (the location of which is generally indicated at 250), and a discharge distribution channel 261 in fluid communication with reactor outlet port 260.

Briefly, to fabricate a plurality of reactor blocks 200, an etch-mask 270 (e.g., low-stress silicon nitride, $Si_3N_4$, 500 nm) is deposited by chemical vapor deposition onto an exposed first surface 231 of the capping second laminate 230 (FIG. 9B–9C, FIG. 10B–10C) (e.g., 100 mm silicon, <100>). A photoresist layer 272 (e.g., Shipley 1813) is photolithographically patterned and developed (e.g., with MF-319) onto an exposed surface of the etch mask 270 (FIG. 9D, FIG. 10D). The patterned photoresist layer exposes a plurality of desired portions 273, 274 of the surface of the etch mask 270. Exposed portions 273 can be, for example, a circular shape, and exposed portions 274 can be designed to correspond to the desired supply distribution manifold. The etch mask 270 is then selectively etched (e.g., $SF_6/CF_3Br$ plasma etch) and the remaining photoresist layer 272 is subsequently stripped (e.g., sulfuric acid/hydrogen pyroxide, 4:1) (FIG. 9E, 10E), to expose desired portions 233, 234 of the first surface 231 of the first laminate 230. The exposed portions 233, 234 of the laminate 230 are then selectively etched (e.g., with KOH (22.5%, 80° C.)) to form shallow wells 235' and the supply distribution channel 514 in the first laminate 230. (FIG. 9F, FIG. 10F). An aperture defining discharge distribution channels 261 and the reactor outlet ports 260 can be provided through the first laminate 230 (e.g., by drilling with a YAG laser). (FIG. 9G, FIG. 10G). The aperture can extend from the well 235' surface to the second surface 232 of the second laminate 230. The etch mask 270 can then be stripped from the second laminate 230, (FIG. 9H, FIG. 10H) to form a subassembly of the second laminate 230 (having a shallow well 235' and a fluid distribution system (514, 250, 260, 261) integral therewith). Referring now to FIGS. 9I and 10I, a plurality of apertures defining interior edges 224 and interior surface 225 can be formed in the reactor first laminate 220 (e.g., by ultrasonically drilling the, e.g., glass laminate), with the aperture extending from a first surface 221 to a second surface 222 of the laminate 220, to form a subassembly of the first laminate 220 (having a plurality of apertures). The first and second laminate 220, 230 subassemblies can then be bonded (e.g., anodically bonded) to form the reactor block 200 of FIGS. 9A and 10A having a plurality of reactor wells 235.

With reference to FIG. 8, the plurality of microreactors can then be assembled by releasably combining the composite reactor block 200 and a material-containing array 100 with a releasable seal (e.g., gasket) therebetween. The seal can be prepared from any suitable material. The seal materials can be thin metal foils, such as Cu, Au, Ag, Al, Ni, or combinations thereof (e.g., Au-coated Cu). Quart (e.g., quartz paper, impregnated quartz paper), and graphite foil can also be suitable gasket materials for many applications. Polymeric materials such as TEFLON (e.g., expanded polytetrafluoroethylene (PTFE)), polyimides, various elastomers, etc., combinations thereof, or combinations thereof with other materials (e.g., metals, graphite) may be suitable for other, relatively lower temperature applications. The gasket seal can be prepared from sheets of such materials (e.g., "quartz paper") by providing apertures (e.g., by punching or drilling) arranged to correspond to the reactor wells 235' and/or portions of the array 100 that include the candidate materials 120). A second releasable material (not shown) may be provided between the material-containing array 100 and the heating block 400 or other support block adjacent the opposite first side 101 of the array 100.

Several microreactor design parameters are typically considered with respect to designing a microreactor for a particular chemical process of interest. Such design parameters include, without limitation, the microreactor volume, the microreactor geometry (e.g., shape), the inlet port location and sizing, the outlet port location and sizing, and the type, amount, surface area and/or the relative location of the candidate material being investigated, among others. In general, the microreactor design parameters can be constrained by the desired process conditions (e.g., reaction conditions) required for the process being investigated, as discussed in greater detail below with respect to a preferred, diffusion-mixed microreactor design. Nonetheless, the microreactor design parameters can vary substantially, from application to application, to suit particular needs, and still be within the scope of the invention. As such, the following exemplary design parameters are to be considered as non-limiting, except as specifically recited in the claims.

Microreactor volume is defined as the physical volume of the reaction cavity—that is the physical volume of the space in which the reaction (or other chemical process of interest) is allowed to occur. As such, the microreactor volume can be designed, in combination with a volumetric flow rate through the reaction cavity, to obtain a residence time, $\tau_{res}$, sufficient to effect the reaction (or other chemical process) of interest. The microreactor volume can be, in general, less than about 10 ml, less than about 5 ml, less than about 3 ml, and preferably, less than about 1 ml. For many applications, the microreactor volume is even more preferably less than about 100 $\mu$l, yet more preferably less than about 10 $\mu$l, and most preferably about 1 $\mu$l. The volume can range, for example, from about 1 nanoliter (nl) to about 10 ml, preferably from about 1 nl to about 1 ml, more preferably from about 10 nl to about 100 $\mu$l, even more preferably from about 0.1 $\mu$l to about 10 $\mu$l, and most preferably from about 0.5 $\mu$l to about 5 $\mu$l. While a volume of about 1 $\mu$l is suitable for many applications, other volumes may be desired or necessary for certain applications and/or certain reactions.

The microreactor geometry can be of any suitable shape or geometry, but for some designs—such as diffusion-mixed microreactors as described below—is preferably a cell-type microreactor rather than a channel-type microreactor. For purposes herein, the distinction between a cell-type microreactor and a channel-type microreactor can be characterized with respect to a ratio of three distances, X:Y:Z, measured within the reaction cavity along three mutually orthogonal lines having a common point of intersection, where Z is considered, by definition herein, to be the longest distance, where the common point of intersection is the midpoint of the line defining the Z distance, where Z is normal to at least one surface which it intersects, and preferably to two surfaces which it intersects, and where the XYZ coordinates are positioned (e.g., through rotational freedom) such that each of the three distances are maximized, to the extent possible. The XYZ ratios for a variety of common three-dimensional shapes are depicted schematically in FIGS. 11A through 11F. Characterized in this manner, the microreactor geometries are preferably designed such that X:Z and Y:Z ratios each, independently range from about 1:2 to about 1:1. The X:Z and Y:Z ratios each more preferably range, independently, from about 2:3 to about 1:1 and even more preferably from about 3:4 to about 1:1. A most preferred X:Z and Y:Z ratios are each, independently, about 0.9:1. Microreactors having a geometry characterized by such ranges of X:Z and Y:Z ratios can be advantageously employed as diffusion-mixed microreactors, as discussed below.

The inlet and outlet port sizes can vary, depending primarily on reactant flow, on pressure, and for some designs such as diffusion-mixed microreactors, on back-diffusion considerations. Inlet and outlet ports can have dimensions (e.g., length of one side of a square and/or diameter) that range from about 1 $\mu$m to about 2 mm, preferably from about 10 $\mu$m to about 1 mm, and more preferably from about 10 $\mu$m about 100 $\mu$m. In terms of hydraulic radius, the inlet and/or outlet ports can have a hydraulic radius ranging from about 0.125 $\mu$m to about 0.5 mm, from about 0.25 $\mu$m to about 250 $\mu$m, and preferably from about 2.5 $\mu$m to about 100 $\mu$m. The location of the inlet and outlet ports is non-limiting, except that, in preferred embodiments as noted above, they are arranged so that the structural integrity thereof is independent of the material-containing array.

The specific surface area, amount, location and type of candidate materials is also highly process dependent. For heterogeneous catalyst screening, for example, catalyst surface areas can range from about 0.1 m$^2$/g to about 2000 m$^2$/g, and preferably from about 1 m$^2$/g to about 100 m$^2$/g. The amount of catalyst material and location can be varied as discussed above. In preferred applications, in which a film of the candidate material being investigated is formed on a surface which is or becomes a reaction-cavity-defining surface, the candidate material can be comprise from about 1% to about 100% of the reaction-cavity surface. In typical applications, however, the candidate material comprises from about 10% to about 70% of the reaction-cavity surface, and preferably in some cases, from about 20% to about 50 % of the reaction-cavity surface. ps Reaction Conditions Regardless of the particular microreactor design, the plurality of microreactors in a chemical processing microsystem are preferably designed such that the reaction process conditions can be controlled to be substantially identical in each of the plurality of microreactors. Chemical processing microsystems having substantially identical process conditions are particularly suitable for screening a library of different candidate materials—to allow for direct comparison between the different candidate materials at those maintained reaction conditions. In a preferred embodiment, therefore, the plurality of microreactors are substantially identical for each of the microreactors included in chemical processing microsystem.

Alternatively, however, the reaction conditions can be controllably varied amongst the plurality of microreactors—either between one group of microreactors and another group of microreactors, or between each of the plurality of microreactors. Varied reaction conditions can be employed, for example, using an array of different candidate materials in repetitive experiments to determine whether certain reaction conditions favor certain of the candidate materials, or to determine a range of conditions for which certain candidate materials have the property of interest. As discussed below, varying of reaction conditions can also be employed using an array comprising a single material (e.g., catalyst) for process research and optimization. Exemplary reaction conditions that can be readily varied include temperature, pressure and residence times, among others.

Several process conditions are typically of importance in connection with chemical processes, and particularly, in connection with chemical reactions. Such process conditions include primarily, without limitation, temperature, pressure and reactant residence time (e.g., reactant contact time with a catalyst). Selection of such parameters will vary with the particular reaction of interest, and/or for the particular research goals of interest. As such, a person of skill in the art can vary these parameters and others to suit their particular needs, and still be within the scope of the invention. Hence, the following exemplary design parameters are to be considered as non-limiting, except as specifically recited in the claims.

Temperature in a reaction cavity and/or temperature of a candidate material of interest can be controlled by any suitable temperature-control device (e.g., heat transfer apparatus) known in the art for microfluidic applications. While such a device can be integrated into the chemical processing microsystem of the present invention in any suitable manner, the structural integrity of such device is preferably independent of the material-containing array. With reference to FIG. 2 and FIG. 8, for example, a temperature-control block 400 can operate as a heat sink (e.g., to maintain approximately constant temperature during a exothermic reaction), as a heat source (e.g., to maintain approximately constant temperature during an endothermic reaction), or as an insulator (e.g., to provide approximately adiabatic reaction conditions). The temperature-control block 400 can be, for example, a microfluidic heat exchanger (See, for example, U.S. Pat. No. 5,811,062 to Wegeng et al. ), or a microscale resistive heating element. The temperature can be maintained substantially the same in each of the microreactors, or can be varied between groups of microreactors or between each of the microreactors. For example, a temperature gradient can be spatially applied across one or more directions of a material-containing array. As another example, spatially addressable independent heating elements can be used to individually control the temperature of each microreactor (or each candidate material). See, for example, U.S. Pat. No. 5,356,756 to Cavicchi et al. Appropriate microscale temperature-sensing devices, together with a suitable process control system, can also be employed. See, for example, S. M. Sze, *Semiconductor Sensors*, John Wiley & Sons, Inc. (1994).

Pressure in a reaction cavity can be controlled on a microscopic scale by a number of different approaches. For example, the fluid pressure in the reaction cavity can be varied by actively controlling the flow resistance (e.g., with a microscale pressure-control valve) in the supply manifold or in the discharge manifold. In a passive microfluidic distribution system—lacking any active pressure-control components such as valves—pressure considerations are typically factored into the microreactor and distribution system design, by variation of flow conductance of either the supply or discharge manifold. For a system having an established microreactor design and an established passive distribution design, the pressure in the microreactor can be controlled by varying the supply pressure, varying the discharge backpressure and/or varying the reactant flow rates through the distribution system. Pressures can be maintained substantially the same in each of the microreactors, or can be varied for a group of microreactors or for each individual microreactors (for example, by varying the conductance of the distribution channel serving a group of microreactors or each microreactor. Appropriate microscale pressure-sensing devices, together with a suitable process control system, can also be employed. See Sze, Id. In general, for the preferred embodiments of the invention, higher pressures can be achieved by using microreactors formed in bonded, rather than releasably-sealed laminae—especially when the microsystem itself is under atmospheric conditions. Microreactors formed in releasably-sealed laminae can also be employed at higher pressures by placing the entire microsystem into a hyperbaric chamber such that the pressure difference between the reaction cavity and the atmosphere external to the microsystem is within the sealing capabilities of the releasable seal.

Residence time in a reaction cavity can be designed based on microreactor volume and reactant flow rate through the microreactor. Flow rates are, in turn, dependent upon reactor inlet port and outlet port geometries, distribution system geometries and fluid pressures. Residence times can be maintained substantially the same for each of the microreactors or can be varied for a group of microreactors or for each of the microreactors. In one embodiment, a plurality of microreactors suitable for providing varying residence times for different microreactors is provided by fabricating the microreactors with varying volumes. With reference to FIG. 9, for example, the volume of each reactor well 235 could be varied between one group of microreactors and another group, or between each individual microreactor. In an alternative embodiment, a flow-distribution system suitable for providing varying residence times for different microreactors (now having substantially the same volume) is provided by fabricating flow distribution networks having varying flow restriction (and correspondingly varying conductance) between different flow channels such that the flowrates to different microreactors (or sets of microreactors) varies. With reference to FIG. 7B, for example, the total flow restriction of each flowpath could be varied between flowpaths to one group of microreactors and another group, or between flowpaths to each individual microreactor. In any case, appropriate microscale flow-sensing devices, together with a suitable process control system, can also be employed. See Sze, Id.

Figure 12:
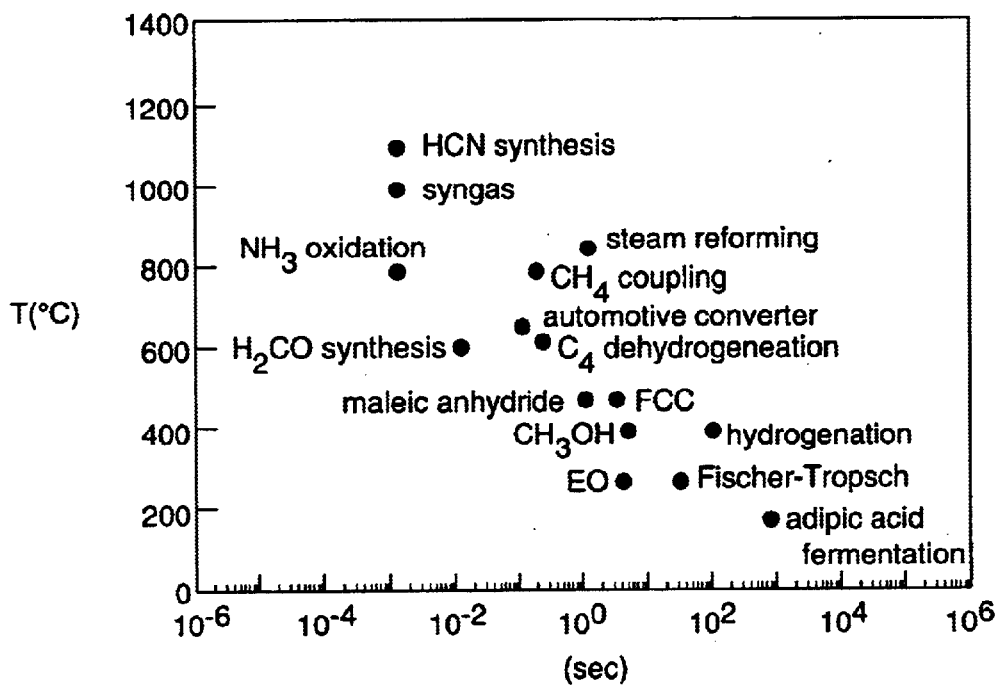
FIG. 12 is a graph showing reaction temperatures and residence (contact) times for effecting various exemplary heterogeneously-catalyzed reactions of commercial significance using known commercial catalysts.

Applicable actual temperatures, pressures and residence times will vary significantly for different processes of interest. Generally, for many chemical reactions of interest, temperatures are preferably above about 100° C., and more preferably above about 200° C. Pressure can generally range from about atmospheric pressure to 200 bar. Exemplary reaction conditions for heterogeneous catalysis applications are as follows. The temperatures for heterogeneous catalysis can typically range from about 0° C. to about 1200° C., preferably from about 25° C. to about 800° C., more preferably from about 100° C. to about 800° C., and most preferably from about 100° C. to about 500° C. Pressures for heterogeneous catalysis can typically range from about atmospheric pressure to about 200 bar, from about atmospheric pressure to about 100 bar, and from about atmospheric pressure to about 50 bar. Vacuum conditions are contemplated for some chemical reactions or other chemical processes (e.g., separations). Residence times for heterogeneous catalysis can range from about 1 μsec to about 1 hr, preferably from about 100 μsec to about 30 minutes, more preferably from about 1 msec to about 15 minutes, and most preferably from about 10 msec to about 2 minutes. FIG. 12 shows the reaction temperature and residence times required for various heterogeneously-catalyzed reactions of commercial significance using known commercial catalysts.

Diffusion Mixed Microreactors—Microreactor Design and Reaction Conditions

In a preferred embodiment, materials that enhance a chemical reaction of interest, such as heterogeneous catalysts, can be identified in a plurality of continuous flow microreactors—where each of the microreactors are designed and the process conditions are controlled such that the residence time, $\tau_{res}$, of reactants in the reaction cavity is sufficient to provide for diffusion mixing thereof, and preferably, without substantial back-diffusion of the reactants through the reactant inlet port.

Diffusion mixing occurs when two or more different fluid molecules are completely mixed by diffusion, without the assistance of active mixing elements (e.g., impellers, motors) and without the assistance of static mixing elements (e.g., turbulence generated by flow through a tortuous-channel). While some localized mixing may occur due to flow (e.g., near a microreactor inlet port), the mixing in the reaction cavity of diffusion-mixed microreactors is ascribable predominantly to diffusion phenomena. In general, diffusion mixing will occur when the microreactor is designed and the process conditions are controlled such that the residence time, $\tau_{res}$, of reactants in the reaction cavity is greater than the diffusion period, $\tau_{diff}$, for the reactants in the reaction cavity. Qualitatively, this suggests that diffusion mixing can occur with relatively long residence times and relatively short diffusion periods—conditions generally achievable with very low flow rates through small, cell-type microreactors (having small diffusion paths).

Figure 11A:
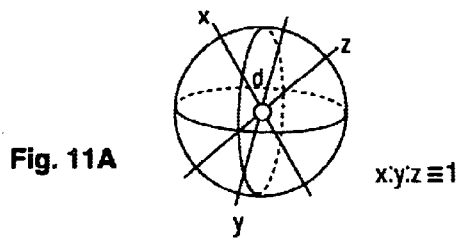
FIG. 11 A through FIG. 11F are perspective views of various three-dimensional geometries having XYZ coordinates superimposed therein, including a sphere (FIG. 11A), a cube (FIG. 1B), a parallel piped (FIG. 11C), a tube (FIG. 11D), a relatively flat cylinder (FIG. 11E) and parallel plates (FIG. 11F).
Figure 11B:
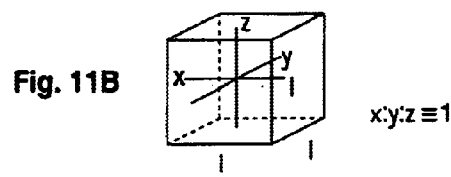
Figure 11C:
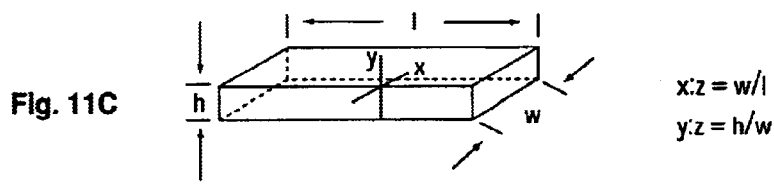
Figure 11D:
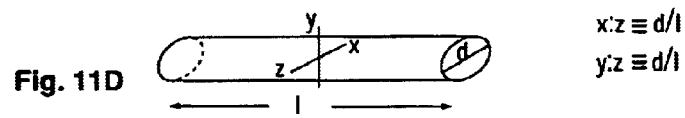
Figure 11E:
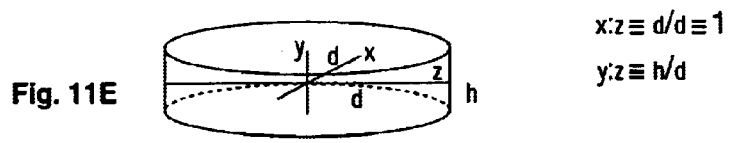
Figure 11F:
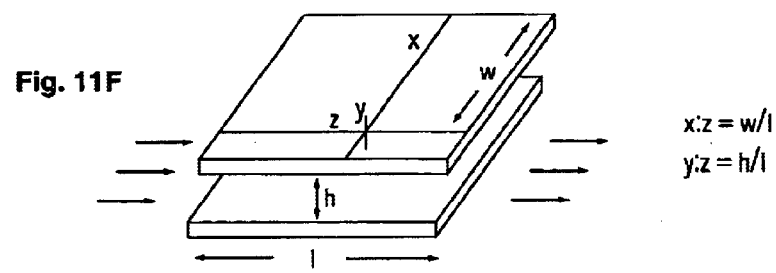

A diffusion-mixed microreactor can be designed by controlling reactor geometry and reaction process conditions. The diffusion period, $\tau_{diff}$, can be defined as the time required for a reactant molecule to diffuse through a mean free path that is equal to the longest path of diffusion, $L_{diff}$, for a particular microreactor design. The longest path of diffusion, $L_{diff}$, can be defined as equal to the longest straight-line dimension for a reaction cavity of a particular geometry. For a relatively flat, circular reaction cavity such as shown in FIG. 11E (and substantially as that shown in FIGS. 9A and 10A), for example, the longest path of diffusion, $L_{diff}$, is the diameter, d. For a long-channel type microreactor, such as is represented by FIG. 11D, the longest path of diffusion, $L_{diff}$, is the length, l. Hence the diffusion period, $\tau_{diff}$, will be a function of the reactant diffusivity, D, and the longest path of diffusion, $L_{diff}$, and can be calculated, based on a one-dimensional model, as set forth in Equation 3a:

$$\tau_{diff} = (L_{diff})^2 / D \qquad \text{Eqn. 3a.}$$

While a one-dimensional model can be satisfactory as a conservative approximation for many reactor geometries, $L_{diff}$, can likewise be calculated, based on a two-dimensional model. Diffusivity, D, is, in turn, dependent upon the particular reactant fluid and the temperature, T, of the reactant fluid within the reaction cavity. As such, both microreactor design parameters and process conditions can affect the diffusion period, $\tau_{diff}$. The residence time, $\tau_{res}$, is a function of reaction cavity volume, V, and reactant flowrate, V, and as such, is likewise dependent upon both microreactor design parameters and process conditions. The residence time can be calculated as shown in Equation 4:

$$\tau_{res} = V / \dot{V} \qquad \text{Eqn. 4}$$

Hence a diffusion-mixed microreactor can be designed by varying reactor geometry (e.g., longest path of diffusion, $L_{diff}$, and/or reaction cavity volume, V) and/or by varying reaction process conditions (e.g., temperature, T, flowrate, V).

In a preferred approach, a diffusion-mixed microreactor can be designed for combinatorial chemistry research purposes directed toward identifying materials as follows. Once the chemical reaction of interest is identified, a target temperature, T, and a target residence time, $\tau_{res}$, can be chosen. These variables can be chosen, for example, based on industry standards, or based on research goals that improve on industry standards by a certain margin. With reference to FIG. 12, for example, temperature and residence time for the heterogeneous catalysis reaction of automobile catalytic converters can be chosen as a target temperature of about 600° C. and a target residence time of about 0.1 seconds (current industry standard) or, alternatively, as a target temperature of about 600° C. and a target residence time of about 0.01 seconds (reduced by factor of ten relative to current industry standard). The diffusivity, D, of the reactants can then be calculated at that known target temperature, T. The longest path of diffusion, $L_{diff}$, is then determined by applying the definitional requirement for diffusion-mixing: that the residence time be greater than the diffusion period ($\tau_{res} > \tau_{diff}$). Substituting from Equations 3a (based on one-dimensional model, for example) and 4, and rearranging yields Equation 5, from which $L_{diff}$ can be calculated:

$$L_{diff} = [(D)(\tau_{res})]^{1/2} \qquad \text{Eqn. 5.}$$

Knowing $L_{diff}$, a reactor geometry can be selected and a reaction cavity volume, V, can then be calculated to provide that $L_{diff}$ based on that geometry. Now knowing V, the required volumetric flowrate, V, can be calculated using Equation 4. The reactor inlet port and reactor outlet port dimensions and distribution manifold particulars can then be designed to provide the required flowrate.

In preferred embodiments, diffusion-mixing occurs without substantial back-diffusion of reactants into the reactant supply manifold. Back-diffusion of the reactant molecules through the reactor inlet port is substantially avoided by ensuring that the flow velocity at the reactor inlet port, $v_{flow}$, is greater than the diffusion velocity, $v_{diff}$. Based on this principle, a reactor inlet dimension (assuming circular cross-section) can be determined from Equation 6:

$$r < [Q(L_{diff})/(D)(\pi)(P)]^{1/2} \qquad \text{Eqn. 6,}$$

where r is the radius of a circular reactor inlet port, Q is the pressure-velocity per unit time and P is the pressure in the microreactor. As explained above, inlet pressure, P, is dependent, in turn, on flow-rate, V, and on the distribution system conductance.

Figure 13A:
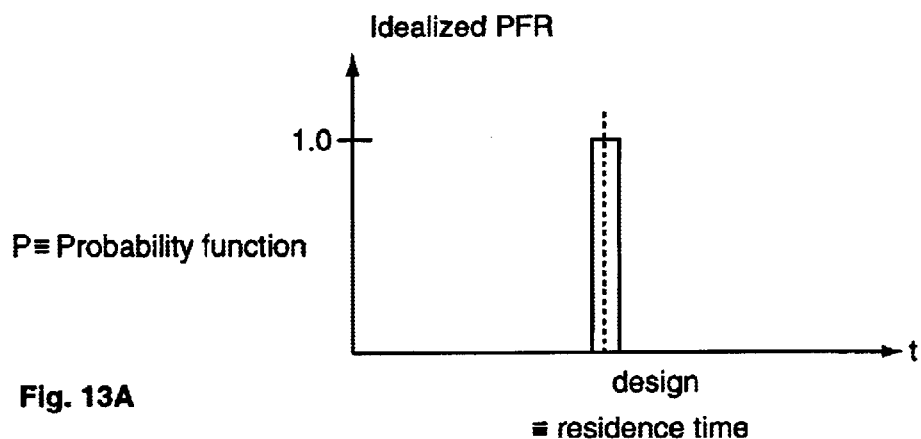
FIG. 13A through FIG. 13C are graphs showing residence-time probability functions for an ideal plug-flow reactor (PFR) (FIG. 13A), for a practical PFR (FIG. 13B) and for a continuous-stirred-tank reactor (CSTR) (FIG. 13C).
Figure 13B:
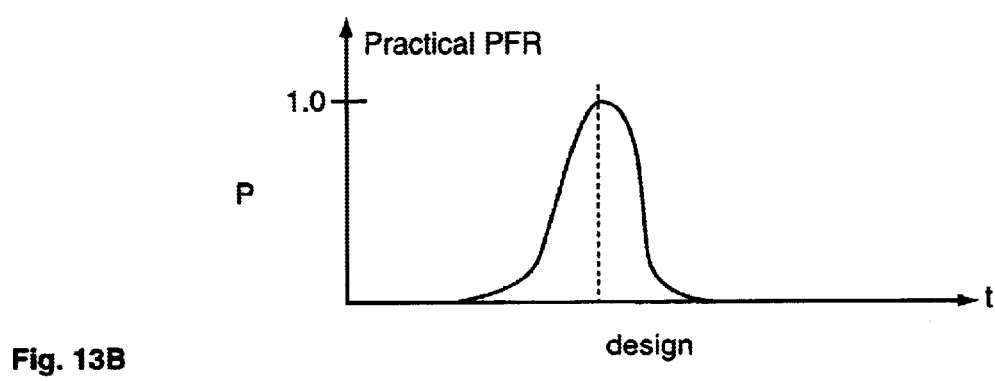
Figure 13C:
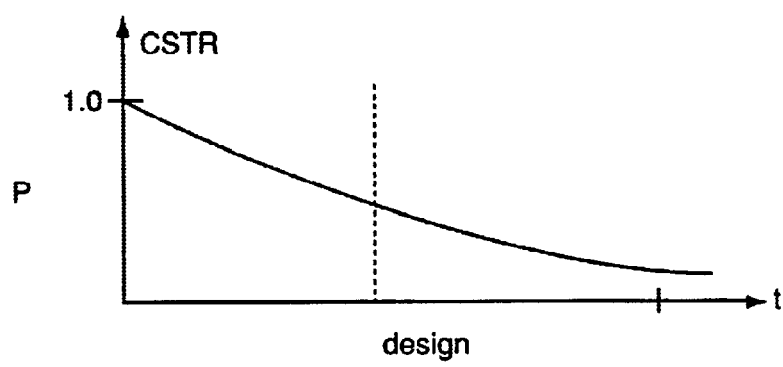

Diffusion-mixed microreactors can model a continuous-stirred-tank reactor (CSTR)—but without any active mixing elements (e.g., impellers, motors) and without any static mixing elements (e.g., a tortuous-channel). As such, a diffusion-mixed microreactor offers substantial advantages over microreactors/reaction conditions designed to model a plug-flow reactor (PFR) in applications directed to identifying new catalysts or other new materials. With reference to FIGS. 13A through 13C, an ideal plug-flow reactor has a residence time distribution function approaching a delta function (FIG. 13A)—that is, each molecule of a reactant sample will have the designed residence time. A non-ideal, (e.g., commercial) plug-flow reactor has a relatively narrow residence time distribution function (FIG. 13B)—such that most of the molecules in the sample will, with high probability, have the designed residence time, but some relatively small number of molecules will reside in the reaction cavity for a time that is less than or more than the designed residence time, but in a narrow time interval with respect to the designed residence time. In contrast, however, a continuous-stirred-tank reactor has a relatively broad residence time distribution function exhibiting an exponential decay (FIG. 13C)—such that, while some of the molecules in the sample will have some probability of residing in the reactor for the designed residence time, many of the molecules in the sample will reside in the reaction cavity for a time that is less than or more than the designed residence time, and in a relatively broad time interval with respect to the designed residence time. The broader range of residence times can be advantageous for combinatorial materials science research, and especially for primary screening approaches, because of the larger process-condition space that is effectively investigated in parallel with a single microreactor design, which could lead to a greater number of primary screen hits in a single screening experiment.

The diffusion-mixed microreactors of the present invention can be applied as single microreactors—for example, for microscale manufacturing, or alternatively, a plurality of such microreactors can be used in a chemical processing microsystem for characterizing or optimizing chemical reaction processes and/or for identifying and optimizing materials (e.g., catalysts) that enhance a chemical process.

Discharging Reactor Effluents from the Microreactors

As noted, the plurality of microreactors are preferably designed to operate as continuous reactors, rather than as batch reactors. As such, the reaction products, if any, and the excess reactants, if any, are discharged, preferably simultaneously discharged, from each of the microreactors. With reference again to FIG. 1A, the reactor effluent stream can be discharged to waste and/or, as discussed below, wholly or at least partially discharged to analytical devices and instrumentation for evaluation of the candidate materials.

The particular design details of a reactor effluent manifold are not, in the general case, of substantial critical significance. In general, the reactor effluent streams can be discharged from the plurality of reactor outlet ports (e.g., outlet port 260 in FIG. 8) as a plurality of independent streams (e.g., as waste streams and/or as analytical sample streams)—without recombining the streams. The reactor effluent streams can, alternatively, be recombined, partially or completely, after discharge from the plurality of microreactors. In any case, many of the design considerations discussed above in connection with the supply of reactants to the plurality of microreactors are also applicable with respect to discharge of the reactor effluent. For example, pressure control can, additionally or alternatively to other pressure-control approaches, be realized through an effluent distribution manifold by providing flow resistance in the effluent flow path. If desired to maintain substantially the same reaction conditions for each microreactor, however, the effluent manifold paths are preferably designed to be symmetrical (i.e., with equal conductance).

Figure 14:
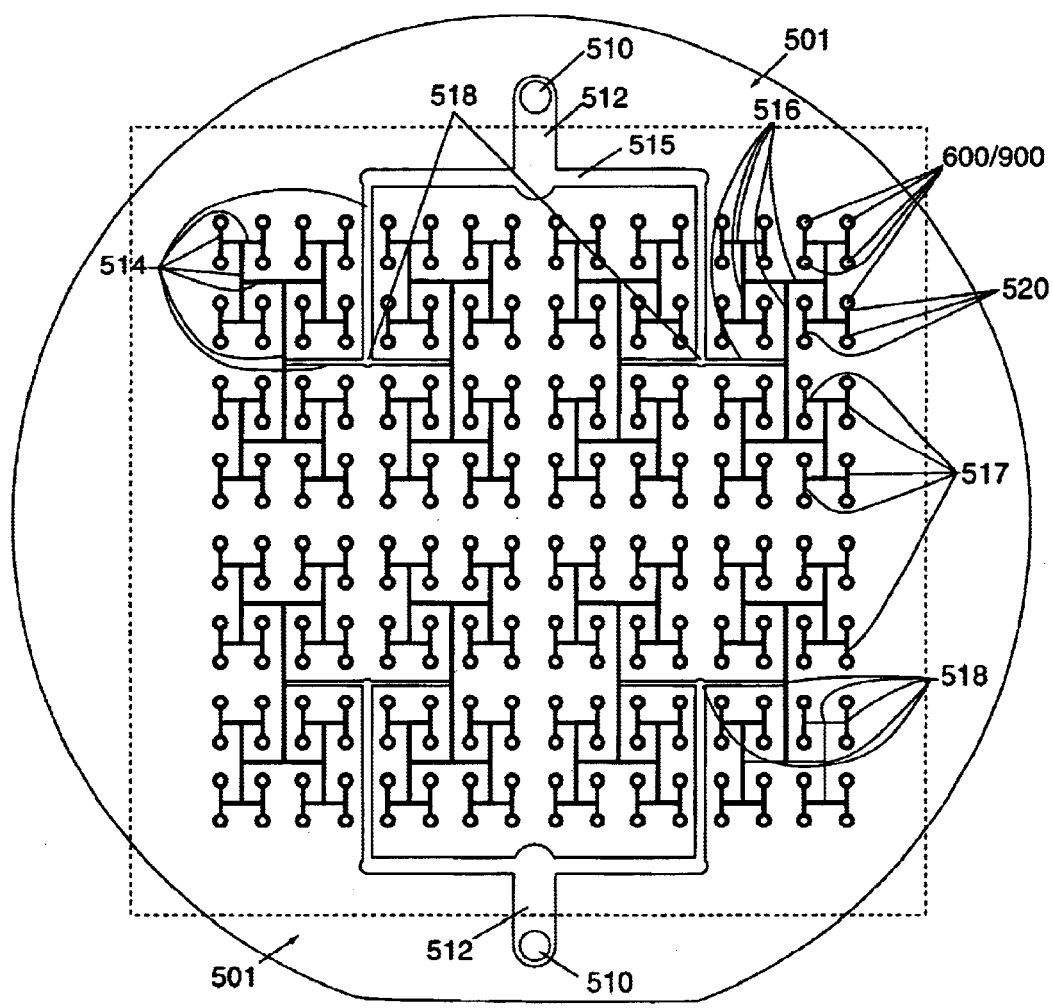
FIG. 14 is a top-plan view of preferred binary-tree distribution manifolds serving an array of 256 microcomponents, suitable for example, for use as a microreactor discharge manifold in connection with the chemical processing microsystem of FIG. 8 or as a microseparator effluent manifold in connection with the chemical processing microsystem of FIG. 18A.

FIG. 14 shows a preferred binary-tree effluent manifold 501 for use in connection with the present invention, in which each of a plurality of microreactors 600 are in fluid communication with a common effluent port 510, and the flow paths from each of the microreactors 600 to common port 510 have equal conductance. The effluent distribution manifold 501 can comprise, more specifically, $2^n$ terminal ports 520 adaptable for receiving fluid the $2^n$ microreactors 600 (or, in the general case, other microcomponents), and a distribution channel (generally indicated as 514) providing fluid communication between each of the $2^n$ terminal ports 520 and the common port 510 (via common header 512). The remaining details of the effluent distribution are, except as noted below, substantially the same as those described in connection with the supply of reactants to the microreactor. As noted above in connection with the supply manifold, the effluent distribution manifold can have a single common port 510 located centrally or near the peripheral edge of the manifold.

In a preferred embodiment, the effluent manifold serves as fluid collection function, but is not used for pressure control. As such, the channel dimensions for each of the distribution channels 514 are approximately the same over the entire flow length of the channel, and the conductance, C, (for rectangular cross-sections having a width, w and height, h, being proportional to $wh^3$ and for aspect ratios of about 1, proportional to approximately $h^4$) for the effluent manifold is about 100 times greater than the conductance, C, of the supply manifold. In a preferred embodiment, therefore, the dimensions of the effluent manifold are approximately 100 $\mu m$ for both height and width.

FIGS. 7G and 7H show alternative embodiments for reactor effluent distribution systems. Briefly, effluent distribution channels 513 (FIG. 7G, FIG. 7H) provide a discharge path for the plurality of microreactors 600. As shown in FIGS. 7G and 7H, the highest pressure drop occurs in the supply distribution channels 514 ("L-shaped"—FIG. 7G, or "binary-tree"—FIG. 7H) rather than in the effluent distribution channels 513. To ensure substantially the same pressure and flow conditions through each of the microreactors 600, the various flow-paths of each of the channels 513 are of the same length and equivalent geometry.

Evaluation of Candidate Materials

The plurality of candidate materials are screened to evaluate their capability to enhance the chemical process of interest. In general, the candidate materials can be screened during the chemical process—either by in situ measurements in the reaction cavity, or by measurements of the reactor effluent stream. The measurements can provide for real-time direct evaluation of the candidate materials, or may, alternatively, provide for an indirect evaluation approach including a real-time storage record of physical evidence or data that can be evaluated at a later time and/or at a remote location. For example, the evaluation of candidate materials can include a real-time separation of one or more components that are indicative of the candidate material performance, with a subsequent quantitative determination thereof. In any case, the analytical system for screening the candidate materials can be wholly integral with the chemical processing microsystem, partially integral therewith, or completely independent therefrom. Integral microcomponents can include, for example, microscale probes and/or microsensors incorporated into the microreactor design, microelectronic control modules integrated into the chemical processing microsystem, and/or microseparators integral with the chemical processing microsystem, as discussed in connection with FIG. 1C. Such systems can be wholly integral, or combined with external instrumentation (e.g., detectors).

The particular approach employed for screening the candidate materials can vary substantially, depending on the type of chemical process and the enhancing property being evaluated. For chemical reactions, for example, analytical measurements can determine the extent of the reaction (e.g., by considering product yield or reactant consumption), the rate of the reaction (i.e., kinetics), the extent or rate of any side reactions, and properties as catalytic activity (i.e., turnover), selectivity in converting reactants into desired products, and stability during operation under a wide variety of substrate concentrations and reaction conditions. Spatially selective characterization methods include, for example, those capable of: (i) identification and characterization of gas phase products and volatile components of the condensed phase products; (ii) identification and characterization of condensed phase products; and (iii) measurement of physical properties of the catalyst elements. Similar high throughput methodologies can be used for measuring properties of other than catalytic reactions.

Many different approaches and equipment configurations can be employed to effect screenings of the array of candidate materials. In one embodiment, for example, each microreactor effluent stream can be detected by discharging each reactor effluent stream directly to a detector—in rapid-serial fashion (e.g., using a single detector), in serial-parallel fashion (e.g. serially employing a group of parallel detectors, where the group number is less than the number of candidate materials to be evaluated), or in wholly parallel fashion (e.g., using parallel detectors to screen each of the microreactions at the same time). The detectors for gaseous reaction effluents can include, for example, mass-spectrometers (e.g., capillary mass-spectrometers) or gas chromatographs (e.g., especially rapid gas chromatography approaches, such as those employing capillary bundles). In another embodiment, reaction products or quantitatively representative samples thereof may be selectively separated and collected from the reactor effluent stream by chromatographic techniques (e.g. thin-layer chromatography plates; adsorption onto adsorbent media), and then subsequently evaluated. As yet another approach for separating and collecting gaseous reactant products for evaluation, such products can be condensed (collectively, or in some applications, selectively) on a cold substrate, and then subsequently evaluated.

Regardless of the approach or the equipment employed (i.e., whether mass spectroscopy or gas chromatograph, etc., and whether parallel or serial, etc.), the evaluating of a particular candidate material preferably has an overall throughput of at least about 1 candidate material/five minutes, more preferably at least about 1 candidate material/2 minutes, and most preferably at least 1 candidate material/minute, or faster. Substantially higher screening throughputs can be achieved using parallel analytical measurement approaches. As such, the overall time required to identify materials having a reaction-enhancing property, more specifically defined as a difference in time, $t_1-t_2$, measured as the time required to load the at least four candidate materials into the four or more microreactors (such loading commencing at a time $t_1$), to supply one or more reactants to the four or more material-containing microreactors, to contact the at least four candidate materials with the one or more reactants under conditions whereby the chemical reaction, if any, is effected, to discharge the reactor effluents, and to evaluate the at least four candidate materials for catalytic activity (such evaluating being completed at a time $t_2$), being less than about 3 hours. The difference in time, $t_1-t_2$, is preferably not more than about 1 hr, more preferably not more than about 30 minutes, and even more preferably not more than about 15 minutes. Hence, the overall candidate-material throughput (e.g. for catalytic activity) can be, depending on how many candidate materials are evaluated in parallel, not less than about 1 candidate material/hour, not less than about 10 candidate materials/hour, more preferably not less than about 100 candidate materials/hour, even more preferably not less than about 1000 candidate materials/hour, and most preferably not less than about 1 candidate material/second.

With reference to FIG. 1C, a preferred screening approach for characterizing chemical reactions is based on separation of one or more reaction products (or, less preferably, of unreacted reactants) from each microreactor effluent stream, preferably by means of a microseparator 900 that is integral with the chemical processing microsystem 10, followed by detection of the separated component, preferably by a detection system 1000. While the detection system 1000 could also be integrated with the chemical processing microsystem 10, it is preferably configured external thereto and independent therefrom, to provide for maximum flexibility with respect to available detection approaches.

In a preferred embodiment, the separation of one or more reactor effluent components is accomplished based on adsorption principles. Such a component (e.g., reaction products) can be selectively adsorbed onto an adsorbent media, and subsequently determined. The reactant products for each of the microreactors are preferably adsorbed simultaneously, in parallel, onto the adsorbent material. The adsorbent material and the process of adsorption can be integral with or separate from the chemical processing microsystem. Likewise, the analytical equipment and the process of determining reaction products can likewise be integral with or separate from the chemical processing microsystem. In a preferred approach, however, a plurality of adsorbent materials and the process of adsorption are integrated with the plurality of microreactors, but the determination of reaction products and the analytical equipment employed in such determination are independent of the chemical processing microsystem. The details of a preferred embodiment are presented below. Such an approach offers substantial flexibility with respect to the evaluation of candidate materials, and improves overall screening throughput.

The adsorbent media can be any adsorbent material that is selective for one or more particular reaction products, and/or particular unreacted reactants of interest. A wide variety of adsorbents are known in the art, for example, for use with thin-film chromatography, thermal desorption and other chemical separations. Exemplary adsorbent materials include silica gel (e.g., for selective adsorption of aniline and/or phenol over benzene), activated charcoals, graphitized carbon blacks, carbon molecular sieves and porous or non-porous polymers. (See, generally for example, SUPELCO catalog re "adsorbents"). The degree of selectivity of the adsorbent material over the background materials should be sufficient to be of value with respect to the type of screening at issue. For example, while a fairly quantitatively sensitive selectivity may be desired for a secondary screen, a relative less quantitative screen may be suitable for primary screen. The adsorbent material can be a composition that includes, in addition to a selective separation media, one or more indicators (e.g. dyes) for an analyte of interest.

The plurality of adsorbent materials are preferably supplied to the chemical processing microsystem as an array of adsorbent materials. An array of adsorbent materials generally comprises a substrate and one (or more) different adsorbent materials at separate portions of the substrate. The adsorbent materials may be located at discrete, individually addressable regions of the substrate or, alternatively, may be contiguous with each other. The substrate material is selected to be suitable for support of the adsorbent, and is also preferably selected for suitability in connection with microfabrication techniques. Silicon, including polycrystalline silicon or single-crystal silicon, and silica ($SiO_2$) are preferred substrate materials. The substrate is preferably, but not necessarily, a substantially planar substrate, and the adsorbent materials are preferably, but not necessarily, arranged on the substrate in a substantially co-planar relationship with each other.

Figure 15A:
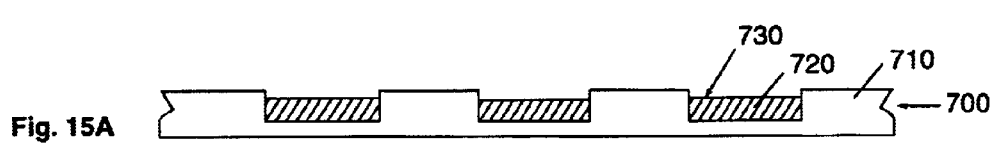
FIG. 15A through FIG. 15C are partial cross-sectional side views showing exemplary configurations of arrays of adsorbent materials. As shown, adsorbent materials are formed as one or more films on various exposed surfaces of a substrate without temperature control (FIG. 15A), with a temperature-control block (FIG. 15B) or with dedicated heating elements (FIG. 15C).
Figure 15B:
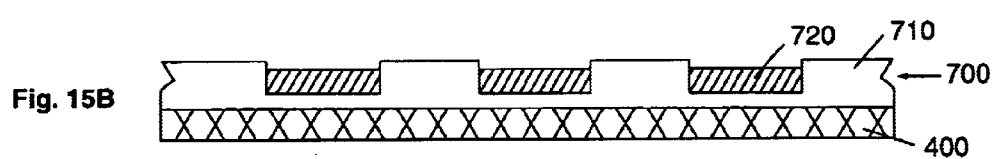
Figure 15C:
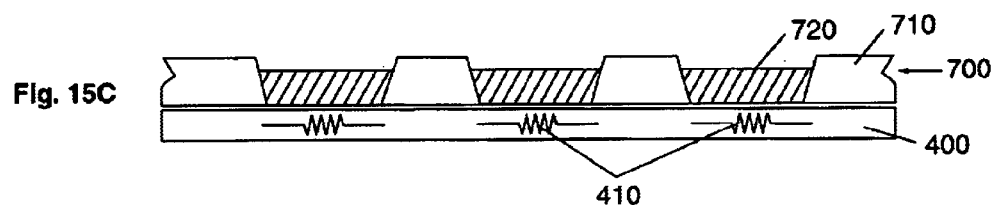

The adsorbent media can have a number of different configurations relative to the plurality of microreactors. For example, each microreactor effluent stream can be passed over, around or through independent adsorbent media supported by independent substrates. The adsorbent media can alternatively be configured relative to the plurality of microreactors as a contiguous thin film over a single substrate, with the reactor effluent from each microreactor passing over, around or through different spatially addressable portions of that single film. Preferably, however, the reactor effluent stream of the plurality of microreactors is simultaneously passed over a plurality of individually addressable adsorbent media, each of which is located on an isolated region that spatially corresponds to a particular microreactor. The particular configuration for the adsorbent media is not limiting, and can include films, packed wells, porous (flow-through) adsorbents, and microparticles (generally analogous to the many configuration options for the candidate material—reference FIG. 3A through FIG. 5). Referring now to FIG. 15A, for example, an adsorbent-material array 700 comprises an adsorbent material 720 on various regions of a substrate 710. The various regions are preferably delineated by wells (indicated generally as 730) that can be formed in the substrate 710 using microfabrication techniques known in the art. The adsorbent material 720 is preferably the same at each region, but could be a different adsorbent material at two or more different regions. Temperature control for the adsorption (and subsequently for desorption) can be achieved, for example by use of a temperature-control block 400 (FIG. 15B). The temperature of each of the adsorbent-material regions can be controlled to be the same or varied (e.g., in a temperature gradient), and can be controlled collectively as shown, for example, in FIG. 15B, or individually as shown, for example, in FIG. 15C (e.g., with individual microscale resistive heating elements 410 integral with the temperature-control block 400). The amount and/or thickness of the adsorbent material should be suitable for the separation application to which it is directed. Typically, such adsorbent materials 720 can be formed as a film or deposited into a well on the substrate 710, and the film or well-deposited adsorbent can have an average thickness ranging from about 5 $\mu$m to about 15 mm, preferably from about 10 $\mu$m to about 5 mm, and more preferably ranging from about 50 $\mu$m to about 1 mm. Approaches for forming such adsorbent materials and/or depositing them on a substrate as a film or in a well are known in the art. In an exemplary approach, an adsorbent material (e.g., silica gel) can be formed on a substrate as taught in copending U.S. patent application Ser. No. 09/149,586, filed Sep. 8, 1998 by Desrosiers et al. Indicator reagents or other imaging agents can, where appropriate for the particular chemistry involved, be pre-dispersed within the adsorbent. The amount of adsorbent material deposited on a particular portion of the adsorbent array 700 is not limiting, and will vary depending upon the required surface area and the required sorbent mass, each of which will, in turn, vary depending upon the chemical reaction of interest and the geometry of the array 700. While the adsorbent materials are preferably formed on a plurality of regions that are coplanar with each other, alternative, non-planar geometries can also be employed.

In a preferred configuration, the adsorbent materials are spatially separated at an exposed surface of the substrate, and arranged such that the array of adsorbent materials can be integrated with the chemical processing microsystem to efficiently access each of the plurality of reactor effluents from each of the microreactors. As such, the number of different regions of an adsorbent material on an array preferably corresponds to the number of microreactors in the chemical processing microsystem. Specifically, the number of adsorbent-material containing regions on an adsorbent array can be one for a single microreactor, but is more typically at least 2, preferably at least 4 or at least 5, more preferably at least 10, still more preferably at least 25, even more preferably at least 50, yet more preferably at least 100, and most preferably at least 250. Present microscale and nanoscale fabrication techniques can be used, however, to prepare adsorbent arrays having an even greater number of different adsorbent-material-containing regions. For higher throughput operations, for example, the number of regions having adsorbent materials can be at least about 1000, more preferably at least about 10,000, even more preferably at least about 100,000, and most preferably at least about 1,000,000 or more. The separation of adsorbent-material-containing regions on the substrate, as well the planar density thereof, can likewise correspond to the separation and planar density of the microreactors and candidate-material arrays, as set forth above. Specifically, the separation between adjacent regions of adsorbent material can range from about 50 $\mu$m to about 1 cm, more preferably from about 100 $\mu$m to about 7 mm, and most preferably from about 1 mm to about 5 mm. The inter-region spacings can be not more than about 1cm, not more than about 7 mm, not more than about 5 mm, not more than about 4 mm, not more than about 2 mm, not more 1 mm, not more than about 100 $\mu$m, and not more than about 50 $\mu$m. Exemplary inter-regions spacings (center-to-center) based on preferred embodiments of the invention are 4 mm for having 256 addressable regions on a three-inch wafer substrate, and 2 mm for having 1024 addressable regions on a three-inch wafer substrate. As such, the surface density of discrete adsorbent material regions can range from about 1 region/$cm^2$ to about 200 regions/$cm^2$, more preferably from about 5 regions/$cm^2$ to about 100 regions/$cm^2$, and most preferably from about 10 regions/$cm^2$ to about 50 regions/$cm^2$. The planar density can be at least 1 region/$cm^2$, at least 5 regions/$cm^2$, at least 10 regions/$cm^2$, at least 25 regions/$cm^2$, at 50 regions/$cm^2$, at least 100 regions/$cm^2$, and at least 200 regions/$cm^2$. For some reactions, lower or mid-range densities may be preferred. For other reactions, higher densities may be suitable. Additionally, even higher densities may be achieved as fabrication technology develops to nano-scale applications. As discussed below, the arrangement of the plurality of adsorbent materials (including separation and relative spatial address) and the plurality of regions should be correlated with the arrangement of microreactors for integration therewith.

In one embodiment, the array of material consists of, or alternatively, consists essentially of, a substrate and adsorbent materials at separate portions of the substrate. Preferably, the array of adsorbent materials consists essentially of the substrate and the adsorbent at the plurality of adsorbent-containing regions. As used in this context, the phrase "consists essentially of" is intended to exclude other microcomponents such as microreactors, valves, active mixers, fluid supply manifolds, etc, without excluding structure whose function is merely to hold an adsorbent material in a particular position or to confine an adsorbent material to a particular space. For example, the adsorbent material could be provided as microparticles using frits to hold such microparticles in place. In such instances, if the adsorbent array does not contain other microcomponents, the array is still considered to "consist essentially of" the substrate and adsorbent.

Figure 16A:
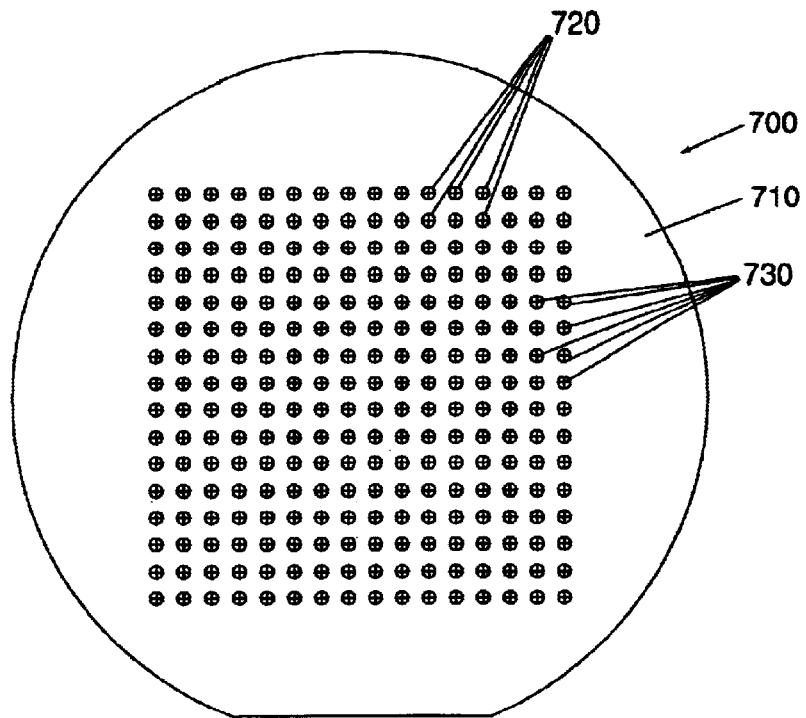
FIG. 16A through FIG. 16E show various configurations for arrays of adsorbent materials.
Figure 16B:
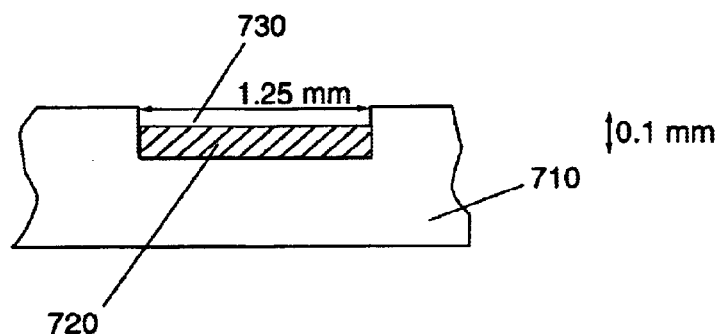

In a preferred embodiment, an array of adsorbent materials, such as silica gel, are deposited onto a substantially planar substrate having a plurality of substantially co-planar wells formed at one surface of the substrate. With reference to FIG. 16A and 16B, an adsorbent array 700 comprises 256 circular-shaped wells 730 arranged in a sixteen-well by sixteen-well square array, with each well having a diameter of about 1.25 mm and a depth of about 0.1 mm. The distance between wells is about 4 mm. The preferred well-containing substrate 110 can be formed, for example, using photolithographic microfabrication techniques known in the art. The adsorbent material(s) can then be deposited in each of the wells to form the adsorbent containing array 700. In an alternatively preferred embodiment, the adsorbent array comprises adsorbent material(s) on up to 1024 regions of a substrate having 1024 wells arranged in a 32-well by 32-well square array. Such an adsorbent array can be prepared, for example, as described above in connection with the 256-well array, except that the distance between wells is reduced to about 2 mm.

Figure 17A:
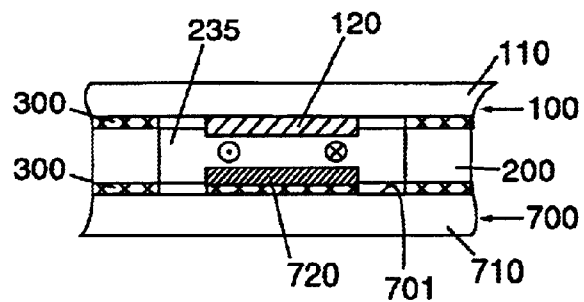
FIG. 17A and FIG. 17B are partial cross-sectional side views showing a alternatives with respect to the geometry with which an array of adsorbent materials and an array of candidate materials can be integrated with other laminae to form an array of candidate-material loaded and adsorbent-material containing microreactors.
Figure 17B:
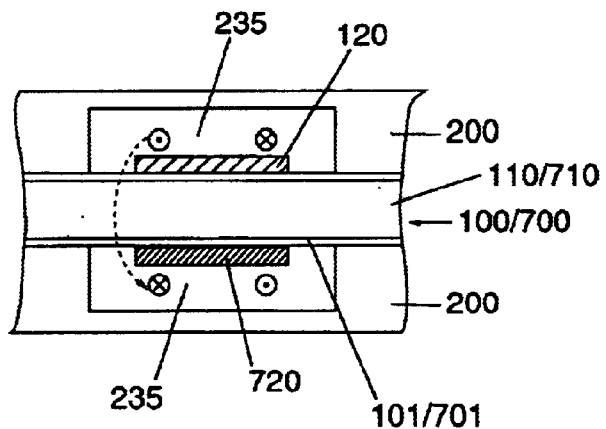

As noted, the array of adsorbent materials is preferably integrated with the chemical processing microsystem. The adsorbent materials can be integrated directly with the microreactors, for example, as shown in FIGS. 17A and 17B. Briefly, the adsorbent array 700 can be integral with the microreactors such that a first surface 701 of the adsorbent array 700, together with an exposed surface of the adsorbent material 720 can form a portion of the surface that defines the reaction cavity. (FIG. 17A, FIG. 17B). The candidate materials 120 and adsorbent materials 720 can be formed on different substrates 110, 710 and both exposed to the reaction cavity (FIG. 17A), or can, alternatively, be formed on opposing surfaces of the same substrate 110/710 with the candidate material 120 exposed to the reaction cavity and the adsorbent material 720 exposed to a separate separation cavity, with fluid communication between the reaction cavity and the separation cavity (FIG. 17B). These approaches are generally suitable when the adsorbent materials and the substrate are inert with respect to the chemical process of interest, are inert with respect to the candidate materials being screened, and are compatible with the reaction conditions employed to effect the chemical process of interest.

More preferably, however, the adsorbent materials are integrated with the chemical processing microsystem independent of, and without affecting the structural integrity of, the microreactors and/or microcomponents thereof. With reference to FIG. 1C, the modular, structurally independent design of the array of adsorbent materials, allows the adsorbent array 700 to be efficiently loaded to the chemical processing microsystem 10, contacted with the reactor effluent stream and subsequently unloaded from the chemical processing microsystem 10. The microsystem 10 can then, if desired, be reloaded with another adsorbent array 700'. Hence, the adsorbent array 700 is preferably interchangeable with the chemical processing microsystem without affecting the structural integrity of the microreactors and/or fluid supply manifold, fluid distribution manifold, heat transfer components, etc.

Figure 18A:
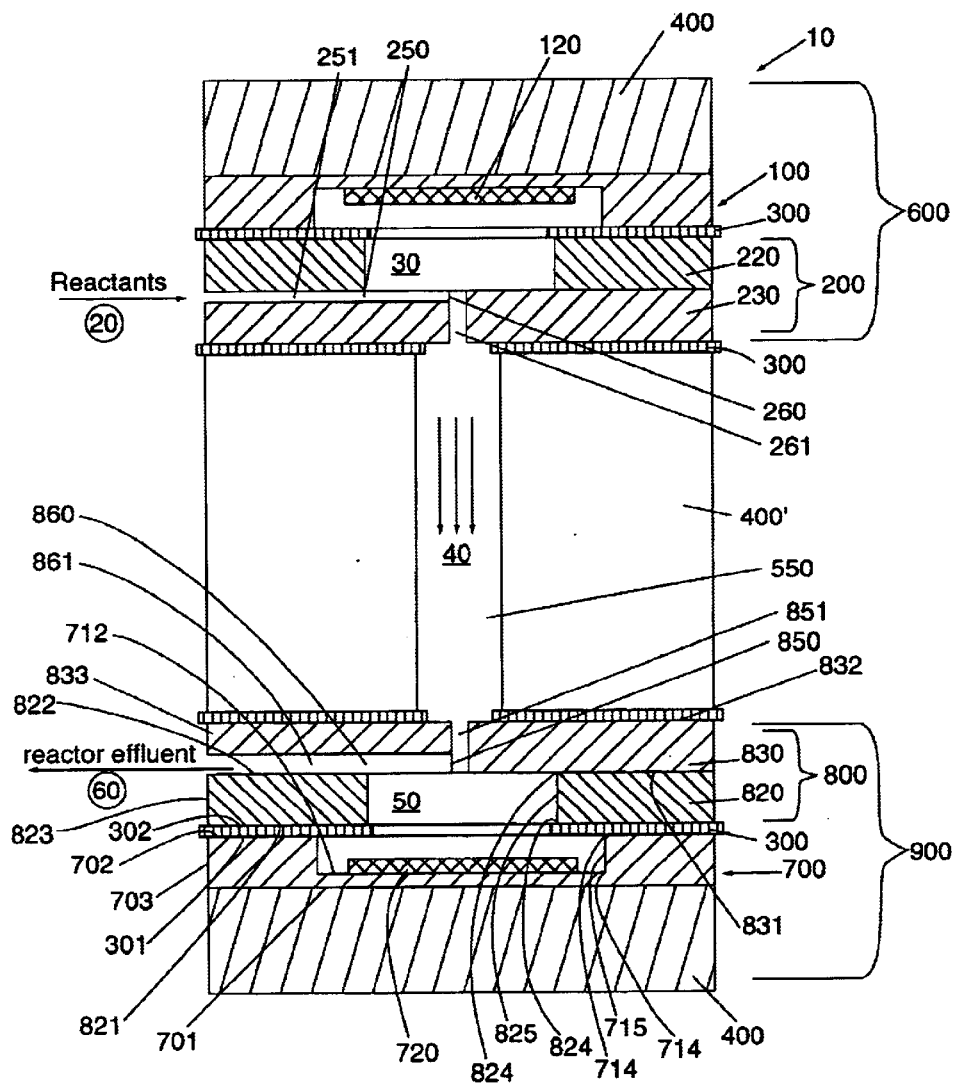
FIG. 18A through FIG. 18J show several embodiments for a chemical processing microsystem.

Referring to FIG. 18A, in a most preferred embodiment, a chemical processing microsystem 10 comprises a plurality of microreactors 600 formed in a plurality of laminae that include an interchangeable candidate-material array 100 and, integral therewith, a plurality of microseparators 900 formed in a plurality of laminae that include an interchangeable adsorbent array 700. The microreactor 600 is substantially the same as that shown in FIG. 8 and described in connection therewith. (As shown in FIG. 18A, however, the microreactor 600 is inverted relative to as shown in FIG. 8.) A microseparator 900 is formed in a plurality of laminae comprising an (adsorbent-containing) first laminate 700, and a composite separator block 800 comprising a (separator) second laminate 820 adjacent to the adsorbent-containing first laminate 700 and a (capping) third laminate 830 adjacent the separator second laminate 820. A releasable seal 300 is preferably situated between the adsorbent-containing first laminate 700 and the separator second laminate 220.

More specifically, with reference to FIG. 18A, the adsorbent-containing first laminate 700 has a first surface 701, a second surface 702 in spaced, substantially parallel relationship to the first surface 701, and a circumferential edge 703. The separator second laminate 820 has a first surface 821 in releasable contact with the second surface 702 of the first laminate 700, a second surface 822 in spaced, substantially parallel relationship to the first surface 821, and a circumferential edge 823. The capping third laminate 830 has a first surface 831 bonded to the second surface 822 of the separator second laminate 820, a second surface 832 in spaced, substantially parallel relationship to the first surface 831, and a circumferential edge 833. The separator second laminate 820 further comprises interior edges 824 and interior surface 825 defining an aperture (with corresponding void space) in the second laminate 820, such that, taken together, the second and third laminates 820, 830 form a composite substructure, separator block 800, comprising a well defined by the interior edge 824 and interior surface 825 of the second laminate 820 and those portions of the first surface 831 of the third laminate 830 circumscribed by such interior edge 824. The adsorbent-containing laminate 700 is preferably releasably engaged with at least one of the adjacent laminates, and preferably, with at least the separator block 800. The releasable contact between the separator second laminate 820 and the adsorbent-containing first laminate 700 is preferably provided by a releasable seat 300 such as a gasket or other suitable releasable-sealing means. The adsorbent-containing laminate 700 is also preferably in releasable contact with (and releasably engaged with) a surface of any other adjacent laminate, such as the temperature-control block 400.

The adsorbent-containing laminate 700 further comprises an adsorbent material 720 effective for separating at least one component of the reactor effluent stream (e.g., reaction product or unreacted reactants). The candidate material 720 can be formed on an exposed surface of the first laminate 700—as shown in FIG. 18A, on a surface 712 of a well formed in the adsorbent-containing first laminate 700. The well in the adsorbent-containing laminate is defined by material-containing surface 712, interior edges 714 and interior surface 715. Taken together, the first, second and third laminates 700, 820, 830 form a microseparator separation cavity defined by the interior edges 824 and interior surface 825 of the second laminate, by the interior edges 714, interior surface 715, adsorbent-containing surface 712 and the adsorbent material 720 of the first laminate 700, and by those portions of the third laminate 830 circumscribed by the interior edges 824 of the second laminate 820.

For fluid distribution within the chemical processing microsystem 10, the microreactor 600 comprises a reactor inlet 250 formed as a microfluidic channel 251 between the second and third laminates 220, 230, and a reactor outlet port 260 formed as the terminal portion of a microreactor outlet channel 261 having an interior surface defining an aperture in the third laminate 230. The inlet 250 is preferably in fluid communication with a microfluidic supply manifold, such as that shown in FIG. 7B and described in connection therewith (with the microfluidic channel 251 of FIG. 18A corresponding to a terminal channel section 517 of FIG. 7B). The microreactor outlet port 260 is in fluid communication with the separator inlet port 850 by means of microreactor outlet channel 261, connecting channel 550, and separator inlet channel 851. The connecting channel 550 can be of any suitable geometry (e.g., shape and/or length) to facilitate communication between each of the plurality of microreactors 600 and each of the plurality of corresponding microseparators 900. The separator inlet port 850 is in fluid communication with the separation cavity for supplying the reactor effluent stream to the microseparator. Inlet port 850 is formed as the terminal portion of the microseparator inlet channel 261 having an interior surface defining an aperture in the third laminate 830. The separator outlet port 860 is in fluid communication with the separation cavity and is formed as the terminal portion of a microfluidic separator outlet channel 861. The outlet channel 861 can be formed as a microfluidic channel between the second and third laminates 820, 830. The microseparator outlet channel 861 is preferably in fluid communication with a microfluidic discharge manifold, such as that shown in FIG. 14 and described in connection therewith (with the microfluidic outlet channel 861 of FIG. 18A corresponding to a terminal channel section 517 of FIG. 14).

The microseparator, such as that shown in FIG. 18A, may further comprise one or more ports (not shown) for analytical microinstruments (e.g., temperature and/or pressure monitoring) and/or for process control elements (e.g., pressure-relief valves). The microseparator may also comprise one or more temperature-control blocks 400, 400'. The temperature-control blocks 400, 400' can be a cooling block, a heating block or an insulator. As discussed above, the temperature of the temperature-control blocks can be controlled to maintain the same temperature for the plurality of microreactors, or alternatively, to provide a different temperature a plurality of microreactors. Moreover, control of the temperature can be collective and or individual to each microseparator. The temperature control block 400 associated with the microreactors is as described above in connection with FIG. 8. The temperature-control block 400 associated with the microseparators can be employed as a cooling-block during adsorption of components from the reactor effluent stream, and subsequently, after removal of adsorbent-containing laminate 700 with adjacent temperature-control block 400, as a heating-block to facilitate desorption therefrom. Because, in many applications, the reaction temperature can differ from the adsorption temperature substantially—up to and, for some reactions, in excess of several hundred degrees Celsius—it may be preferred to provide for independent temperature control of the microreactors and the microseparators. In one approach for such independent temperature control, the microreactors 600 and the microseparators 900 have independently-controlled temperature-control blocks 400 associated therewith. These subsystems can be thermally isolated from each other by temperature control block 400', situated between and in releasable contact with the composite separator block 800 and the composite reactor block 200. The temperature control block 400' is preferably a cooling block or an insulator block suitable, for example, to provide for or allow for cooling of the reactor effluent stream as it passes through the connecting channel 550 and before it reaches the separation cavity, such that the temperature suitable for selective adsorption onto the adsorbent material 720 can be independently controlled from the reaction temperature.

A plurality of microseparators, such as the preferred embodiment shown in FIG. 18A, can be fabricated in a plurality of laminae using microscale and nanoscale fabrication techniques known in the art. The particular details of such fabrication are, in large part, analogous as described above for fabrication of the microreactors 600. For example, the separator block 800 can be fabricated in a manner analogous to the methods disclosed with reference to FIGS. 9 and 10.

In operation, with reference to FIGS. 18A, one or more reactants 20 are simultaneously supplied to a plurality of microreactors 600 through a supply distribution manifold and supply inlet channel 251 and inlet port 250. The one or more reactants 20 are preferably diffusion-mixed in the reaction cavity and simultaneously contacted with each of the candidate materials 120 under process conditions conducive to (or intended to, for research purposes) effect the chemical reaction of interest in each microreactor 600 to form one or more reaction products 30. The reaction products 30, as well as any unreacted reactants 20, are discharged from each reaction cavity through each microreactor outlet port 260 and discharge channel 261 as reactor effluent streams 40. The reactor effluent streams 40 are cooled as they pass through the connecting channel 550, and are then simultaneously supplied to the plurality of microseparators 900 through separator inlet channel 851 and inlet port 850. The reactor effluent stream 40 is resident in the separator cavity and in contact with adsorbent material 720 for a period of time sufficient to simultaneously adsorb a quantitatively detectable amount of at least one analyte component (e.g., reaction product or unreacted reactant) of the reactor effluent stream 40. Such separator residence times will vary with the chemistry involved, but can typically range from about 1 $\mu$sec to about 1 hr, preferably from about 100 $\mu$sec to about minutes, more preferably from about 1 msec to about 15 minutes, and most preferably from about 10 msec to about 2 minutes. The separated effluent stream 50 is then simultaneously discharged from the separation cavity through separator outlet port 260 and outlet channel 261 and through a discharge manifold.

Although it is generally preferred (as shown in FIG. 18A) that the plurality of microreactors 600 are formed in a first plurality of laminae 100, 200, 300 and that the plurality of microseparators 900 are formed in a second, independent plurality of laminae 700, 300, 800, these microcomponents can, in an alternative embodiment, be formed in a common plurality of laminae. With reference to FIG. 7G, for example, an array of thirty-two microreactors 600 and thirty-two microseparators 900 are formed in a common plurality of laminae to be substantially coplanar with each other. FIG. 7H shows an array of 128 microreactors 600 and 128 microseparators 900 formed in a common plurality of laminae to be substantially coplanar with each other. The plurality of laminae can, in either case, be substantially as shown in FIG. 8, except that candidate material 120 (FIG. 8) will be included in the microreactors 600, whereas an adsorbent material 720 (FIG. 18A) will be included in the microseparators 900. Referring now to both FIGS. 7G and 7H, reactants are supplied to the plurality of microreactors 600 and the reactor effluent is discharged therefrom as described above. The reactor effluent is then communicated to the plurality of microseparators 900 by connecting channels 550. The separated reactor effluent stream can be discharged through outlet channels 861, common outlet headers 862 and common outlet port 863.

Figure 18B:
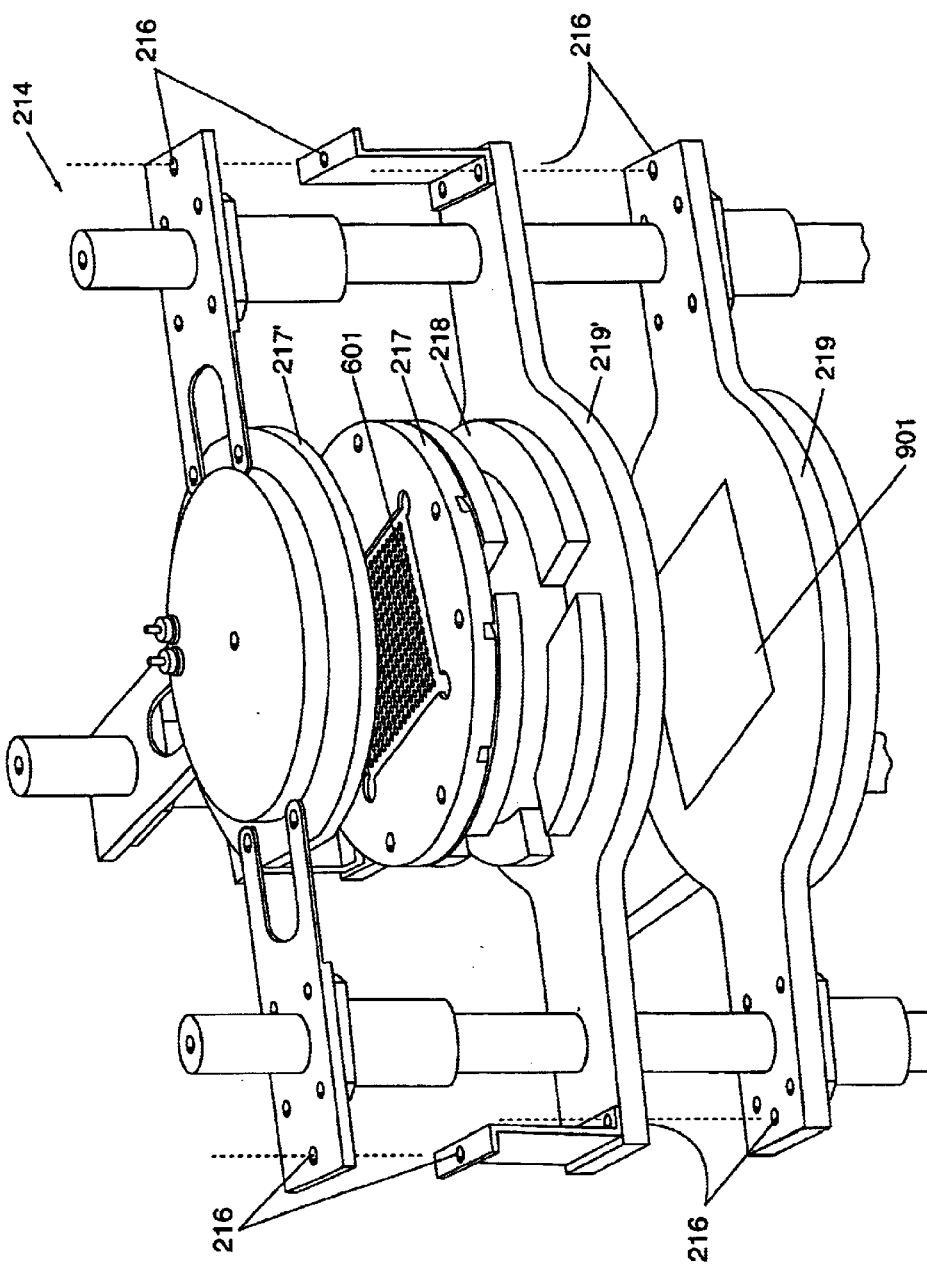
Figure 18C:
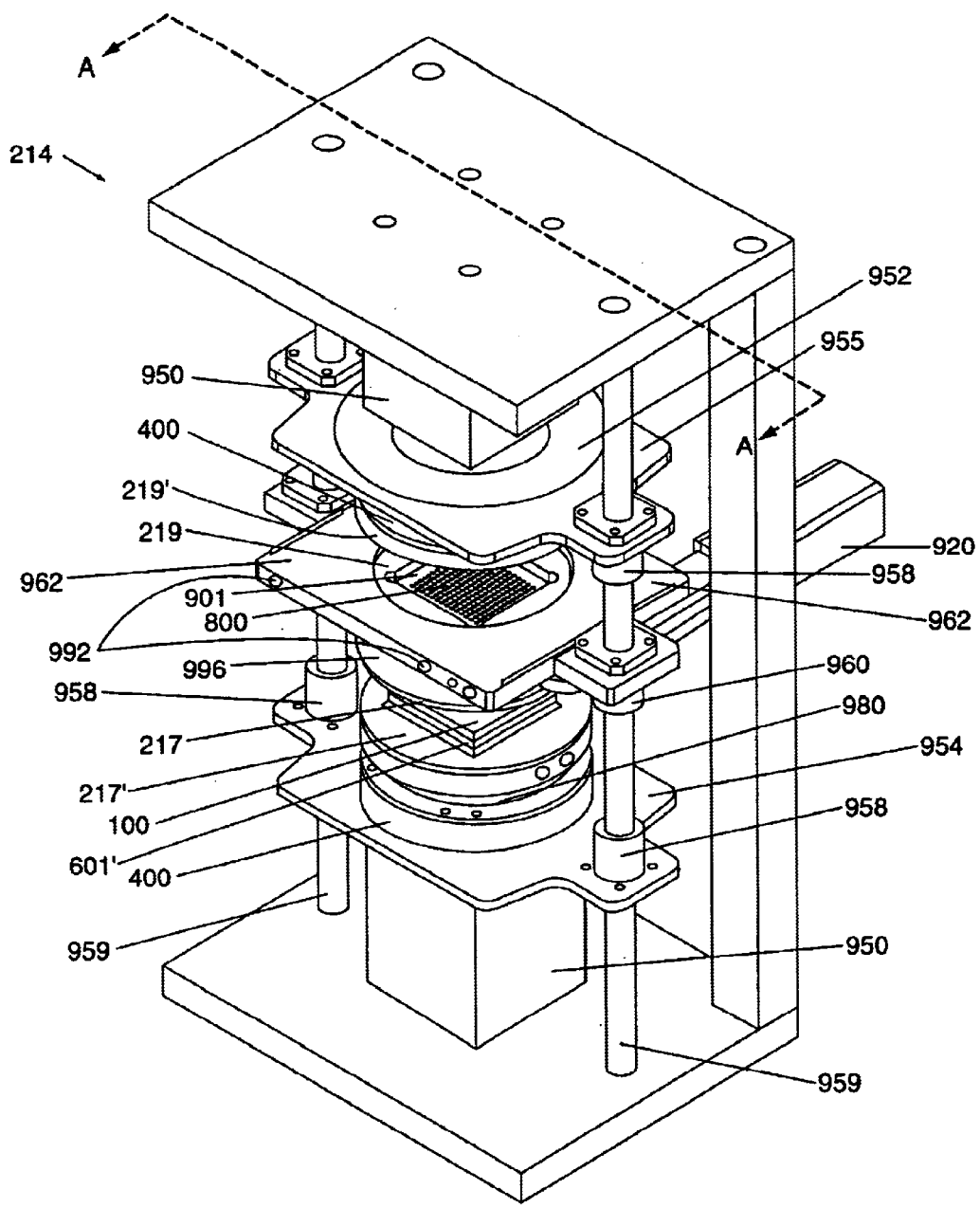
Figure 18D:
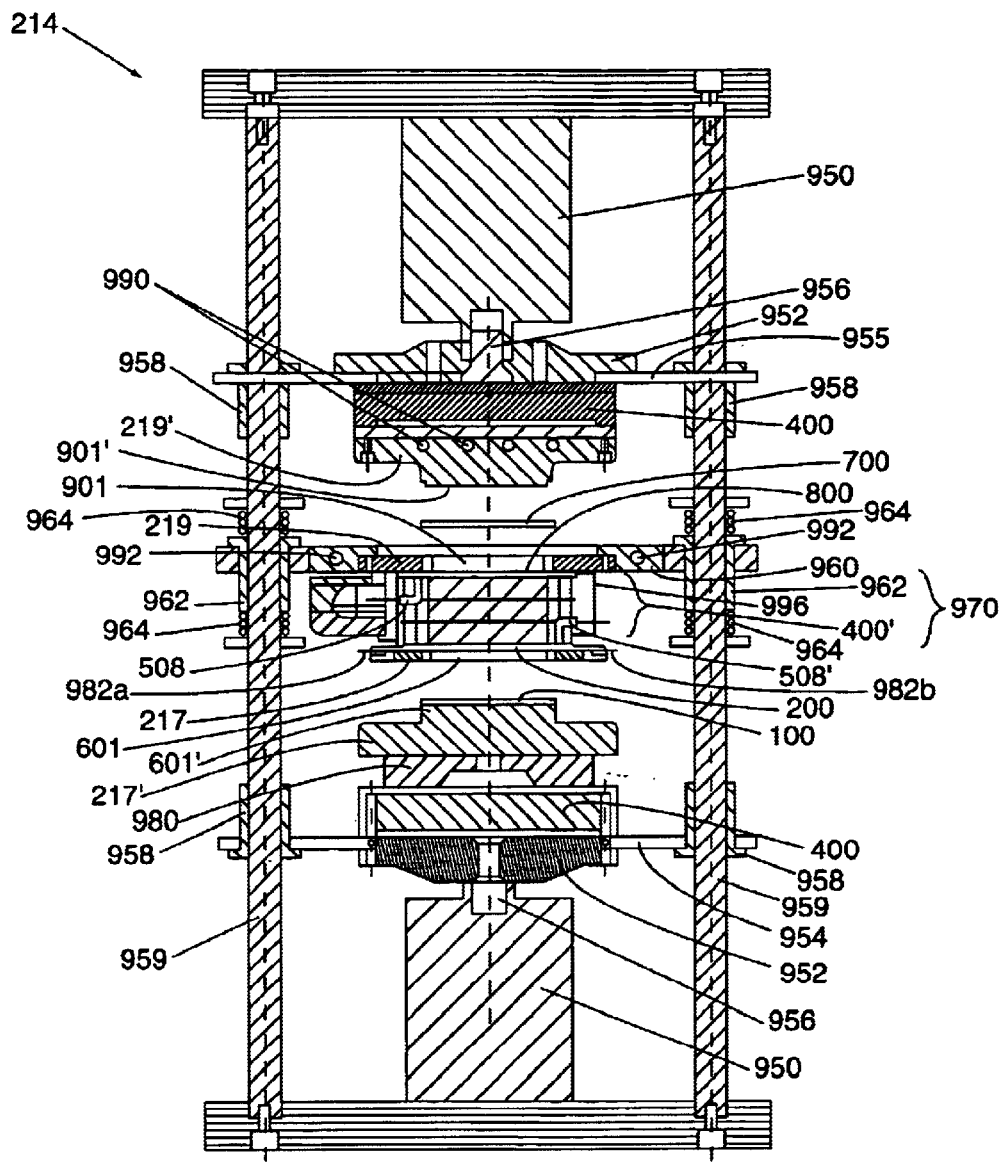
Figure 18E:
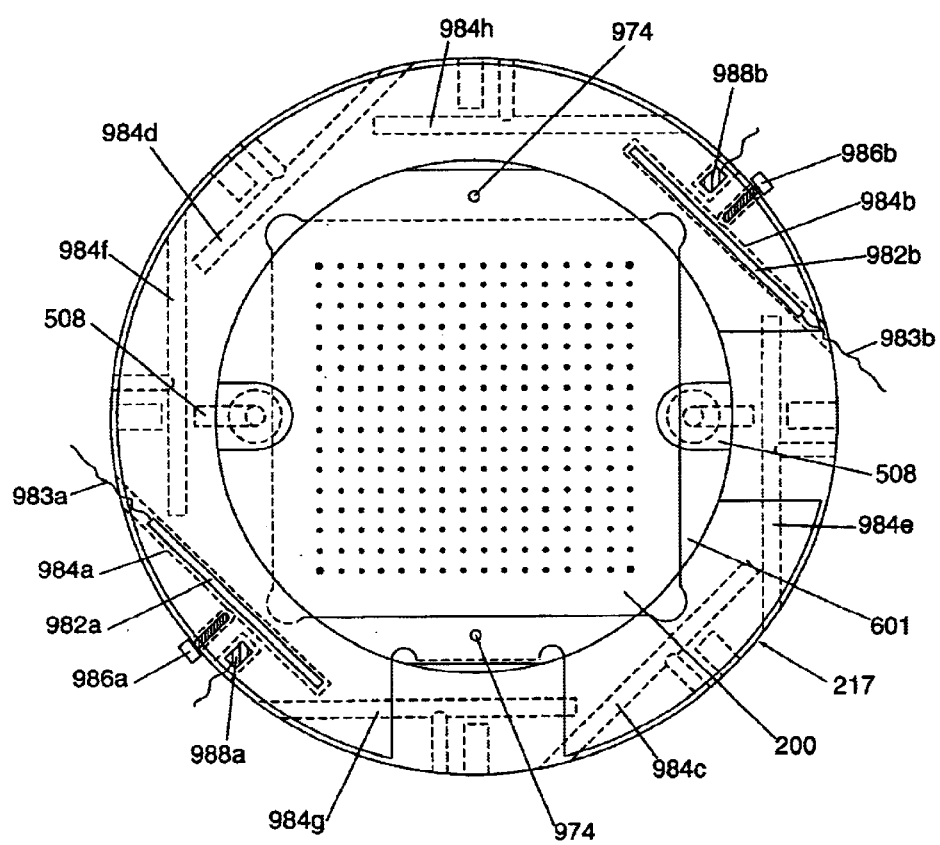
Figure 18F:
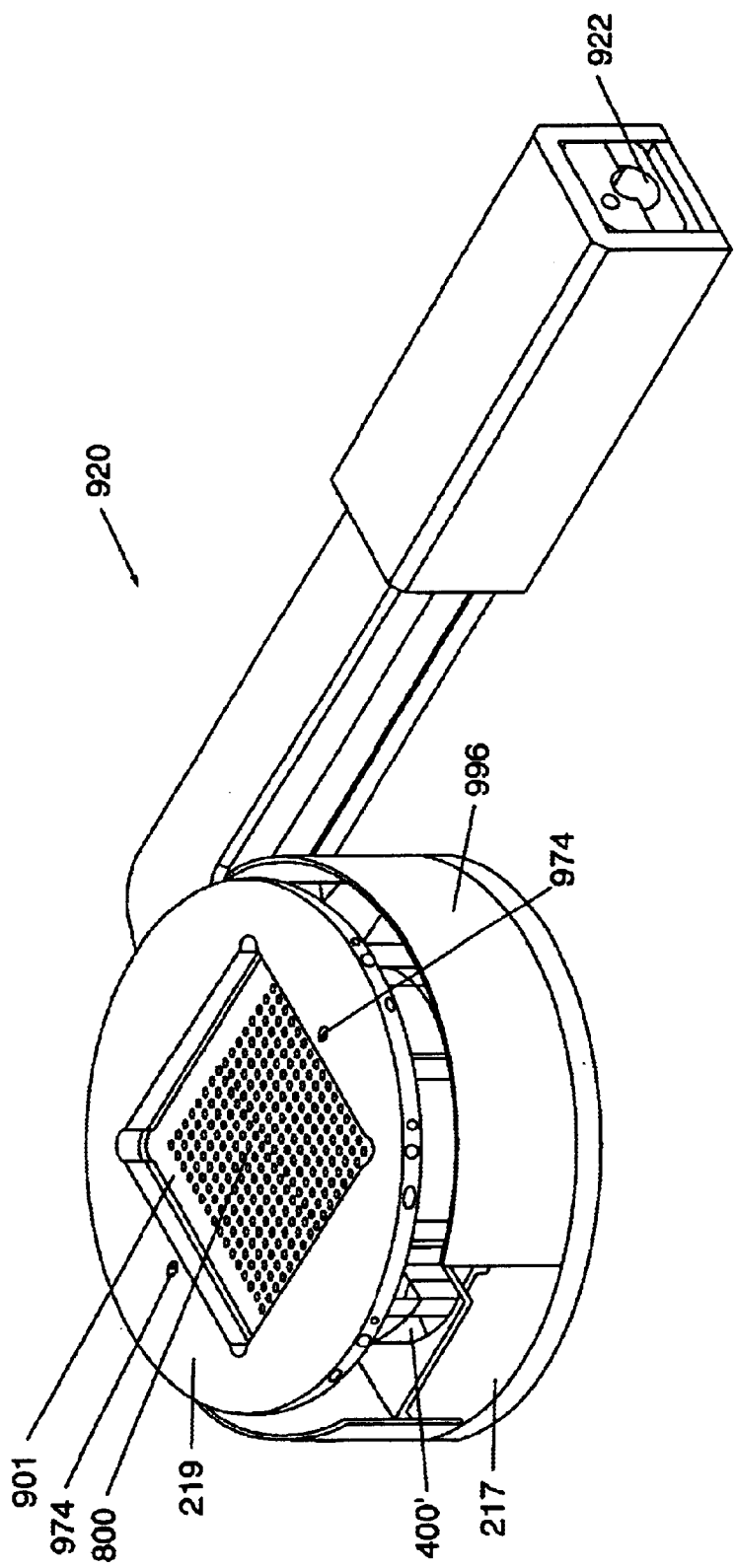
Figure 18G:
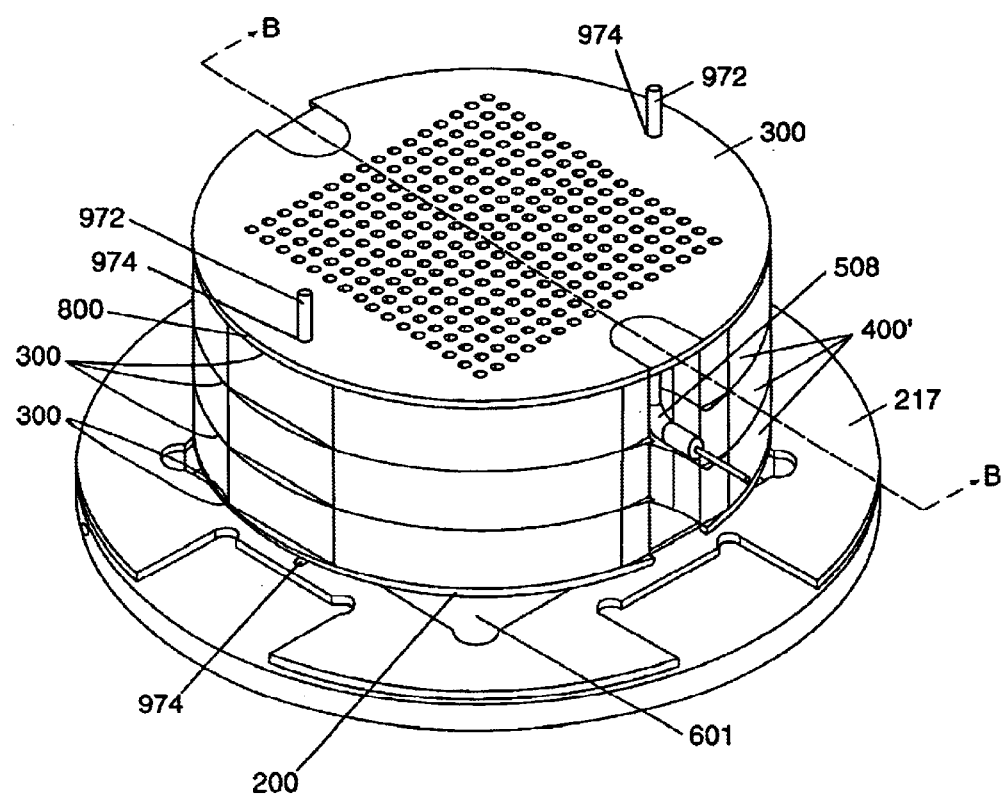
Figure 18H:
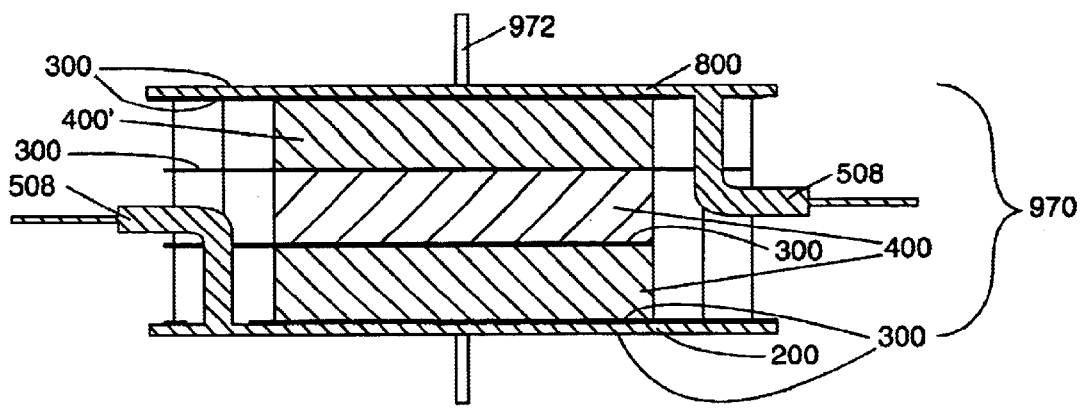
Figure 18I:
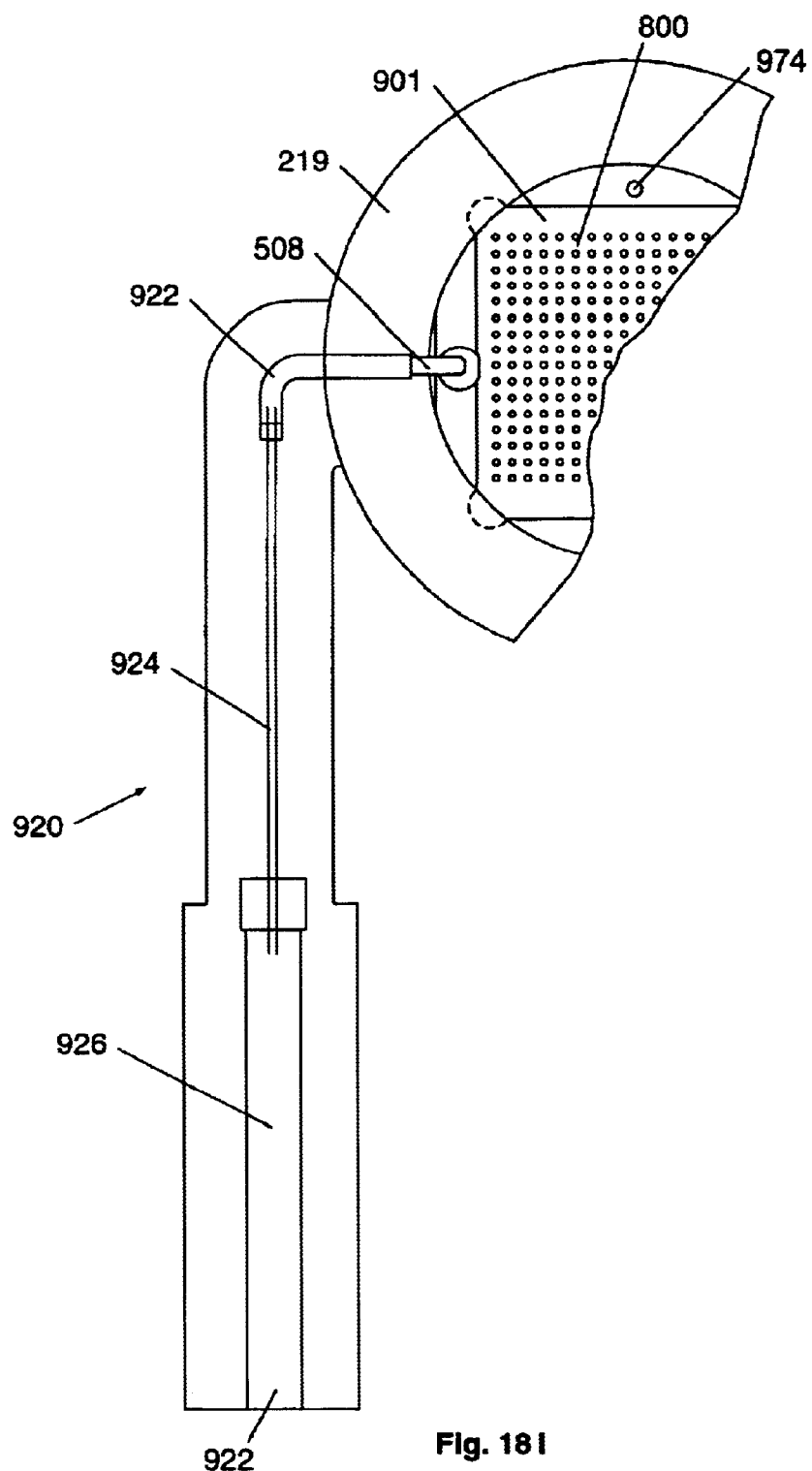
Figure 18J:
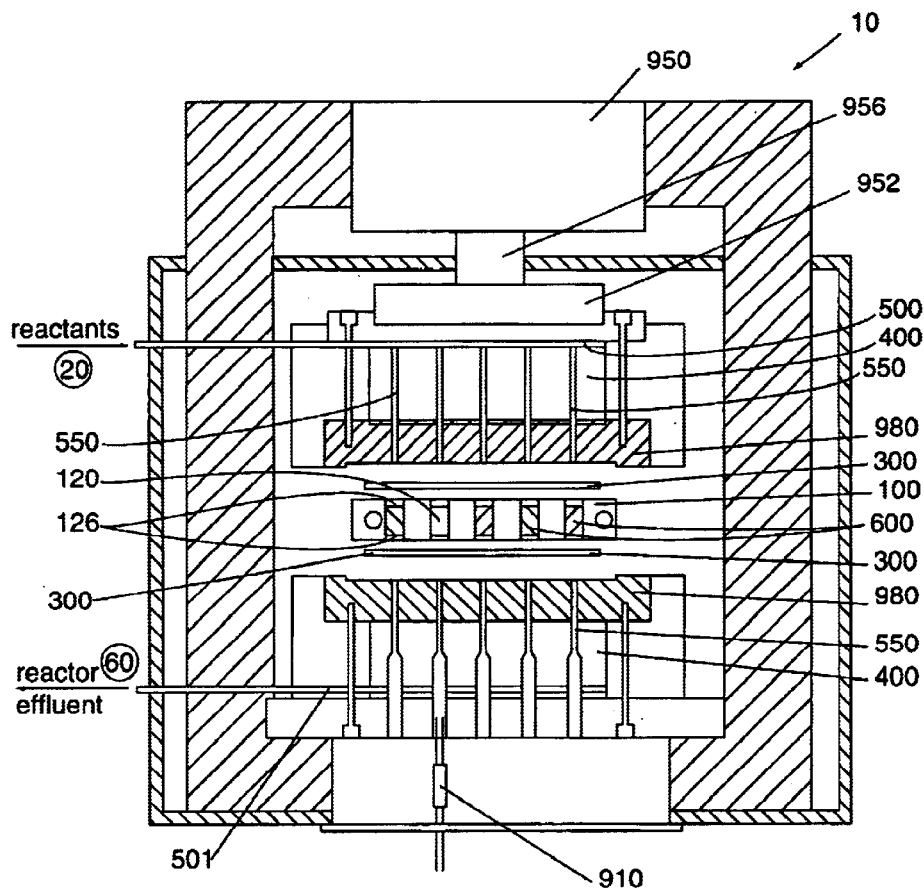

An alternative embodiment, shown in FIG. 18J, is directed toward a "flow-through" reaction system (e.g., analogous to a plug-flow reactor). Briefly, the microprocessing system 10 comprises a plurality of microreactors 600 formed in one or more laminae 100. The material-containing laminate 100 comprises a candidate material 920 such as beads or particulates contained within the microreactors by a porous barrier 126 (e.g., frits, porous plug, etc., as described above). As shown, the plurality of microreactors 600 are sealed and heated by adjacent temperature control blocks—shown as adjacent heaters 980—with releasable seals 300 (e.g., gaskets) situated between the heaters 980 and the microreactor laminae 100. Reactants 20 are provided to the microreactors 600 through an inlet distribution manifold 500 in fluid communication with the micoreactors 600 via connecting channels 550. The distribution manifold 500 is thermally isolated from the microreactors 600 by temperature control block 400. After contacting the candidate materials (e.g., catalysts) 920 under-reaction conditions, reactor effluent 60 is passed through connection channels 550 to a discharge manifold 501, and further to an external distribution (waste) system. The discharge manifold 501 is likewise thermally insulated from the microreactors 600 by another temperature control block 400. Evaluation of the candidate materials can be determined by analysis of reaction products, for example, by sampling of the reactor effluent stream using one or more sampling probes 910 (e.g. ,sampling needles) that are in selective fluid communication with one or more of the microreactors 600, and in further fluid communication with a detection system (e.g., gas chromatograph, mass spectrometer, FTIR, etc.). A septum or other suitable accessible barrier 911 may be employed in connection with the sampling system.

FIG. 18B shows a perspective view of a partially-assembled housing 214 adaptable for assembly and operation of a modular chemical processing microsystem 10 as shown in FIG. 18A and discussed in connection therewith. As shown in FIG. 18B, the partially-assembled housing comprises a first and second microreactor support block 217, 217', respectively, and a first and second microseparator support block 219, 219', respectively. The first microreactor support block 217 has a microreactor staging area 601 adapted to receive the candidate-material-containing laminate (100 of FIG. 18A) or alternatively, a plurality of laminae (100, 200, 300 of FIG. 18A) that comprise the plurality of candidate-material-loaded microreactors (600 of FIG. 18A). Likewise, the first microseparator support block 219 has a microseparator staging area 901 adapted to receive the adsorbent-containing laminate (700 of FIG. 18A) or, alternatively, a plurality of laminae (700, 300, 800 of FIG. 18A) that comprise the plurality of adsorbent-loaded microseparators (600 of FIG. 18A). Temperature control blocks (400 of FIG. 18A) can be provided to the housing 214 with the plurality of microreactor laminae and/or the plurality of microseparator laminae, or can be made integral with the second microreactor support block 217' and/or the first microseparator support block 219. A central support block 218 can be situated between the first surface of the microreactor support block 217 and the second surface of the microseparator support block 219', and can comprise another temperature-control block (400' of FIG. 18A)—such as a machinable glass ceramic insulation material (e.g. MACOR) or quartz, that provides connecting channels (550 of FIG. 18A) between the microreactors (600 of FIG. 18A) and microseparators (900 of FIG. 18A). The plurality of laminae in which the microreactors 600 and microseparators 900 are formed can be held together by compressive fastener fittings 216 that can be joined by bolted connection through apertures aligned as indicated by dashed lines. Other compressive fasteners—for example, axially-aligned springs, spring clamps or hydraulics could likewise be employed.

FIGS. 18C and 18D show a perspective view and corresponding sectional view (taken at A—A), respectively, of another preferred, partially-assembled housing 214 adaptable for assembly and operation of a modular chemical processing microsystem 10 as shown in FIG. 18A and discussed in connection therewith. As shown in FIGS. 18C and 18D, the partially-assembled housing comprises first and second microreactor support blocks 217, 217', respectively. The first microreactor support block 217 has a microreactor staging area 601 adapted to receive a candidate material containing laminate (candidate material array) 100

(with the candidate materials facing upward for the orientation shown in FIGS. 18C and 18D). The microreactor staging area 601 is preferably a void space in the first microreactor support block 217 into which, as discussed below, the candidate material array 100 will be inserted upon assembly of the system. As such, upon assembly, the first microreactor support block 217 provides lateral (radial) support to the candidate material array 100. In addition to its support function, the first microreactor support block 217 can also have other functional features, including a temperature control function and a subassembly-clamping function, each of which is discussed below in connection with FIGS. 18E and 18G, respectively. The second microreactor support block 217' likewise has a microreactor staging area 601' adapted to receive the candidate material containing laminate (candidate material array) 100. The microreactor staging area 601' is preferably a raised platform on or integral with the second microreactor support block 217' onto which, as shown and as further discussed below, the candidate material array 100 can be situated upon assembly of the system. As such, upon assembly, the second microreactor support block 217' provides normal (vertical) support to the candidate material array 100. In addition to its support function, the second microreactor support block 217' can also have other functional features, including a temperature control function as discussed below. Referring further to FIGS. 18C and 18D, the partially-assembled housing also comprises first and second microseparator support blocks 219, 219', respectively. The first microseparator support block 219 has a microseparator staging area 901 adapted to receive a the adsorbent-containing laminate (adsorbent array) 700 (with the adsorbent materials facing downward for the orientation shown in FIGS. 18C and 18D). The microseparator staging area 901 is preferably a void space in the first microseparator support block 219 into which, as discussed below, the adsorbent array 700 will be inserted upon assembly of the system. Hence, upon assembly, the first microseparator support block 219 provides lateral (radial) support to the adsorbent array 700. In addition to its support function, however, the first microseparator support block 219 can also have other functional features, including a temperature control function, discussed below, and a subassembly-clamping function, discussed below in connection with FIGS. 18G. The second microseparator support block 219' likewise has a microseparator staging area 901' adapted to engage the adsorbent-containing laminate (adsorbent array) 700. The microseparator staging area 901' is preferably a raised platform on or integral with the second microseparator support block 219' against which, as shown and as further discussed below, the adsorbent array 700 can be situated upon assembly of the system. The second microseparator support block 219', therefore provides normal (vertical) support to the adsorbent array 700 once the system is assembled. In addition to its support function, the second microseparator support block 219' can also have other functional features, including a temperature control function as discussed below.

Upon engagement of the first and second microreactor support blocks 217, 217', the candidate material-containing laminate (candidate material array) 100 is brought into contact with the reactor block 200 (See also FIG. 18A). The reactor block 200 includes a reactant supply manifold integral therewith (shown as 500 and described in connection with FIGS. 7B and 7I) having a single common inlet port (510 of FIG. 7I) near the edge of the manifold (500 of FIG. 7I), and having an elbow-shaped vertical conduit 508 extending normal to the reactor block 200 for interfacing with an external fluid distribution (reactant supply) system (480 of FIG. 1C). A releasable seal (e.g., graphite gasket) (300 of FIG. 18A) is preferably situated between the reactor block 200 and the candidate material array 100. Likewise, upon engagement of the first and second microseparator support blocks 219, 219', the adsorbent-containing laminate (adsorbent array) 700 is brought into contact with the separator block 800 (See also FIG. 18A). The separator block 800 includes an effluent discharge manifold integral therewith (shown as 501 and described in connection with FIG. 14) having a single common outlet port near the edge of the manifold, and having an elbow-shaped vertical conduit 508 extending normal to the separator block 800 for interfacing with an external fluid distribution (effluent discharge) system. A releasable seal (e.g., graphite gasket) (300 of FIG. 18A) is preferably situated between the separator block 800 and the adsorbent array 700. A temperature control block 400', comprising one or more insulator blocks, is situated between the reactor block 200 and the separator block 800. The temperature control block 400' also comprises a number of connecting channels (550 of FIG. 18A) providing fluid communication between the outlet port (260 of FIG. 18A) of the reactor block 200 and the inlet port (850 of FIG. 18A) of the separator block 800.

Engagement and disengagement of first and second microreactor support blocks 217, 217', and independently, the first and second microseparator support blocks 219, 219' is preferably supplied using one or more hydraulic mechanisms. Such engagement and disengagement can preferably be effected independently for the microreactor support blocks 217, 217' versus the microreactor support blocks 219, 219', such that candidate-material arrays 100 and adsorbent arrays 700 can be loaded and/or unloaded from the microsystem independently of each other. In a preferred embodiment shown in FIGS. 18C and 18D, hydraulic chambers 950 (e.g., Mead Fluid Dynamics) provide a vertically-oriented hydraulic force (e.g., ~40 psi) and are coupled by shafts 956 to flanges 952, to support plates 954, 955, and/or directly to the second microreactor support block 217' or the second microseparator support block 219'. The periphery of support plates 954, 955, respectively, are further supported by support brackets 958 that are slidably coupled to guide posts 959 such that upon hydraulically-actuated motion of shafts 956, the second microreactor support block 217' or the second microseparator support block 219' will move vertically. An additional, central support plate 960 can support the fluid distribution subassembly 970 that comprises the first microreactor support block 217, reactor block 200, temperature control block 400', separator block 800, and first microseparator support block 219, together with required releasable seals (300 of FIG. 18A). The central support plate 960 can be further supported along its periphery by central support brackets 962. The central support brackets 962 can be slidably coupled to guide posts 959, or alternatively, permanently or adjustably secured to guide posts 959 (e.g., with a set screw (not shown)). In a preferred design, the central support brackets 962 are slidably coupled to guide posts 959 with a limited range of motion defined by guide springs 964 (shown only in FIG. 18D). Significantly, guide springs 964 allow for either end of the microprocessing system 10—that is, either the microreactor end (lower portion as shown in FIG. 18C and 18D) or the microseparator end (upper portion as shown in FIGS. 18C and 18D)—to be engaged and disengaged independently from each other, thereby providing for great flexibility with respect to loading and/or unloading of candidate-material arrays 100 and adsrobent arrays 700. In addition to a support function, the central support plate 962, as well as the other support plates 954, 955, can have other functionalities such as temperature control functionality, as discussed below.

Temperature control of the microreactors and microseparators are effected using active (e.g., heaters) and passive (e.g., insulation) temperature control elements, together with temperature control systems. As noted, various aspects of temperature control elements are integrated into some of the aforementioned components. Referring to FIGS. 18C and 18D, the microreactors (600 FIG. 18A) and candidate material array 100 can be heated to a reaction temperature of interest by a heater 980 in thermal communication with the candidate-material array 100. The heater 980 can be a resistive heater, and is preferably a "pancake-type" resistive heater (e.g., ~1200 W). As shown, heat energy from the heater 980 is transferred by conduction through the second microreactor support block 217' to the candidate-material array 100. In such an embodiment, the second microreactor support block 217' is preferably a material having a high thermal conductivity (e.g., copper). Temperature control block (insulator block) 400 is situated under the heater 980 to minimize heat loss in a direction away from the microreactors. The resistive heater 980 can also be zoned to provide a temperature gradient across the various microreactors. Additional, fine temperature control can be provided to the microreactors by smaller, controllably resistive heaters 982a, 982b, placed, for example, in the periphery of the first microreactor support block 217. With reference to FIG. 18E, in one embodiment, one or more active temperature control elements such as resistive heaters 982a, 982b (~25 W) can be integral with the first microreactor support block 217, and as shown, situated in one or more heater cavities 984a, 984b, 984c, 984d, 984e, 984f formed therein. Each of such resistive heaters 982a, 982b can be held in place with set screws 986a, 986b, respectively and can be selectively controlled with a temperature control system connected to the resistive heaters 982a, 982b via control wires 983a, 983b, respectively, to provide fine-temperature control for the microreactors. The temperature control system can also include thermocouples 988a, 988b. Although resistive heaters 980, 982a, 982b, etc. are described in connection with this embodiment, other types of appropriate heaters (e.g., thermoelectric heaters, fluid heat-exchangers) can also be employed. With further reference to FIGS. 18C and 18D, the microseparators (900 of FIG. 18A) and adsorbent-material array 700 can be cooled to a temperature appropriate for selective adsorption of the one or more analytes (e.g., reaction products or unreacted reactants) of interest by a cooler in thermal communication with the adsorbent array 700. The cooler can be a fluid heat-exchanger in fluid communication with a cold-temperature heat sink. As shown, heat energy from the adsorbent array 700 is transferred by conduction through the second microseparator support block 219' to cooling channels 990 formed therein. A cooling fluid is circulated through the cooling channels 990 to an external heat sink. In such an embodiment, the second microseparator support block 219' is preferably a machinable material having a high thermal conductivity (e.g., aluminum ). Temperature control block (insulator block) 400 is situated over the cooler of the second microseparator support block 219' to minimize cooling of components situated in a direction away from the microseparators. The cooling channels can be "zoned"—for example with separate channels to separate heat sinks, as desired, to achieve a temperature gradient across the microseparators. Additional, fine temperature control can be provided in the first microseparator support block 219 in a manner similar to that described above in connection with the first miroreactor support block 217, except that thermoelectric coolers could be employed rather than resistive heaters 982a, 982b. The cooler can be integrated with a temperature control system that can also include thermocouples, for example, integral with the first separator support block 219. As shown, further temperature control of the microseparators is provided by an additional fluid heat-exchanger type cooling system that includes cooling channels 992 formed in the central support plate 960 through which a cooling fluid can flow. Heat energy from the microseparators can be transferred, by conduction, through the adsorbent array 700, the first microseparator support block 219, and the central support plate 960 to the cooling fluid, and ultimately to an external heat sink. Although fluid heat-exchanger type coolers are described in connection with this embodiment, other types of appropriate coolers (e.g., thermoelectric coolers, refrigerants) can also be employed.

Temperature control of the fluid distribution subassembly 970 is preferably provided by a temperature control block 400' (such as a passive insulator block 400'). With reference to FIGS. 18G and 18H, the temperature control block can be fabricated from a plurality of thinner (e.g., 0.5 inch or smaller) individual temperature control blocks 400', interfaced with releasable seals 300, to facilitate fabrication of the connection channels (550 of FIG. 18A). An insulating shield 996 encircling the temperature control block 400' can provide additional passive temperature control.

With reference to FIGS. 18F through 18H, the fluid distribution subassembly 970 (comprising the first microreactor support block 217, reactor block 200, one or more temperature control blocks 400', separator block 800, and first microseparator support block 219, together with releasable seals 300) can be preassembled prior to use in connection with the microsystem of FIGS. 18C and 18D. Allignment of the components of the fluid distribution subassembly 970 is preferably provided by allignment pins 972 inserted through precision-machined allignment apertures 974. Threaded fasteners (not shown) extending between and connecting the first microreactor support block 217 and the first microseparator support block 219 can be used to secure the subassembly, with the support blocks 217, 219 acting as clamping plates and providing a support function.

The fluid distribution subassembly 970 can be interfaced with one or more external fluid distribution subassemblies 920, as shown in FIG. 18F. Reactants and reactor effluent (or separated reactor effluent streams following adsorption) can be supplied to the microreactors or discharged from the microseparators, respectively,. through one or more such external fluid distribution subassemblies 920 (shown only for the effluent/discharge side). Briefly, with further reference to FIGS. 18G and 18H, a reactant can pass through an external fluid distribution subassembly (not shown for reactant/inlet side) into a reactant supply-side elbow-shaped vertical conduit 508 extending normal to the reactor block 200, through the reactant supply manifold integral with the reactor block 200 and into the microreactors. After reaction therein, the reactor effluent passes through the connecting channels (550 of FIG. 18A) of the temperature control block 400' and into the microseparators where one or more components thereof can be separated. The separated effluent stream then passes through the discharge mannifold integral with the separator block 800 and is discharged from the microsystem through the discharge-side elbow-shaped vertical conduit 508 extending normal to the separator block 800. Discharge-side conduit 508 is in fluid communication with the external fluid distribution subassembly 920. With reference to FIG. 181, the separated reactor effluent stream passes from the discharge-side conduit 508 (e.g., glass) through an elbow 922 (e.g., glass), through a flexible microcapillary 924 (e.g., polyimide-coated quartz capillary), through a rigid, larger diameter transfer conduit 926 and finally through the outlet port 922 of subassembly 920 to the external fluid distribution system (e.g., waste). Fittings, adhesives, bonding, etc. known in the art can be used to effect appropriate connections of the various distribution components 508, 922, 924, 926.

After one or more of the components of the reactor effluent stream have been separated therefrom (e.g., by adsorption onto the adsorbing material), the separated component may be detected (e.g., as to its presence or absence) and/or quantitatively determined using a variety of techniques known in the art. As noted, such determination can be effected in situ in the chemical processing microsystem. Alternatively and preferably, however, such determination is effected at a subsequent time and at a remote location.

Figure 19A:
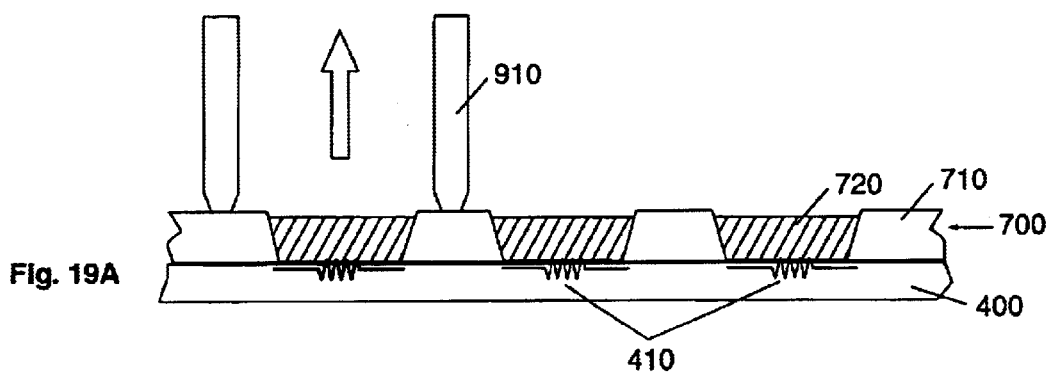
FIG. 19A through FIG. 19C are partial cross-sectional views of adsorbent-containing arrays with various configurations of detection probes and heaters.
Figure 19B:
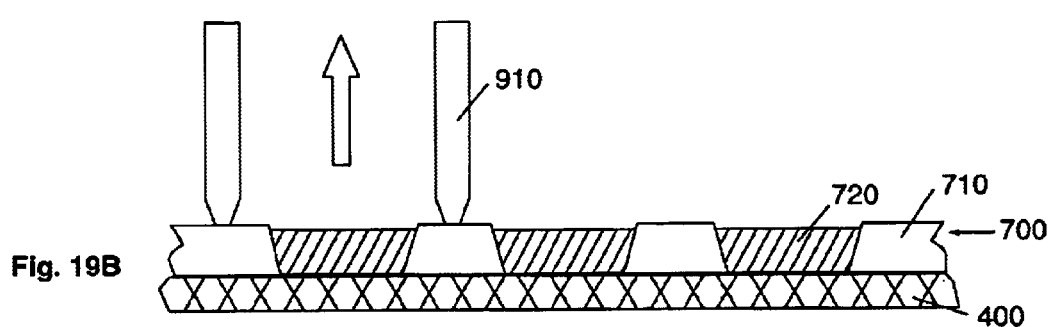
Figure 19C:
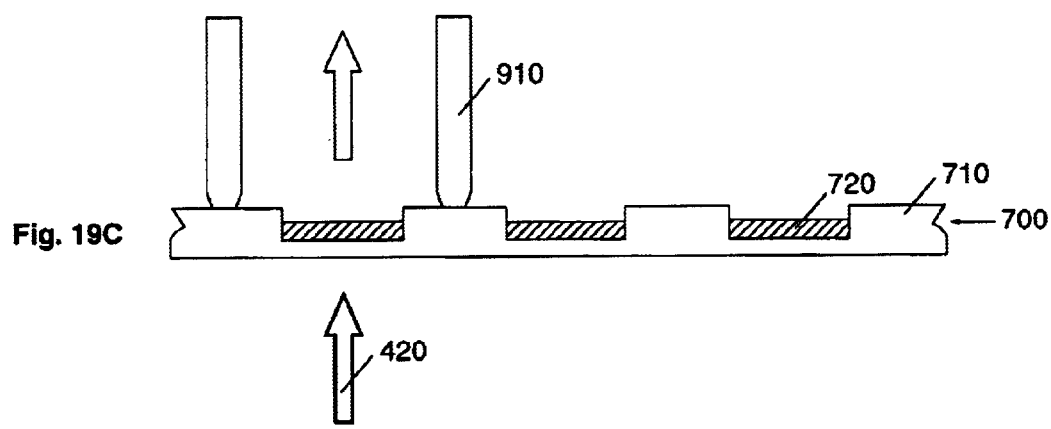

Quantitative determination of reactor effluent components can be performed, for example, by desorbing such components from the adsorbent material (e.g., by heating), and then detecting the desorbed component by gas chromatography, mass spectroscopy, infrared spectroscopy, optical spectroscopy (e.g., with indicator imaging) or other suitable approach. Briefly, for example, in the thermal desorption approach, samples can be desorbed into a gas chromatograph or into a mass spectrometer and analyzed as known in the art. Preferred gas chromatography approaches include rapid GC protocols such as those disclosed in Cooke, *Decreasing Gas Chromatography Analysis Times using a Multicapillary Column*, Abs. 403P, Book of Abstracts, PittCon' '96 (1996). Infrared spectroscopy can be applied by desorbing the adsorbates into a standard gas cell in an FTIR spectrometer. With reference to FIGS. 19A through 19C, for example, a detection probe 910 can be positioned over an adsorbent-containing region of an adsorbent array 700, and the reactor effluent component can be desorbed therefrom by heating. The heating can be controlled individually for each region (FIG. 19A, FIG. 19C) using, for example, spatially addressable resistive heating elements 410 within a temperature-control block 400 (FIG. 19A) or spatially addressable laser source 420 (FIG. 19C). The heating can alternatively be applied collectively and simultaneously to each of the adsorbent-containing regions to desorb reactor effluent components from each region simultaneously, but using multiple detector probes 910 in parallel.

In another detection approach involving indicator imaging (e.g., colorimetry)/spectroscopy the array of adsorbed materials can be exposed to detection agents (e.g., indicating agents such as fluorescent tags, dyes, colorants, radionuclides, biological markers or tags, etc.) that are selective for an analyte (e.g., one or more particular reactor effluent components of interest). Typically, the detection agent reacts and/or interacts (e.g., through hydrogen bonding) with one or more of the adsorbed species to form a detectable species. The array is then imaged to detect the detectable species using, for example, suitable spectroscopic techniques to determine fluorescent intensity or color wavelength and correlating the same with known standards to determine the presence, absence or quantity (relative or absolute) of the analyte component of interest. A preferred embodiment includes, with reference to FIG. 1C, a station for applying a detection agent to the adsorbed species, and a detector. The station can be a spray station for spraying dye or colorant onto the adsorbed component—or alternatively, for applying a detection agent to the adsorbent material prior to the reaction. The spray station can have an automated XYZ translation stage for providing relative motion between a stationary nozzle (e.g., a passive ultrasonic nozzle) and the array of adsorbent material. Detection agent can be provided to the spray nozzle from one or more reservoirs through feed lines by syringe-pump motive force. Near simultaneous detection can be determined, for example, by exposing the detectable species to UV light, and determining intensity with parrallel detection devices, such as a CCD camera (e.g., Andor, Ireland) under software control of the manufacturer. The CCD camera can detect UV fluorescence (e.g., for fluorescent dyes) and/or transmission absorbance (for color dyes). The detected signal can be correlated to signals from known standards to determine the presence, absence and/or absolute or relative quantity of analyte.

Figure 16C:
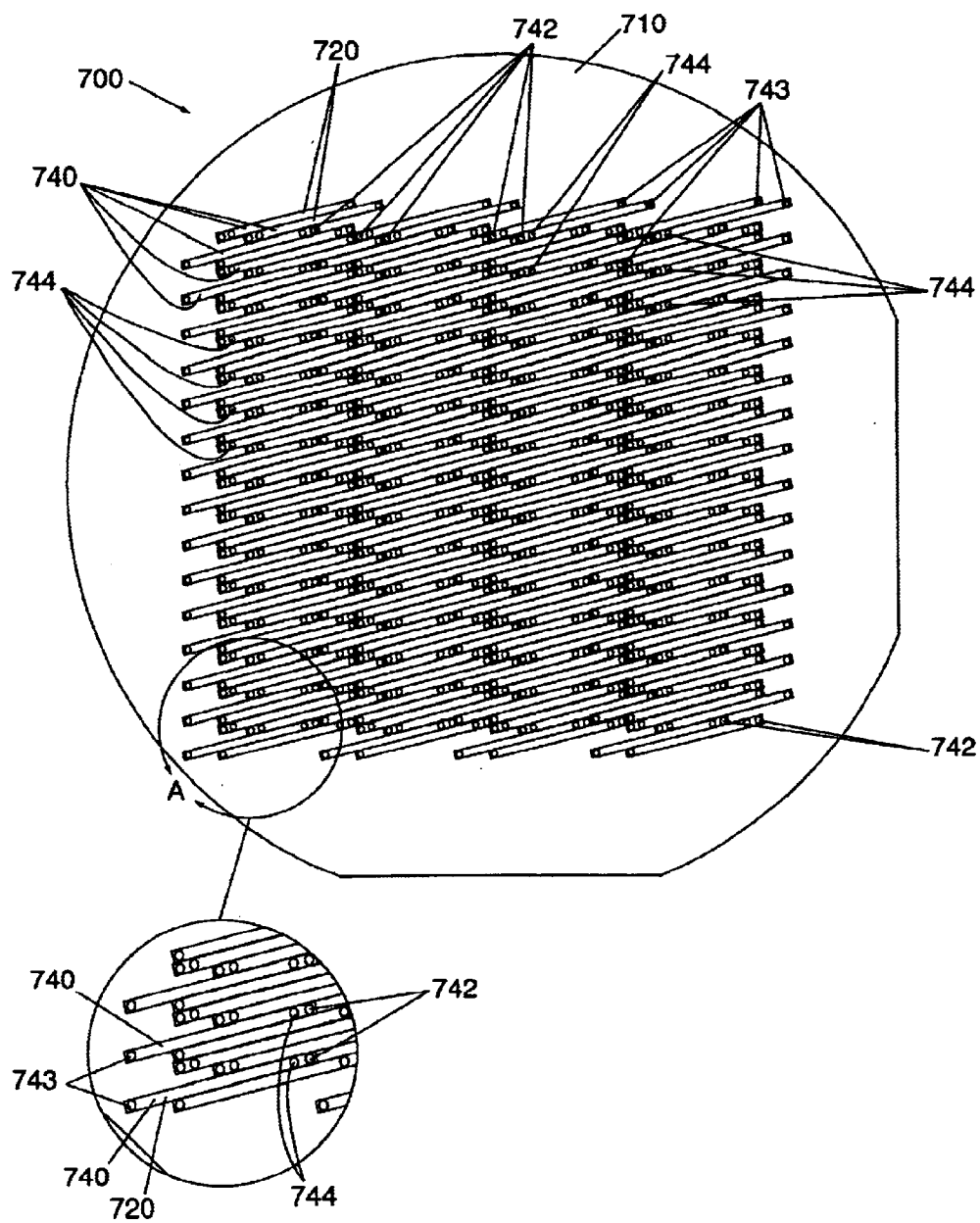
Figure 16D:
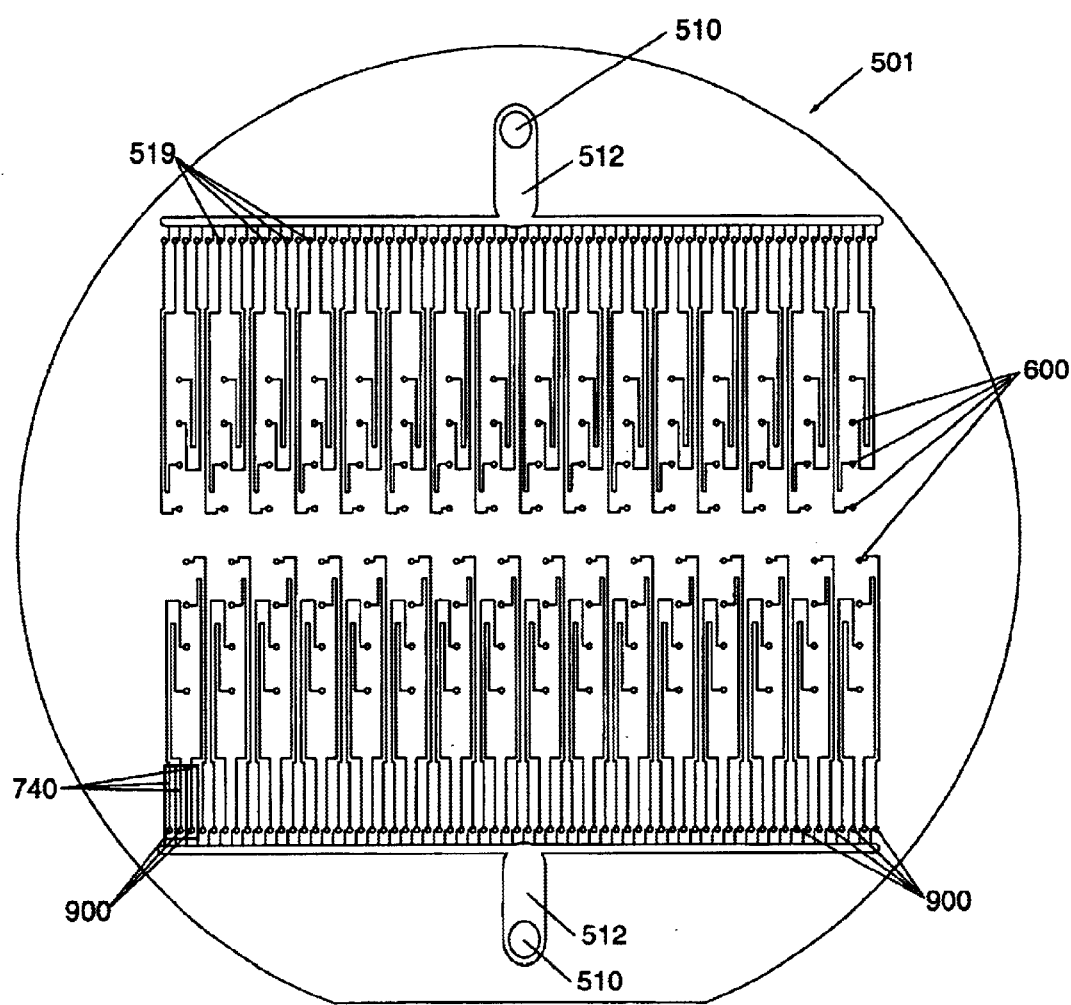
Figure 16E:
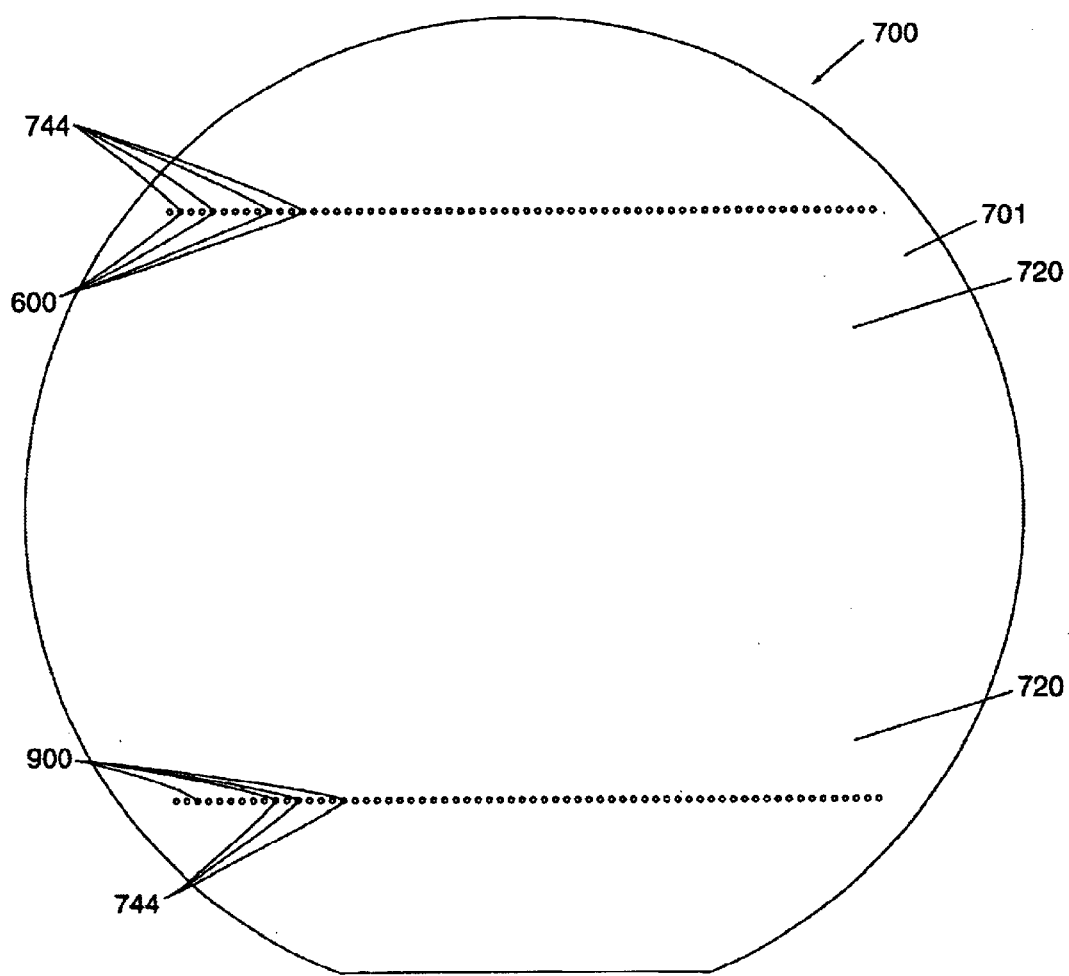

FIGS. 16C and 16D show arrays of adsorbent materials that can be employed in detection schemes involving thin-layer chromatography (TLC) techniques to determine the presence, absence or relative or absolute quantity of a particular reaction product of interest. FIG. 16C, including corresponding detail (taken at A), shows an array comprising a plurality of substantially parallel TLC channels, each of the plurality of TLC channels 740 having one or more mobile-phase inlet ports 742 and one or more mobile-phase outlet ports 743 in fluid communication with each other (via the TLC channel 740). The TLC channels 740, and mobile-phase inlet and outlet ports 742, 743 can be formed in a substrate 710 using microfluidic manufacturing techniques generally known in the art, such as those discussed above in connection with fabrication of the microreactors, microseparators and fluid distribution systems. The TLC channels 740 contain an adsorbent material 720 that is substantially selective for one or more analytes (e.g., reaction products or unreacted reactant) of interest. The TLC channels 740 are arranged such that a portion of the adsorbent-material-containing TLC channel 740, referred to herein as the adsorption spot 744, can be in fluid communication with a microseparator 900 of the invention (as described above). The adsorption spot 744 can, in some embodiments, form a portion of a surface that defines the separation cavity (e.g., by having microseparator cavities arranged to correspond to the arrangement of adsorption spots 744 as shown in FIG. 16C). In preferred embodiments, the adsorption spot 744 is preferably located in a portion of the TLC channel 740 that is closer to the mobile-phase inlet port 742 of the TLC channel 740 than to the mobile-phase outlet port 743 thereof. In general, however, the length of TLC channel between the adsorption spot 744 and the mobile-phase outlet port 743 is preferably sufficient to obtain meaningful TLC data upon subsequent elution of the adsorbed analyte of interest. In operation, with reference to FIG. 16C and FIG. 18A, an analyte in the reactor effluent stream 40 can be selectively adsorbed and deposited onto the adsorbent material 720 at the adsorption spot 744 in the TLC channel 740, with the separated reactor effluent 60 passing through the discharge manifold (501 of FIG. 14) as described. Following the reaction, the TLC-array 700 can be removed from the microprocessing system 10 (as described), and then evaluated in a TLC detection system (not shown) comprising a mobile-phase source, a mobile-phase supply manifold (e.g., substantially as shown and described in connection with FIG. 7B or 7I), the TLC array 700, a mobile-phase discharge mannifold (e.g., substantially as shown and described in connection with FIG. 14), a mobile-phase sink, together with appropriate releasable seals (e.g., gaskets) between the manifolds and the TLC array 700. A TLC mobile phase (e.g., eluant or solvent) can flow in each of the plurality of mobile-phase inlet ports 742, through each of the plurality of TLC channels 740, and out each of the plurality of mobile-phase outlet ports 743. After optional treatment with appropriate detection agents (e.g., indicating agents) and detection thereof, the relative movement of the analyte of interest down the length of the TLC channel 740 can be correlated to known standards (included, for example, in the microreaction/microseparation system during the reaction of interest) for determination, and ultimately, for evaluation of the candidate materials (or processing conditions, etc.). In another embodiment, shown in FIG. 16D, the microreactor effluent is discharged from microreactors 600 through a discharge mannifold 501 (e.g., having flow resistance characteristics substantially as described in connection with FIG. 14), and is contacted with an array of adsorbent-material containing microseparators 900 arranged in one or more rows near the peripheral edge of the substrate. The microseparators can be on the same substrate as the microreactors 600, or alternatively, as shown in FIG. 16E, on a different substrate, but in fluid communication with the discharge flowpaths (e.g., through a row of apertures 519 and connecting channel 550 (not shown)). In either case, the microseparators can also be TLC channels 740 (with the adsorbent material situated therein) located along an external edge of the TLC array 700. An analyte can be selectively adsorbed onto the adsorbent material 720 in the microseparators 900. The TLC-array 700 can be subsequently removed from the microprocessing system 10 (as described), and then evaluated in a TLC detection system (not shown) comprising a solvent with which the analyte-containing edge of the adsorbent array 700 is contacted, and eluted therefrom (substantially as known in the art). After optional treatment with appropriate detection agents (e.g., indicating agents) and detection thereof, the relative movement of the analyte of interest can be correlated to known standards, as discussed above.

The detection (following the desorption approach, the imaging approach, or otherwise) can be carried out for each of the plurality of adsorbent-containing regions in rapid-serial fashion, in serial-parallel fashion (serial application for a subgroup of detectors) or in completely parallel fashion. Significantly, even if serial desorption and detection systems are applied herein, the results obtained represent the reaction components (e.g., reaction products) obtained simultaneously and concurrently from the plurality of microreactors. As such, the evaluation system of the invention offers a great degree of flexibility with respect to preservation and analysis of data.

While the preferred separation and analysis approach has been exemplified herein with respect to an adsorption process, an analogous approach can be taken based on other chemical separation techniques. For example, in place of the adsorbent material 720, a blank well 730 could be employed. The well 730 could be cryogenically cooled using temperature-control block 400 to facilitate condensation of gaseous reactor effluent components into the well 730. As another example, gas chromatographs and/or mass spectrometers can be used to "sniff" reactor effluent, in rapid-serial and/or in parallel, directly and without first adsobring the chemical species of interest. Note that while the methods and embodiments of the invention can be exemplified primarily herein for, and preferably for, chemical reactions having gaseous reaction products, an analogous approach can be applied for evaluating liquid-phase reactor effluent streams.

Removal of Candidate Materials from Microreactors

The plurality of different candidate materials being screened for their capability to enhance the chemical process of interest can be removed, preferably simultaneously, from each of the plurality of microreactors. Specifically, a first candidate material is unloaded from a first microreactor and, preferably simultaneously therewith, a second candidate material is unloaded from a second microreactor. If additional candidate materials were evaluated in additional microreactors, then each additional candidate material is preferably likewise simultaneously unloaded from their respective individual microreactors.

In preferred embodiments, in which the candidate materials were supplied to the plurality of microreactors as an array of candidate materials, the array can be removed from the chemical processing microsystem by releasing the array from the other microreactor components (e.g., fluid distribution system), and then withdrawing the released array. The array is preferably released without substantially affecting the structural integrity of the other microreactor components. With reference to FIG. 2, for example, the candidate material array 100 can be released by disengaging the first surface 201 of the reactor block 200 from the second surface 212 of the housing block 210. The array 100 can then be removed by breaking the contact between the array 100, the seal 300 and the heating block 400. An analogous approach can be taken for unloading the candidate material array 100 of FIGS. 8, 18A and 18B.

Significantly, once the array 200 is released and unloaded from the plurality of microreactors, a different candidate material-containing array 100 can then be loaded to the microreactors. It may be desirable, in conjunction therewith, to provide a new, releasable seal 300 between the adjacent surfaces of the array 100 and the reactor block 200.

Removal of Adsorbate-Containing Adsorbent from Microseparators

The adsorbate-containing adsorbent employed for separating one or more reactor effluent components can be removed, preferably simultaneously, from each of the plurality of microseparators. Specifically, a first adsorbate-containing adsorbent is removed from a first microseparator and, preferably simultaneously therewith, a second adsorbate-containing adsorbent is removed from a second microseparator. If additional reactor effluent components were adsorbed from the reactor effluent streams of additional microreactors, then each additional adsorbate-containing adsorbent is preferably likewise simultaneously removed from their respective individual microseparators.

In preferred embodiments, in which the adsorbent is supplied to the plurality of microseparators as an array, the array can be removed from the chemical processing microsystem by releasing the array from the other microseparator components (e.g., fluid distribution system), and then withdrawing the released array. The array is preferably released without substantially affecting the structural integrity of the other microseparator components. With reference to FIGS. 18A and 18B, for example, the adsorbent array 700 can be released by disengaging the second surface 702 of the adsorbent array 700 from the first surface 821 of the composite separator block 800.

Significantly, once the array 700 is released and removed from the plurality of microseparators, a different adsorbent array 700' can be supplied to the microseparators. It may be desirable, in conjunction therewith, to provide a new releasable seal 300 between the adjacent surfaces of the array 700 and the separator block 800.

Integrated Material Evaluation System

As noted, the chemical processing microsystem described in substantial detail herein can be, and is preferably, integrated into a material evaluation system for effectively and efficiently identifying new materials such as catalysts. Particular reference is made to FIG. 1B, FIG. 1C and FIGS. 18A and 18B, as well as the discussion provided in connection therewith.

Process Characterization and/or Optimization

Chemical conversion is inherently process-intensive. As such, advances in process knowledge, and improvements in process performance (e.g., selectivity, yield) can be of significant commercial value. The combinatorial chemistry approach, and particularly, the devices and systems disclosed herein, can be advantageously applied to process characterization and/or optimization research.

According to one approach for optimizing a chemical process, the particular process of interest is effected in a multi-parallel fashion while varying only a limited number (e.g., one, two or three) of process conditions during each experiment. More specifically, one or more reactants are simultaneously supplied to each of four or more microreactors, a first set of reaction conditions is controlled to be substantially identical in each of the four or more microreactors, a second set of reaction conditions is controlled to be varied between two or more of the microreactors, the first and second set of reaction conditions are controlled, collectively, to effect the chemical reaction of interest, a reactor effluent is discharged from each of the four or more microreactors, and the effect of varying the second set of reaction conditions is evaluated. To optimize a particular chemical reaction, for example, the same reaction can be effected simultaneously in two or more microreactors under reaction conditions that are substantially identical in each microreactor, except as to the controlled variation of, independently or collectively, temperature, pressure, residence time, relative amount of reactants, relative amounts of catalyst, etc. Particular research strategies for a given process can be devised by persons of skill in the art.

As such, the chemical processing microsystem of the present invention can be readily employed to conduct such parallel process research. Specifically, a plurality of microreactors can be configured to have substantially identical process conditions, except as to the controlled variation in certain selected variables. As noted above, for example, and with reference to FIG. 8 and/or FIG. 18A, the temperature in each of the plurality of microreactors 600 can be varied between groups of microreactors or between each of the microreactors 600 by providing a temperature gradient across the material-containing to array 100, or by providing spatially addressable independent heating elements to individually control the temperature of each microreactor (or each candidate material). The pressure can be varied for a group of microreactors or for each individual microreactor by using active pressure-control elements (e.g., individual valves for a group of microreactors or for each microreactor) or passive pressure-control elements (e.g., varying the conductance of the distribution channel serving a group of microreactors or serving each microreactor). Residence time can also be varied for a group of microreactors or for each of the microreactors, for example, by designing each of the plurality of microreactors 600 included in the chemical processing microsystem 10 to have a different volume. Alternatively, variable flow could be achieved to each microreactor. Catalyst amounts and/or surface areas can be readily varied by design, using fabrication methodologies known in the art. Moreover, catalyst structure can also be varied using various material-deposition approaches.

Small Quantity Production

Many chemicals can be synthesized only, or more efficiently, by processes which are inherently hazardous, and/or can be hazardous or unstable to ship and/or store. As to such chemicals, the localized, small volume production thereof can be advantageously effected in the microreactors and Microsystems of the present invention.

According to one approach for the production of small quantities of a particular chemical of interest, one or more equivalent reactions can be effected in each of a plurality of microreactors as described above, with or without the presence of a catalyst. The reaction products can be separated, as described, and/or collected. The conversion and yield can vary substantially depending on the chemical be produced and the mechanism employed. A mixture of products can also be established by varying the reaction in each of the microreactors and then combining the reaction effluents or the collected reaction products.

The following examples illustrate the principles and advantages of the invention.

EXAMPLES

Example 1

Manufacture of Microreactor/Microseparator

A chemical processing microsystem, substantially as shown and described in connection with FIGS. 18A and 18B, was manufactured as follows. The microsystem can be used, for example, to identify potential heterogeneous catalysts for the direct amination of benzene to aniline.

Reactor Block Array

A first silicon/glass laminae substructure comprising 256 reactor block wells, a fluid supply manifold/flow restrictor substantially as shown and described in connection with FIG. 7B, and a reactor effluent channel for fluid communication with an effluent manifold was formed. The laminae substructure was fabricated from one 4" diameter double polished p-type Si(001) wafer (International Wafer Service) and one Pyrex 7740 glass wafer (Coming) using standard microprocessing technology.

Fluid distribution components (supply manifold and reactor effluent channels) were formed in the silicon wafer. Briefly, the silicon wafer was coated with 5000 Å low-stress $Si_3N_4$ in a silane/ammonia CVD tube reactor. 1 μm Shipley 1813 photoresist was spun onto both sides of the nitride-coated wafer and soft-baked at 90° C. for 15 minutes. One side of this wafer was photolithographically exposed using a mask aligner (Electronic Visions) and subsequently developed using Shipley MF-319 photoresist developer to pattern the channel structure into the photoresist. Following development the wafer was hard-baked at 120° C. for 15 minutes. The silicon nitride was completely removed from the exposed areas in the photoresist using a $SF_6$ +$CF_3Br$ plasma in a capacitive plasma etcher (Drytek). All photoresist was then removed in a 120° C. 2:1 solution of $H_2SO_4$:$H_2O_2$. The remaining silicon nitride was used as an etch mask for etching the channels. A 22.5% KOH solution at 80° C. was used to etch the channels. The etch rate was measured to be ~0.8 μm/min and the etch was timed to control the channel depth. After the supply-manifold channels were etched, an array of two-hundred-fifty-six apertures (120 μm diameter) were created normal to the silicon wafer surface using a YAG laser (CCT Laser Processing) for use as the microreactor effluent channel. Finally, the silicon nitride was removed in a solution of phosphoric acid at 150° C.

An array of two-hundred-fifty-six apertures (1 mm diameter) were created in the Pyrex glass wafer using ultrasonic drilling for use as the reactor-volume-controlling portion of the reactor block wells.

The silicon wafer and glass wafer were then manually aligned with respect to each other in an anodic bonding chuck (Electronic Visions), such that the array of apertures on the glass wafer were concentric with the array of apertures on the silicon wafer. The silicon and glass wafers were then anodically bonded at 305° C. at 1000 Volts for 20 minutes which produced a total charge displacement of around 2 Coulombs for the wafer pair, thereby forming the laminae substructure having an array of reactor blocks.

Catalyst Array

A catalyst array was created by sol-gel protocols using a 3"×3" square glass or quartz substrate (Chemglass) having an array of two-hundred-fifty-six wells arranged to correspond to the arrangement of reactor blocks on the silicon/glass laminae substructure. The candidate materials were candidate catalysts to be screened for their capability to catalyze the direct amination of benzene to aniline. The specific methodology employed for forming the catalyst array is described in copending U.S. patent application Ser. No. 09/156,827, filed Jan. 18, ,1998 by Giaquinta et al.

Separator Block Array

A second silicon/glass laminae substructure comprising 256 separator block wells, a fluid discharge manifold such as shown and described in connection with FIG. 14, and a microseparator inlet channel for fluid communication to the microseparator was formed. The laminae substructure was fabricated from one 4" diameter double polished p-type Si(001) wafers (International Wafer Service) and one Pyrex 7740 glass wafer (Coming) substantially as described above for manufacture of the reactor block array, except that the photoresist patterns were altered such that the fluid-discharge manifold had a uniform width over each of the effluent paths (i.e., was not flow-restricting—substantially as described in connection with FIG. 14).

Adsorbent Array

An asorbent array substrate was created in a third silicon/glass laminae substructure formed from a 4" diameter silicon wafer and a 4" diameter Pyrex 7740 glass wafer having a thickness of about 0.5 mm. The glass wafer was ultrasonically drilled with an array of two-hundred-fifty-six apertures (1 mm diameter) arranged to correspond to the apertures formed in the separator blocks of the microseparators. The silicon and glass wafers were registered with respect to each other on the anodic bonding chuck and anodically bonded at 305° C. at 1000 Volts for 20 minutes to form an array of two-hundred-fifty-six cylindrical wells 1 mm in diameter and 0.5 mm deep.

An adsorbent suitable for detecting aniline was then deposited into each of the wells of the adsorbent array substrate to form the adsorbent array. The adsorbent was Adsorbosil-Plus-1 (Alltech), a silica gel with an inorganic binder (calcium sulfate). The as-purchased adsorbent was mixed with water to form a slurry. An indicating dye for aniline was incorporated into the slurry to assure uniform distribution of the indicator. The slurry was then trawled into the wells in the adsorbent-substrate laminae substructure using a razor blade. Extra slurry was removed from the wafer surface with the razor blade and the array was allowed to dry at room temperature for one hour, and then heated to 100° C. for one additional hour.

Temperature-Control Block

A 4" diameter machinable ceramic insulating block (MACOR) having a total thickness of about 2" was employed as a temperature control block between the microreactors and the microseparators. An array of two-hundred-fifty-six apertures (1 mm diameter) were formed in the insulating block to operate as connecting channels—to provide fluid communication between each of the microreactor effluent (discharge) channels and each of the microseparator inlet channels. In other embodiments, the insulating block was formed by combining several quartz blocks (0.5 inch). The connecting channels were formed therein by laser drilling (diameters ranging from about 0.15 mm to about 0.5 mm).

Releasable Seals

Releasable seals were prepared from quartz paper sheets (Whatman) by mechanically punching an array of two-hundred-fifty-six apertures therein with an array of pins. The aperatures were arranged to correspond to the array of microreactor blocks and the array of microseparator blocks.

Chemical Processing Microsystem

The chemical processing microsystem was then formed from the subcomponents in a housing substantially as shown and described in connection with FIG. 18B. Briefly, the reactor block array and the candidate material array were releasably integrated with each other to form an array of microreactors by aligning the array of candidate materials with the array of reactor blocks with a releasable seal situated therebetween. Similarly, the separator block array and the adsorbent array were releasably integrated with each other to form an array of microseparators by aligning the adsorbent array with the array of separator blocks with a releasable seal situated therebetween. The temperature-control block was then situated between the array of microreactors and the array of microseparators with the interconnecting channels of the temperature-control block aligned to provide fluid communication therebetween and with releasable seals situated between the temperature-control block and each of the microreactor array and the microseparator array. The compressive fasteners of the housing were then used to engage each the laminae to form the chemical processing microsystem.

Example 2

Operation of Parallel Microreactor/Microseparator

Catalyst Synthesis

Catalysts were formed using various methods known in the art and/or described herein (See, especially, the examples in above-referenced, co-pending patent application U.S. Ser. No. commonly-owned co-pending U.S. patent application Ser. No. 09/516/669, filed Mar. 1, 2000 by Lugmair et al Chemical compositions of the catalyst libraries were generated interactively using LIBRARY STUDIO™ (Symyx Technologies, Inc.) library design software, together with automated liquid handling equipment (Cavro Scientific Instruments, Inc.) under software control of IMPRESSIONIS™ (Symyx Technologies, Inc). Briefly, catalysts were formed in 4 mm diameter wells on a 3"×3" square glass or quartz wafer. For impregnation synthesis, slurried catalyst carriers were arrayed into the wells with a liquid handling robot. The slurries were dried and prefabricated support wafers were stored until needed for catalyst library synthesis. The catalyst impregnation was effected by incipient wetness technique. A synthesis robot generated an array of mixed metal-salt precursor solutions in a microtiterplate. From this microtiterplate small volumes of liquid were transferred from each well to a corresponding support. The volume of catalyst support and its pore size determined the volume transferred. After all desired supports have been impregnated, the wafer was dried at 120° C. for 1 hour and then the metal counter-ions were removed and metal oxides were formed by heating to 350° C. for 3 hours in air. The impregnation, drying, calcining process was repeated multiple times to increase the catalyst loading in the support. After synthesis was complete, the wafers were partially reduced, to form the desired catalyst. This processing was done in a 4" quartz tube furnace with wafers lying flat on a quartz slide.

Microreactor/Microseparator Operation

The reactant feed was a combination of gases and liquids. The gases were metered using Unit 1661 MFC's in a z-block configuration. The liquids were pumped with Gilson 361 HPLC pumps. The rates of gas and liquid flows were adjusted to achieve a residence time of 0.5 seconds. A switching valve allowed the reactor be either purged with nitrogen, or to be under flow from the reactant stream. Initially the microreactor was in the purge mode and a catalyst wafer was loaded onto the heated chuck and then pneumatically brought into contact with the inlet distribution manifold in the reactant block. On the opposite side of the reactor assembly, a commercial thin-layer chromatography plate cut to 3"×3" was placed in contact with the outlet (discharge) manifold of the microseparator block. The cooling chuck was pneumatically brought down against the TLC plate and sealed the reactor assembly to the catalyst wafer and the TLC plate. The system was allowed to thermally equilibrate for 5 minutes and then the gas stream was switched from nitrogen to the reactant feed stream. The reaction was run for fifteen minutes, during which time reaction products were adsorbed ("trapped") on the detection plate, after which the feed stream was switched back to nitrogen.

Figure 20A:
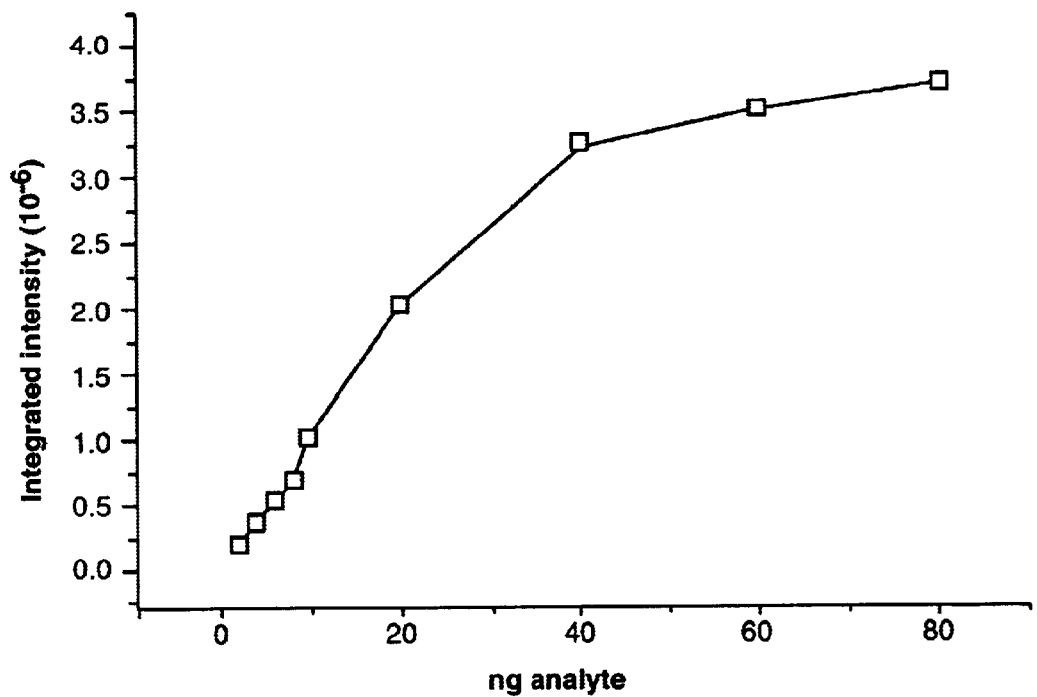
FIG. 20A through FIG. 20F show data resulting from the operation of one embodiment of the chemical processing microsystem of the invention, as described in connection with Example 2.

The cold chuck was opened and the TLC plate was removed from the microprocessing system. After removing the TLC plate, two or more calibration spots were deposited onto the edge of the TLC plate with a syringe, typically, one with 20 ng of analyte and one with 200 ng of analyte. The TLC plate was placed into the spray station and the spray station uniformly sprays the TLC plate with 5 ml of a fluorescamine solution. The plate was removed from the spray station and placed into the imaging station and allowed to develop for 2 minutes, after which a 1024×1024 pixel image was taken with a CCD camera. The fluorescence image can be directly related to the analyte mass using the intensity of the calibration spots. The fluorescence is not a linear function of analyte concentration, so a calibration curve was measured experimentally (FIG. 20A). The microprocessing system was operated either in the low-mass linear portion of the fluorescence detection system, or in some cases, the calibration curve was used to normalize the data.

Figure 20B:
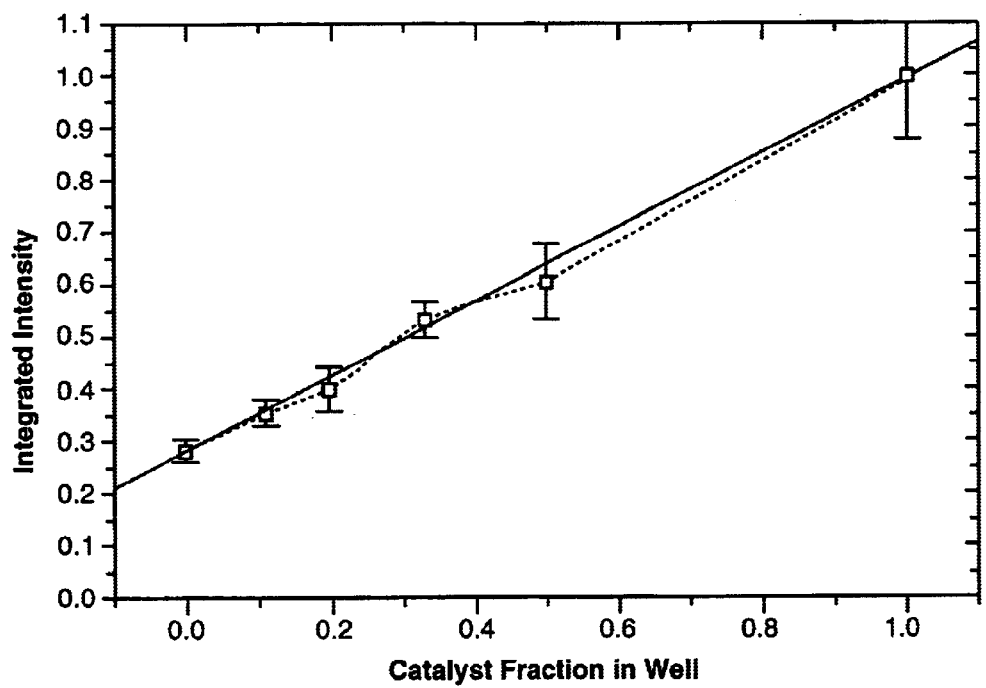

In one experiment, to measure the effect of the varying the catalyst loading in the reactors, different wells were filled with a commercial bulk catalyst diluted with varying amounts of inert material. Each well contained a fixed amount of material, of which the catalyst fraction varied from 10% to 100% catalyst, by weight, relative to total weight of material. Parallel reactions were effected as described above. Integrated. intensities were measured and the variation between multiple wells of the same concentration was also measured (FIG. 20B). Some variation within individual samples was observed (shown by error bars on FIG. 20B), primarily due to variations in the catalyst loading attributable to manual loading procedures. Nonetheless, these data show that final measured signal varied linearly with catalyst loading in the reactor, as expected.

Figure 20C:
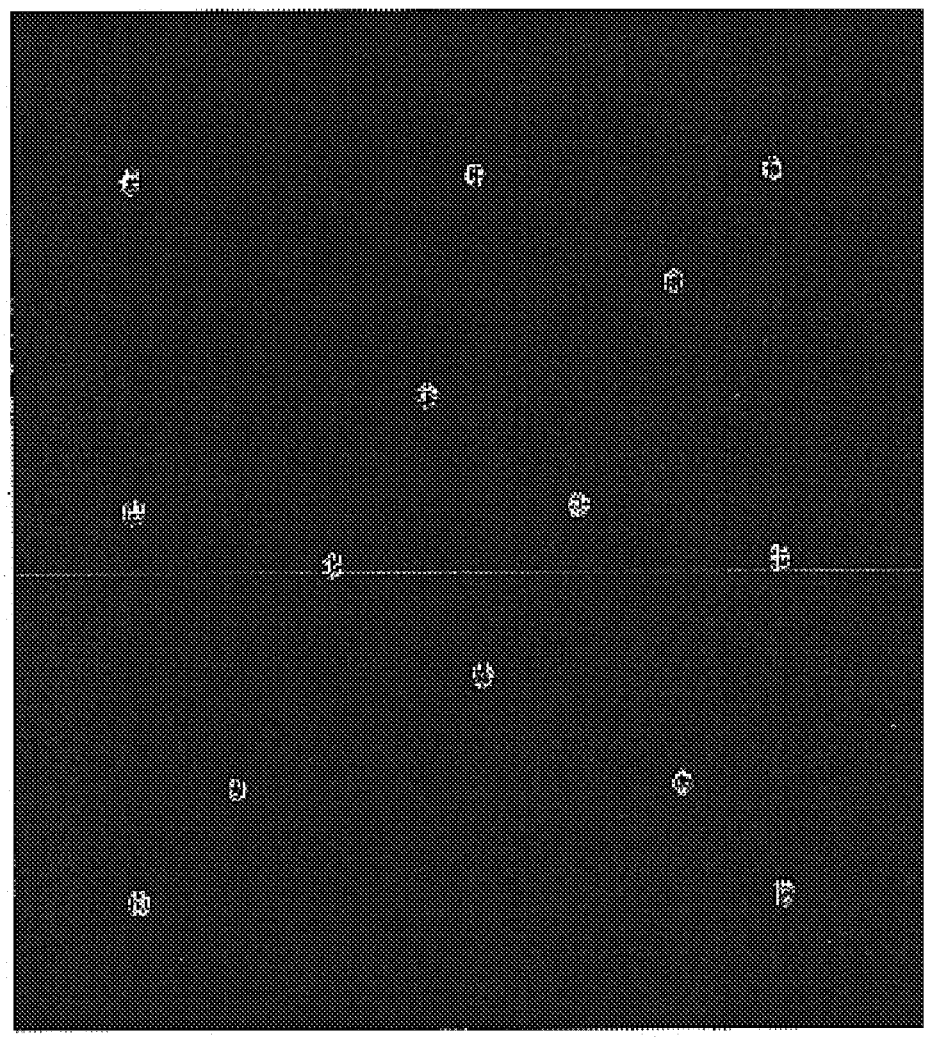

In another set of experiments, it was verified that each microreactor was independent of neighboring microreactors, by measuring cross-talk between channels. Catalysts were loaded into 14 different, spatially separated wells on a 16×16 array of 256 wells formed in the material-containing laminate. The remaining wells contained no catalyst. After running the experimental protocol above, the plate was sprayed with the dye, developed and imaged. FIG. 20C demonstrates that there is no appreciable cross-talk between channels, and that the active channels are all of similar intensity—independent of their location on the wafer. These data, therefore, confirm the uniform distribution of reactants between microreactors and the similar conditions in each microreactor. Additional tests were made with the same catalyst in every well and the distribution of integrated intensities was measured. The measured intensities for each microreactor/microseparator varied less than 15% from the average intensity. The primary sources of error in this experiment were the non-uniformity in the spraying of the dye, and the non-uniformity of the UV illumination field in the imaging station, both of which errors can be reduced through further development of post-reaction processing steps.

A further set of experiments were performed to test the wafer-based synthesis and microreactor/microseparator screening system for correlation to a known catalytic system. Briefly, wafer based mixed-metal oxide ternary libraries were run in the microreactor system as described above, and similar bulk catalysts were run in a more traditional reactor with gas chromatograph detection. The same trends in activity were seen in the wafer-based libraries using the above-described reactor.

Figure 20D:
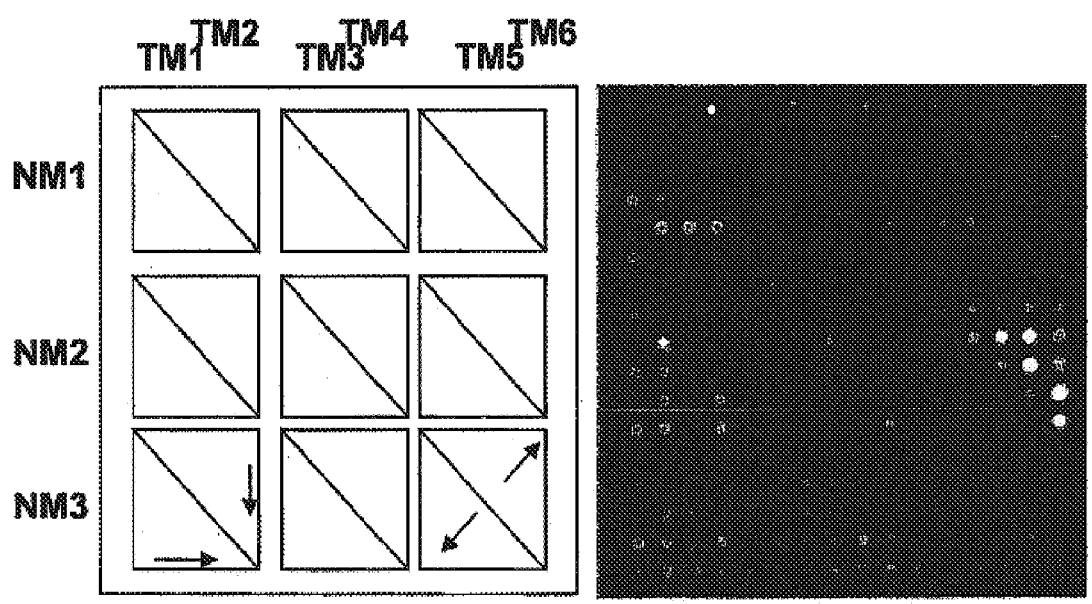
Figure 20E:
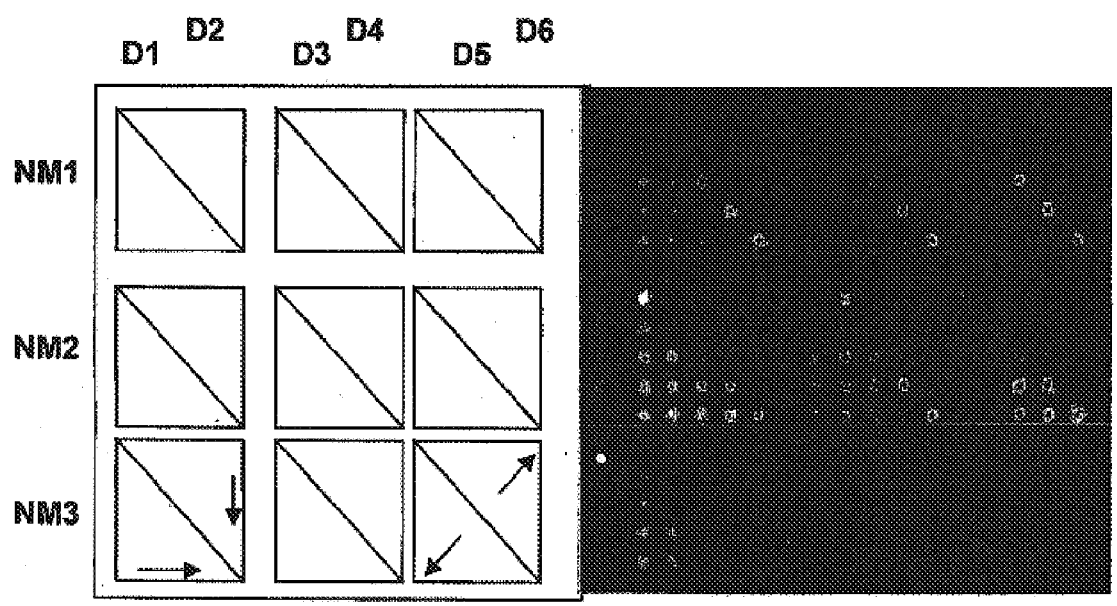
Figure 20F:
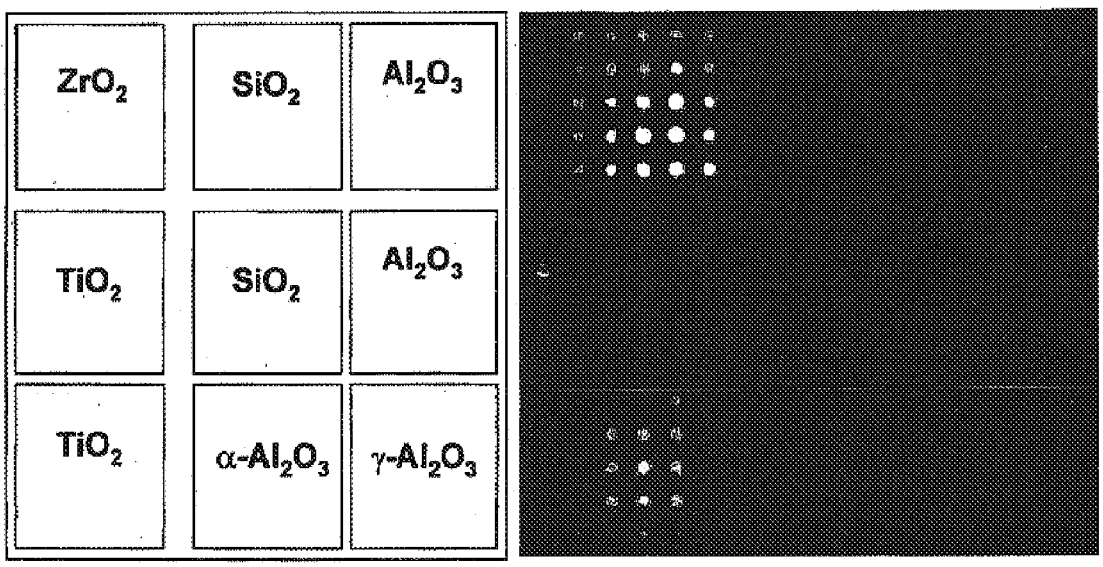

Additional experiments explored the effect of different parameters during the discovery of heterogeneous catalysts. FIG. 20D shows an example of 18 noble metal—transition metal—metal oxide ternaries on a single catalyst wafer. This wafer was screened for catalytic activity using the chemical processing microsystem of the invention substantially as described above. As shown in FIG. 20D, several compositions having catalystic activity—indicated by high intensity of fluorescence (bright spots) were determined. Once promising composition were identified, other compositional parameters, including for example, variations in dopants and supports, were investigated in further experiments. FIG. E shows the data resulting from screening libraries comprising varying dopant concentrations across a set of 18 ternaries. The then-most promising compositions (noble metal, transition metal, dopants) were selected and then used in a further evaluation directed to determining the most promising support material. Specifically, catalyst compositions were screened with a variety of metal-oxide supports, as shown in FIG. 20F, with different pore sizes and compositions. The resulting data show that zirconia is a preferred support, and that titania may also be useful as a catalyst support. Silica and alumina were shown to be less desirable as catalyst supports for the reaction of interest.

In light of the detailed description of the invention and the examples presented above, it can be appreciated that the several objects of the invention are achieved.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

We claim:

1. A chemical processing microsystem comprising a parallel flow microreactor for evaluating catalyzed reactions, the parallel microreactor comprising a microreactor structure comprising four or more microreactors formed in a plurality of adjacent laminae, each of the four or more microreactors comprising a surface defining a reaction cavity having a volume of not more than about 3 ml for carrying out a chemical reaction of interest, an inlet port in fluid communication with the reaction cavity, and an outlet port in fluid communication with the reaction cavity, a fluid distribution system for simultaneously supplying one or more reactants from one or more reactant sources to the inlet port of each of the four or more microreactors through a passive microfluidic fluid-supply manifold and for simultaneously discharging a reactor effluent from the outlet port of each of the four or more microreactors to one or more effluent sinks, and a temperature control device effective for controlling the temperature of the reaction cavity to be above 100° C. during the chemical reaction of interest, at least one of the plurality of laminae being adaptable for use as a material-containing laminate that forms a portion of the cavity-defining surface of the four or more microreactors, the material-containing laminate comprising a substrate for containing at least four catalyst materials arranged on the substrate such that they are individually resident in the reaction cavities of the four or more microreactors, the four or more microreactors being accessible for loading the material-containing laminate prior to carrying out the chemical reaction of interest, and for unloading the material-containing laminate after the chemical reaction of interest.

2. The microsystem of claim 1 further comprising a releasable seal between the material-containing laminate and one or more adjacent laminae in which the microreactors are formed.

3. The microsystem of claim 2 wherein the releasable seal is a gasket.

4. The microsystem of claim 2 wherein the releasable seal is a graphite gasket.

5. The microsystem of claim 1 wherein the microsystem comprises a first laminate having first and second surfaces in spaced, substantially parallel relationship to each other, and an array of the at least four materials, a second laminate having a first surface in releasable contact with the second surface of the first laminate, a second surface in spaced, substantially parallel relationship to the first surface, and an array of four or more wells defined by interior edges of the first surface of the second laminate and by interior surfaces of the second laminate, the array of wells having an arrangement that corresponds to the array of at least four materials formed in the first laminate, such that taken together, the first and second laminates form an array of four or more material-containing microreactors.

6. The chemical processing microsystem of claim 1 wherein the microsystem comprises a first laminate having first and second surfaces in spaced, substantially parallel relationship to each other, and an array of the at least four materials, a releasable seal adjacent the second surface of the first laminate, a second laminate having a first surface adjacent the releasable seal, a second surface in spaced, substantially parallel relationship to the first surface, and an array of four or more apertures defined by interior edges and interior surfaces of the second laminate, and a third laminate having a first surface bonded to the second surface of the second laminate such that, taken together, the second and third laminates form a composite substructure comprising an array of four or more wells defined by the interior edges and interior surfaces of the second laminate and those portions of the first surface of the third laminate circumscribed by such interior edges, the array of wells formed in the composite substructure having an arrangement that corresponds to the array of the at least four materials of the first laminate, such that taken together, the first, second and third laminates form an array of four or more material-containing microreactors.

7. The chemical processing microsystem of claim 1 wherein the microreactor structure comprises ten or more microreactors, and the microfluidic fluid-supply manifold is formed in a plurality of adjacent laminae, the manifold being in sealed contact with a component of the microreactor structure, the manifold comprising one or more common ports adaptable for fluid communication with one or more reactant sources, ten or more terminal ports adaptable for fluid delivery to the ten or more microreactors, and a distribution channel providing fluid communication between the one or more common ports and each of the ten or more terminal ports, the ratio of the number of terminal ports to the number of common ports being not less than about 10:1.

8. The microsystem of claim 7 comprising twenty or more microreactors wherein the ratio of the number of terminal ports to the number of common ports is not less than about 20:1.

9. The microsystem of claim 7 comprising thirty or more microreactors wherein the ratio of the number of terminal ports to the number of common ports is not less than about 30:1.

10. The microsystem of claim 7 comprising fifty or more microreactors wherein the ratio of the number of terminal ports to the number of common ports is not less than about 50:1.

11. The microsystem of claim 7 comprising one-hundred or more microreactors wherein the ratio of the number of terminal ports to the number of common ports is not less than about 100:1.

12. The microsystem of claim 7 wherein the fluid distribution system comprises a manifold having substantially the same resistance to flow between the one or more common ports and each of the ten or more terminal ports, such that the fluid distribution system provides substantially the same flow through each of the ten or more microreactors.

13. The microsystem of claim 7 comprising sixteen or more microreactors, wherein the fluid distribution manifold comprises a common port adaptable for fluid communication with one or more fluid sources or sinks, $2^n$ terminal ports adaptable for fluid delivery to or fluid recovery from $2^n$ microreactors, n being an integer not less than 4, and a distribution channel providing fluid communication between the common port and each of the $2^n$ terminal ports, the distribution channel having a hydraulic radius of not more than about 2.5 mm and comprising $2^n-1$ channel sections connected with each other through $2^n-1$ binary junctions, each of the $2^n-1$ channel sections having at least three access ports serving as the common port, as a connection port for a binary junction, or as a terminal port.

14. The microsystem of claim 13 wherein the $2^n-1$ channel sections are linear channel sections.

15. The microsystem of claim 13 wherein the ten or more microreactors are arranged in a substantially planar array with planar density of not less than about 1 microreactor/$cm^2$.

16. The microsystem of claim 7 wherein the ten or more microreactors are formed in a plurality of laminae.

17. The microsystem of claim 7 wherein the ten or more microreactors are formed in a plurality of laminae, and the fluid distribution manifold is formed in at least one laminate other than the laminae in which the ten or more microreactors are formed.

18. The microsystem of claim 7 wherein the chemical processing microsystem further comprises at least ten different candidate materials individually resident in the ten or more microreactors.

19. The microsystem of claim 7 wherein the distribution channels are adapted such that the pressure drop in each of the fluid distribution channels is larger than the pressure drop in its associated microreactor.

20. The microsystem of claim 7 wherein the microfluidic fluid distribution manifold is releasably sealed with a component of the microreactor structure, such that the manifold can be modularly interchanged with another microfluidic fluid distribution manifold.

21. The chemical processing microsystem of claim 1 wherein the reaction cavity of the microreactors has a volume of not more than about 100 $\mu$l and a geometry defined by ratios of distances X, Y, and Z measured within the reaction cavity along three mutually orthogonal lines having a common point of intersection at a midpoint of the longest line, Z, the X:Z and Y:Z ratios each ranging from about 1:2 to about 1:1.

22. The microsystem of claim 21 wherein the volume of the reaction cavity is not more than about 1 $\mu$l.

23. The microsystem of claim 21 wherein the X:Z and Y:Z ratios each range from about 2:3 to about 1:1.

24. The microsystem of claim 21 wherein the X:Z and Y:Z ratios each range from about 3:4 to about 1:1.

25. The microsystem of claim 21 wherein the X:Z and Y:Z ratios are each about 1:1.

26. The microsystem of claim 21 wherein the chemical processing microsystem further comprises at least four different candidate materials individually resident in the four or more microreactors.

27. The microsystem of claim 21 wherein the microsystem has an essential absence of active mixing elements.

28. The microsystem of claim 21 wherein the microsystem has an essential absence of active mixing elements and static mixing elements.

29. The microsystem of claim 21 wherein the reactor geometry is adapted so that the microreactors are diffusion-mixed microreactors.

30. The microsystem of claim 21 wherein the reactor geometry and the inlet port geometry is adapted so that the microreactors are diffusion-mixed without substantial back-diffusion of reactants into a reactant supply manifold of the fluid distribution system.

31. The chemical processing microsystem of claim 1 wherein the volume of at least two of the four or more microreactors is different.

32. The chemical processing microsystem of claim 1 wherein the volume of at least four of the four or more microreactors is different.

33. The chemical processing microsystem of claim 1 wherein the four or more microreactors are arranged in a substantially planar array and having a planar density of not less than about 5 microreactors/$cm^2$.

34. The microsystem of claim 33 wherein the microreactors are arranged in a substantially planar array with a planar density of at least 10 microreactors/$cm^2$.

35. The microsystem of claim 33 wherein the microreactors are arranged in a substantially planar array with a planar density of at least 25 microreactors/$cm^2$.

36. The microsystem of claim 33 wherein the microreactors are arranged in a substantially planar array with a planar density of at least 50 microreactors/$cm^2$.

37. The microsystem of claim 33 wherein the chemical processing microsystem further comprises at least four different candidate materials individually resident in the four or more microreactors.

38. The chemical processing microsystem of claim 1 further comprising a parallel microseparator comprising four or more microseparators, each of the four or more microseparators comprising a surface defining a separation cavity for separating at least one component of a reactor effluent, an inlet port in fluid communication with the outlet port of one of the microreactors for receiving the reactor effluent therefrom, and an outlet port in fluid communication with the separation cavity for discharging the separated effluent therefrom, the microseparators being formed in a plurality of adjacent laminae, at least one of the laminae being adaptable for use as an adsorbent-containing laminate comprising a substrate and one or more adsorbent materials for adsorbing at least one component of the reactor effluent, the four or more microseparators being accessible for loading the adsorbent-containing laminate prior to carrying out the chemical reaction of interest, and for unloading the adsorbent-containing laminate after the chemical reaction of interest, and a fluid discharge system for discharging the separated effluent from the outlet port of each separation cavity to one or more effluent sinks.

39. The microsystem of claim 38 wherein the chemical processing microsystem further comprises at least four different candidate materials individually resident in the four or more microreactors.

40. The microsystem of claim 38 wherein the microseparators further comprise an adsorbent material that is substantially selective to a reaction product of interest.

41. The microsystem of claim 38 further comprising a releasable seal between the adsorbent-containing laminate and one or more adjacent laminae in which the microseparators are formed.

42. The microsystem of claim 38 wherein the four or more microreactors are formed in a plurality of laminae.

43. The microsystem of claim 38 wherein the four or more microreactors are formed in a plurality of adjacent laminae, at least one of the laminae being a candidate material-containing laminate comprising a substrate and the at least four candidate materials at separate portions of the substrate.

44. The microsystem of claim 38 wherein the four or more microreactors are formed in a first plurality of laminae and the four or more microseparators are formed in a second plurality of laminae, the microsystem further comprising a temperature control block between the first plurality of laminae and the second plurality of laminae.

45. The microsystem of claim 38 wherein the four or more microreactors and the four or more microseparators are formed in a common plurality of laminae.

46. The microsystem of claim 38 wherein each of the four or more microreactors are substantially coplanar with each other and each of the four or more microseparators are substantially coplanar with each other.

47. The chemical processing microsystem of claim 1 wherein the microreactor structure comprises two-hundred-fifty or more microreactors, the material-containing laminate further comprises at least four candidate materials so that the candidate materials are individually resident in the reaction cavity of separate microreactors, each of the candidate materials comprising an inorganic material, a metal-ligand or a non-biological organic material, and the microfluidic fluid-supply manifold is formed in a plurality of laminae.

48. The microsystem of claim 47 wherein the reaction cavity of each of the two-hundred-fifty or more microreactors has a volume of less than about 10 $\mu$l.

49. The microsystem of claim 47 wherein the reaction cavity of each of the two-hundred-fifty or more microreactors has a volume of not more than about 5 $\mu$l.

50. The microsystem of claim 47 wherein the reaction cavity of each of the two-hundred-fifty or more microreactors has a volume of not more than about 1 $\mu$l.

51. The microsystem of claim 47 wherein the amount of the candidate material in each of the candidate-material containing microreactors is not more than about 5 mg.

52. The microsystem of claim 47 wherein the amount of the candidate material in each of the candidate-material containing microreactors is not more than about 1 mg.

53. The microsystem of claim 47 wherein the candidate material comprises an inorganic material.

54. The microsystem of claim 47 wherein the candidate material comprises a metal-ligand.

55. The microsystem of claim 47 wherein the candidate material comprises a non-biological organic material.

56. The microsystem of claim 47 wherein the candidate material consists essentially of elements or compounds selected from the group consisting of an inorganic material, a metal-ligand and a non-biological organic material.

57. The microsystem of claim 47 wherein the candidate material is a film of material formed on a surface of the reaction cavity.

58. The microsystem of claim 47 comprising four-hundred or more microreactors.

59. The microsystem of claim 47 comprising one-thousand or more microreactors.

60. The microsystem of claim 47 wherein the at least four materials are at least four different materials.

61. The microsystem of claim 47 wherein at least eight different candidate materials are individually resident in the reaction cavities of separate microreactors.

62. The microsystem of claim 47 wherein at least fifty different candidate materials are individually resident in the reaction cavities of separate microreactors.

63. The microsystem of claim 47 wherein at least two-hundred-fifty different candidate materials are individually resident in the reaction cavities of separate microreactors.

64. The microsystem of claim 47 wherein different candidate materials are individually resident in the reaction cavities of at least 90% of the microreactors.

65. The microsystem of claim 47 wherein the reaction cavities have a volume that is substantially the same for each of the microreactors.

66. The microsystem of claim 47 wherein the reaction cavities have a volume that is different for at least two of the microreactors.

67. The microsystem of claim 47 further comprising an analytical detection system in fluid communication with the outlet port of one or more of the microreactors.

68. The microsystem of claim 47 wherein each of the two-hundred-fifty or more microreactors is accessible for loading candidate catalyst materials prior to carrying out the chemical reaction of interest and for unloading materials after the chemical reaction of interest.

69. The microsystem of claim 47 wherein a portion of the reaction cavity-defining surface of each of the two-hundred-fifty or more microreactors is formed by a material-containing laminate comprising, a substrate and the at least four materials at separate portions of the substrate.

70. The microsystem of claim 47 wherein the microreactors are formed in a plurality of adjacent laminae.

71. The microsystem of claim 47 wherein the microreactors are formed in a plurality of adjacent laminae, at least one of the laminae being a material-containing laminate comprising a substrate and the at least four materials at separate portions of the substrate, the microsystem further comprising a releasable seal between the material-containing laminate and one or more adjacent laminae in which the microreactors are formed.

72. The microsystem of claim 47 wherein the microreactors are formed in a plurality of adjacent laminae, at least one of the laminae being a material-containing laminate comprising a substrate and the at least four materials at separate portions of the substrate, the material-containing laminate having an essential absence of fluid distribution components.

73. The microsystem of claim 47 wherein the microreactors are formed in a plurality of adjacent laminae, at least one of the laminae being a material-containing laminate comprising a substrate and the at least four materials at separate portions of the substrate, the material-containing laminate having an essential absence of temperature control components.

74. The microsystem of claim 47 wherein the fluid distribution system comprises a manifold comprising at least one common port adaptable for fluid communication with one or more external reactant sources or one or more external reactor effluent sinks, two-hundred-fifty or more terminal ports adaptable for fluid delivery to or fluid recovery from the two-hundred-fifty or more microreactors, and a distribution channel providing fluid communication between the at least one common port and each of the two-hundred-fifty or more terminal ports, the ratio of the number of terminal ports to the number of common ports being not less than about 10:1.

75. The microsystem of claim 74 wherein the ratio of the number of terminal ports to the number of common ports is not less than 100:1.

76. The microsystem of claim 74 wherein the ratio of the number of terminal ports t he number of common ports is not less than 200:1.

77. The microsystem of claim 47 wherein the fluid-distribution system comprises a fluid distribution manifold comprising a common port adaptable for fluid communication with one or more external reactant sources or one or more external effluent sinks, $2^n$ terminal ports adaptable for fluid delivery to or fluid recovery from $2^n$ microreactors, n being an integer not less than 4, and a distribution channel providing fluid communication between the common port and each of the $2^n$ terminal ports, the distribution channel comprising $2^n-1$ channel sections connected with each other through $2^n-1$ binary junctions, each of the $2^n-1$ channel sections having at least three access ports serving as the common port, as a connection port for a binary junction, or as a terminal port.

78. The microsystem of claim 77 wherein each of the channel sections are linear.

79. The microsystem of claim 77 wherein n is an integer of not less than 6.

80. The microsystem of claim 77 wherein n is an integer of not less than 8.

81. The microsystem of claim 77 wherein the microreactors are arranged in a substantially planar array with a planar density of at least 1 microreactor/cm$^2$.

82. The microsystem of claim 47 wherein the reaction cavity of each of the two-hundred-fifty or more microreactors has a geometry defined by ratios of distances X, Y, and Z measured within the reaction cavity along three mutually orthogonal lines having a common point of intersection at a midpoint of the longest line, Z, the X:Z and Y:Z ratios each ranging from about 1:2 to about 1:1.

83. The microsystem of claim 82 wherein the X:Z and Y:Z ratios each range from about 2:3 to about 1:1.

84. The microsystem of claim 82 wherein the X:Z and Y:Z ratios each range from about 3:4 to about 1:1.

85. The microsystem of claim 47 wherein the microreactors are arranged in a substantially planar array with a planar density of at least 1 microreactor/cm$^2$.

86. The microsystem of claim 47 wherein the microreactors are arranged in a substantially planar array with a planar density of at least 5 microreactors/cm$^2$.

87. The microsystem of claim 47 wherein the microreactors are arranged in a substantially planar array with a planar density of at least 10 microreactors/cm$^2$.

88. The microsystem of claim 47 wherein the microreactors are arranged in a substantially planar array with a planar density of at least 5 microreactors/cm$^2$ and the reaction cavity of each of the two-hundred-fifty or more microreactors has a volume of not more than about 1 $\mu$l.

89. The microsystem of claim 47 further comprising two-hundred-fifty or more microseparators, each of the two-hundred-fifty or more microseparators comprising a surface defining a separation cavity for separating at least one component of the reactor effluent, an inlet port in fluid communication with the outlet port of one of the microreactors for receiving the reactor effluent therefrom, and an outlet port in fluid communication with the separation cavity for discharging the separated effluent therefrom.

90. The microsystem of claim 89 wherein the microseparators further comprise an adsorbent material.

91. The microsystem of claim 89 wherein the microseparators are formed in a plurally of adjacent laminae, at least one of the laminae being an adsorbent-containing laminate comprising a substrate and one or more adsorbent materials for adsorbing at least one component of the reactor effluent, the microsystem further comprising a releasable seal between the adsorbent-containing laminate and one or more adjacent laminae in which the microseparators are formed.

92. The microsystem of claim 47 wherein
the two-hundred-fifty or more microreactors are formed in a plurality of adjacent laminae and are arranged in a substantially planar array with a planar density of at least about 1 microreactor/cm$^2$, at least one of the laminae being a material-containing laminate comprising a substrate and at least eight different candidate-materials at separate portions of the substrate, the material-containing laminate having an essential absence of fluid distribution components,
the fluid distribution system comprises a manifold comprising at least one common port adaptable for fluid communication with one or more external reactant sources or one or more external reactor effluent sinks, two-hundred-fifty or more terminal ports adaptable for fluid delivery to or fluid recovery from the two-hundred-fifty or more microreactors, and a distribution channel providing fluid communication between the at least one common port and each of the two-hundred-fifty or more terminal ports, the ratio of the number of terminal ports to the number of common ports being not less than about 10:1.

93. The microsystem of claim 92 further comprising a releasable seal between the material-containing laminate and one or more adjacent laminae in which the microreactors are formed.

94. The microsystem of claim 92 wherein the reaction cavity of each of the two-hundred-fifty or more microreactors has a geometry defined by ratios of distances X, Y, and Z measured within the reaction cavity along three mutually orthogonal lines having a common point of intersection at a midpoint of the longest line, Z, the X:Z and Y:Z ratios each ranging from about 1:2 to about 1:1.

95. The microsystem of claim 92 further comprising two-hundred-fifty or more microseparators formed in a plurality of adjacent laminae, at least one of the laminae being an adsorbent-containing laminate comprising a substrate and one or more adsorbent materials for adsorbing at least one component of the reactor effluent, each of the two-hundred-fifty or more microseparators comprising a surface defining a separation cavity for separating at least one component of the reactor effluent, an inlet port in fluid communication with the outlet port of one of the microreactors for receiving the reactor effluent therefrom, and an outlet port in fluid communication with the separation cavity for discharging the separated effluent therefrom.

96. The chemical processing microsystem of claim 1 in a system for identifying and characterizing materials that enhance a chemical reaction, the system further comprising
a plurality of parallel microseparators, each of the plurality of microseparators comprising an adsorbent material that is selective for one or more reaction products of interest, and
a fluid distribution system for simultaneously supplying one or more reactants from one or more reactant sources to the plurality of microreactors, for simultaneously transferring reactor effluent from the plurality of microreactors to the plurality of microseparators, and for simultaneously discharging the separated effluent from the microseparators,
a station for applying a detection agent to the adsorbent material such that the detection agent can react with the one or more adsorbed reaction products to form a detectable species, and
a detector for detecting the detectable species.

97. The system of claim 96 wherein the detection agent is a dye or colorant.

98. The system of claim 96 wherein the station is a spray station.

99. The system of claim 96 wherein the detector is a parallel detector.

100. The system of claim 96 wherein the detector is a CCD camera.

101. The system of claim 96 wherein the microseparators are formed in a plurality of adjacent laminae, at least one of the laminae being adaptable for use as an adsorbent-containing laminate comprising a substrate and one or more adsorbent materials for adsorbing at least one component of the reactor effluent, the four or more microseparators being accessible for loading the adsorbent-containing laminate prior to carrying out the chemical reaction of interest, and for unloading the adsorbent-containing laminate after the chemical reaction of interest, so that the adsorbent-containing laminate can be transferred to the detection-agent application station.

102. The microsystem of claim 1 wherein the microfluidic fluid-supply manifold is formed in a plurality of adjacent laminae comprising at least one laminate separate from the plurality of adjacent laminae in which the microreactors are formed.

103. The microsystem of claim 1 wherein the temperature control device is effective for controlling the temperature of the reaction cavity to be above about 200° C. during the chemical reaction of interest.

104. The microsystem of claim 1 wherein the temperature control device is effective for controlling the temperature of the reaction cavity during the chemical reaction of interest to range from about 100° C. to about 500° C.

105. The microsystem of claim 1 wherein the temperature control device is effective for controlling the temperature of the reaction cavity during the chemical reaction of interest to range from about 100° C. to about 800° C.

106. The microsystem of claim 1 wherein the fluid distribution system effective for supplying one or more gaseous reactants through the microfluidic fluid-supply manifold.

107. The microsystem of claim 1 wherein the fluid distribution system is effective for supplying one or more gaseous reactants through the microfluidic fluid-supply manifold, and the temperature control device is effective for controlling the temperature of the reaction cavity to be above about 200° C. during the chemical reaction of interest.

108. The microsystem of claim 107 wherein the chemical processing microsystem further comprises four or more inorganic candidate catalyst materials individually resident in each of the four or more microreactors.

109. A chemical processing microsystem comprising a parallel flow microreactor for evaluating catalyzed reactions, the parallel microreactor comprising a microreactor structure comprising four or more microreactors formed in a plurality of adjacent laminae, each of the four or more microreactors comprising a surface defining a reaction cavity having a volume of not more than about 3 ml for carrying out a chemical reaction of interest, an inlet port in fluid communication with the reaction cavity, and an outlet port in fluid communication with the reaction cavity, a fluid distribution system for simultaneously supplying one or more reactants from one or more reactant sources to the inlet port of each of the four or more microreactors through a microfluidic fluid-supply manifold and for simultaneously discharging a reactor effluent from the outlet port of each of the four or more microreactors to one or more effluent sinks, and a temperature control device effective for controlling the temperature of the reaction cavity to be above 100° C. during the chemical reaction of interest, at least one of the plurality of laminae being adaptable for use as a material-containing laminate that forms a portion of the cavity-defining surface of the four or more microreactors, the material-containing laminate comprising a substrate for containing at least four catalyst materials arranged on the substrate such that they are individually resident in the reaction cavities of the four or more microreactors, the material-containing laminate having an essential absence of fluid distribution components, the four or more microreactors being accessible for loading the material-containing laminate prior to carrying out the chemical reaction of interest, and for unloading the material-containing laminate after the chemical reaction of interest.

110. The microsystem of claim 109 wherein the material-containing laminate further has an essential absence of temperature control components.

111. The microsystem of claim 109 wherein the material-containing laminate consists essentially of the substrate and the at least four materials.

112. The microsystem of claim 109 wherein the material-containing laminate consists of the substrate and the at least four materials.

113. The microsystem of claim 109 wherein the microreactors are substantially coplanar with each other.

114. The microsystem of claim 109 wherein the at least one surface of the material-containing laminate is in releasable contact with a surface of adjacent laminae in which the microreactors are formed.

115. The microsystem of claim 109 further comprising a releasable seal between the material-containing laminate and one or more adjacent laminae in which the microreactors are formed.

116. The chemical processing microsystem of claim 109 wherein the material-containing laminate comprises a film of material on at least a portion of the surface defining the reaction cavity of each of the four or more microreactors, the material being selected from the group consisting of inorganic materials, metal-ligand materials and non-biological organic materials.

117. The chemical processing microsystem of claim 116 wherein at least four materials are individually resident as surface films in the four or more microreactors.

118. The chemical processing microsystem of claim 116 wherein the material film is formed by a method selected from physical vapor deposition, chemical vapor deposition, plasma-assisted chemical vapor deposition, electrodeposition, electrochemical deposition, coating techniques, or solution-based techniques.

119. The chemical processing microsystem of claim 116 wherein the material film is formed by solution-based techniques.

120. The chemical processing microsystem of claim 116 wherein the material film is formed by sol-gel techniques.

121. The chemical processing microsystem of claim 116 wherein the material film is prepared by a method that includes forming a film of a catalyst support material on at least a portion of the surface that can define the reaction cavity, and impregnating the catalyst support material with a catalyst or a catalyst precursor.

122. The chemical processing microsystem of claim 109 wherein the microreactor structure comprises ten or more microreactors, and the microfluidic fluid-supply manifold is formed in a plurality of adjacent laminae, the manifold being in sealed contact with a component of the microreactor structure, the manifold comprising one or more common ports adaptable for fluid communication with one or more reactant sources, ten or more terminal ports adaptable for fluid delivery to the ten or more microreactors, and a distribution channel providing fluid communication between the one or more common ports and each of the ten or more terminal ports, the ratio of the number of terminal ports to the number of common ports being not less than about 10:1.

123. The chemical processing microsystem of claim 109 wherein the reaction cavity of the microreactors has a volume of not more than about 100 µl and a geometry defined by ratios of distances X, Y, and Z measured within the reaction cavity along three mutually orthogonal lines having a common point of intersection at a midpoint of the longest line, Z, the X:Z and Y:Z ratios each ranging from about 1:2 to about 1:1.

124. The chemical processing microsystem of claim 109 further comprising
- a parallel microseparator comprising four or more microseparators, each of the four or more microseparators comprising a surface defining a separation cavity for separating at least one component of a reactor effluent, an inlet port in fluid communication with the outlet port of one of the microreactors for receiving the reactor effluent therefrom, and an outlet port in fluid communication with the separation cavity for discharging the separated effluent therefrom, the microseparators being formed in a plurality of adjacent laminae, at least one of the laminae being adaptable for use as an adsorbent-containing laminate comprising a substrate and one or more adsorbent materials for adsorbing at least one component of the reactor effluent, the four or more microseparators being accessible for loading the adsorbent-containing laminate prior to carrying out the chemical reaction of interest, and for unloading the adsorbent-containing laminate after the chemical reaction of interest, and
- a fluid discharge system for discharging the separated effluent from the outlet port of each separation cavity to one or more effluent sinks.

125. The microsystem of claims 1 or 109 wherein the at least four materials are selected from the group consisting of inorganic materials, metal-ligand materials and non-biological organic materials.

126. The microsystem of claims 1 or 109 wherein the microfluidic fluid-supply manifold is formed in a plurality of adjacent laminae.

127. The microsystem of claims 1 or 109 wherein the microfluidic fluid-supply manifold comprises a common port adaptable for fluid communication with one or more reactant sources, four or more terminal ports adapted for fluid delivery to the four or more microreactors, and a distribution channel providing fluid communication between the common port and each of the four or more terminal ports, the flow paths defined between the common port and each microreactors having equal conductance.

128. The microsystem of claims 1 or 109 wherein the microfluidic fluid-supply manifold comprises a common port adaptable for fluid communication with one or more reactant sources, four or more terminal ports adapted for fluid delivery to the four or more microreactors, and a distribution channel providing fluid communication between the common port and each of the four or more terminal ports, the distribution channels being adapted such that the pressure drop in each of the fluid distribution channels is larger than the pressure drop in its associated microreactor.

129. The microsystem of claims 1, 109 or 117 wherein the at least four materials are at least four different materials.

130. The microsystem of claims 1, 109, 116, 7, 21, 33 or 38 wherein the reaction cavity has a volume of not more than about 100 µl.

131. The microsystem of claims 1, 109, 116, 7, 21, 33 or 38 wherein the reaction cavity has a volume of not more than about 10 µl.

132. The microsystem of claims 1, 109, 116, 7, 21, 33 or 38 comprising one-hundred or more microreactors and at least one-hundred different candidate materials individually resident in the reaction cavities of the one-hundred or more microreactors, the at least one-hundred candidate materials being selected from the group consisting of inorganic materials, metal-ligand materials and non-biological organic materials.

133. The microsystem of claims 1, 109, 116, 7, 21, 33 or 38 wherein the microreactors are arranged in a substantially planar array with planar density of not less than about 1 microreactor/$cm^2$.

134. The microsystem of claims 7, 21, 33 or 38 further comprising at least four different candidate materials individually resident in the reaction cavities of the four or more microreactors, the at least four candidate materials being selected from the group consisting of inorganic materials, metal-ligand materials and non-biological organic materials.

135. A method for using the chemical processing microsystem of any one of claims 1, 109, 116, 7, 21, 31, 33, 38 or 47 for identifying or optimizing catalysts for a chemical reaction of interest, the method comprising
- loading at least four materials into the microreactors of the chemical processing microsystem,
- simultaneously contacting each of the at least four materials with the one or more reactants in the microreactors under reaction conditions for the reaction of interest,
- simultaneously discharging a reactor effluent from the material-containing microreactors, and
- evaluating the at least four materials for catalytic activity for the chemical reaction of interest.

136. A method for using the chemical processing microsystem of any one of claims 1, 109, 116, 7, 21, 31, 33, 38 or 47 for evaluating or optimizing process conditions for a chemical reaction of interest, the method comprising
- simultaneously supplying one or more reactants to each of four or more microreactors of the chemical processing microsystem,
- controlling a first set of reaction conditions to be substantially identical in each of the microreactors,
- controlling a second set of reaction conditions to be varied between two or more of the microreactors,
- simultaneously discharging a reactor effluent from each of the four or more microreactors, and
- evaluating the effect of varying the second set of reaction conditions.

137. The microsystem of claims 1, 109, 7, 21, 31, 33 or 47 wherein the fluid distribution system discharges the reactor effluent from the outlet port of each of the four or more microreactors to one or more effluent sinks through a microfluidic effluent-distribution manifold.

138. The microsystem of claims 1, 109, 7, 21, 31, 33 or 47 wherein the fluid distribution system discharges the reactor effluent from the outlet port of each of the four or more microreactors to one or more effluent sinks through a microfluidic effluent-distribution manifold formed in a plurality of adjacent laminae.

139. The microsystem of claims 1, 109, 7, 21, 31, 33 or 47 wherein the fluid distribution system discharges the reactor effluent from the outlet port of each separation cavity to one or more effluent sinks through a microfluidic effluent-distribution manifold formed in a plurality of adjacent laminae.

140. The microsystem of claims 7, 21, 31, 33, 47 or 96 wherein the microfluidic fluid distribution manifold is a microfluidic fluid-supply manifold for simultaneously supplying one or more reactants from one or more reactant sources to the inlet port of each of the microreactors.

141. The microsystem of claims 38 or 96 wherein the fluid distribution system discharges the separated effluent from the outlet port of each separation cavity to one or more effluent sinks through a microfluidic effluent-distribution manifold.

142. The system of claims 38 or 101 wherein the adsorbent-containing laminate further comprises thin-layer chromatography channels associated in corresponding arrangement with each of the separation cavities, each of the thin-layer chromatography channels comprising one or more mobile phase inlet ports, one or more mobile-phase outlet ports, and an adsorbent material that is substantially selective for one or more analytes of interest.

* * * * *

UNITED STATES PATENT AND TRADEMARK OFFICE
CERTIFICATE OF CORRECTION

PATENT NO.   : 6,749,814 B1                                           Page 1 of 1
DATED        : June 15, 2004
INVENTOR(S)  : Bergh et al.

It is certified that error appears in the above-identified patent and that said Letters Patent is hereby corrected as shown below:

<u>Column 76,</u>
Line 1, "1" should be replace with -- 31 --

<u>Column 78,</u>
Line 15, the comma between "comprising" and "a" should be deleted <u>Column 81,</u>
Line 31, the word -- is -- should be inserted between "system" and "effective"

Signed and Sealed this

Seventh Day of December, 2004

JON W. DUDAS
*Director of the United States Patent and Trademark Office*